(12) United States Patent
Needleman et al.

(10) Patent No.: US 11,083,613 B2
(45) Date of Patent: Aug. 10, 2021

(54) GASTRIC OBSTRUCTION DEVICE DEPLOYMENT ASSEMBLY AND METHODS OF DELIVERING AND DEPLOYING A GASTRIC OBSTRUCTION DEVICE

(71) Applicant: BAROnova, Inc., San Carlos, CA (US)

(72) Inventors: David Needleman, San Carlos, CA (US); Alex Roth, Redwood City, CA (US); Daniel R. Burnett, San Francisco, CA (US); Jimmy Van Westenberg, San Francisco, CA (US); Kobi Iki, San Carlos, CA (US)

(73) Assignee: BAROnova, Inc., San Jose, CA (US)

( * ) Notice: Subject to any disclaimer, the term of this patent is extended or adjusted under 35 U.S.C. 154(b) by 333 days.

(21) Appl. No.: 15/878,319

(22) Filed: Jan. 23, 2018

(65) Prior Publication Data

US 2018/0221186 A1    Aug. 9, 2018

Related U.S. Application Data

(60) Provisional application No. 62/449,511, filed on Jan. 23, 2017.

(51) Int. Cl.
*A61F 5/00* (2006.01)

(52) U.S. Cl.
CPC ............ *A61F 5/0089* (2013.01); *A61F 5/003* (2013.01); *A61F 5/004* (2013.01); *A61F 5/0079* (2013.01)

(58) Field of Classification Search
CPC ........ A61F 5/0089; A61F 5/003; A61F 5/004; A61F 5/0079
See application file for complete search history.

(56) References Cited

U.S. PATENT DOCUMENTS

| | | |
|---|---|---|
| 5,509,888 A | 4/1996 | Miller |
| 6,067,991 A | 5/2000 | Forsell |
| 6,527,701 B1 | 3/2003 | Sayet et al. |
| 6,689,046 B2 | 2/2004 | Sayet et al. |
| 7,011,621 B2 | 3/2006 | Sayet et al. |
| 7,037,344 B2 | 5/2006 | Kagan et al. |
| 7,120,498 B2 | 10/2006 | Imran et al. |
| 7,122,058 B2 | 10/2006 | Levine et al. |
| 7,167,750 B2 | 1/2007 | Knudson et al. |

(Continued)

FOREIGN PATENT DOCUMENTS

| | | | |
|---|---|---|---|
| EP | 2340075 | | 3/2013 |
| WO | WO 2014/150894 | * | 9/2014 |

(Continued)

*Primary Examiner* — Jing Rui Ou
(74) *Attorney, Agent, or Firm* — Levine Bagade Han LLP

(57) ABSTRACT

The present invention relates to gastric obstruction device deployment systems and a device for intermittently obstructing a bodily opening, such as a gastric opening, and includes a proximal occluding member connected to a distal occluding member by a tether. The proximal occluding member is formable from an elongated and narrower configuration to a contracted or expanded but wider configuration. When employed in the stomach, the gastric obstruction device may be arranged transluminally with the distal occluding member disposed in the duodenum and the proximal occluding member disposed against the pyloric valve, intermittently occluding the pyloric valve and preventing or delaying the flow of gastric contents through the pyloric valve.

19 Claims, 39 Drawing Sheets

(56) References Cited

U.S. PATENT DOCUMENTS

| | | | |
|---|---|---|---|
| 8,048,169 B2* | 11/2011 | Burnett | A61F 5/003 |
| | | | 623/23.65 |
| 8,585,676 B2 | 11/2013 | Shah | |
| 8,821,584 B2* | 9/2014 | Burnett | A61M 5/14276 |
| | | | 623/23.65 |
| 2004/0172142 A1 | 9/2004 | Stack et al. | |
| 2005/0273060 A1 | 12/2005 | Levy et al. | |
| 2007/0016262 A1 | 1/2007 | Gross et al. | |
| 2007/0027548 A1 | 2/2007 | Levine et al. | |
| 2007/0083224 A1 | 4/2007 | Hively | |
| 2007/0100367 A1 | 5/2007 | Quijano et al. | |
| 2008/0188802 A1 | 8/2008 | Shah | |
| 2009/0118757 A1* | 5/2009 | Burnett | A61F 5/0079 |
| | | | 606/192 |
| 2009/0182357 A1 | 7/2009 | Burnett et al. | |
| 2009/0182358 A1 | 7/2009 | Burnett et al. | |
| 2009/0187200 A1 | 7/2009 | Burnett et al. | |
| 2009/0198210 A1 | 8/2009 | Burnett et al. | |
| 2010/0241177 A1 | 9/2010 | Schaller et al. | |
| 2016/0206461 A1 | 7/2016 | Needleman et al. | |

FOREIGN PATENT DOCUMENTS

| | | |
|---|---|---|
| WO | WO 2016/049149 | 3/2016 |
| WO | WO 2018/136967 | 7/2018 |

\* cited by examiner

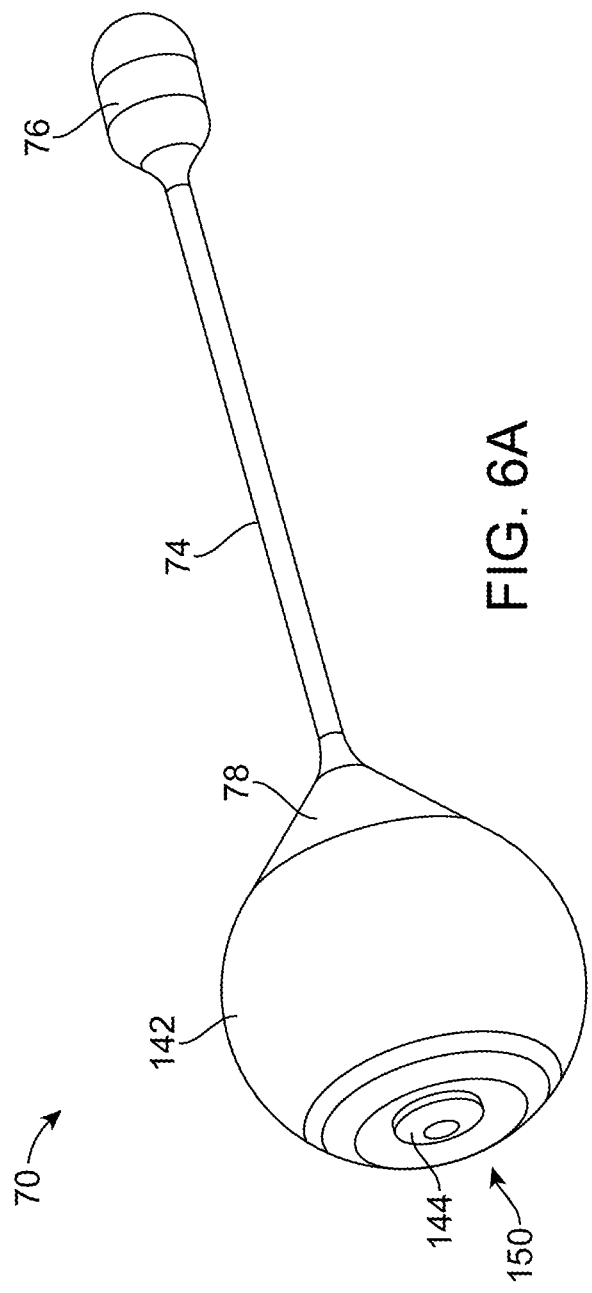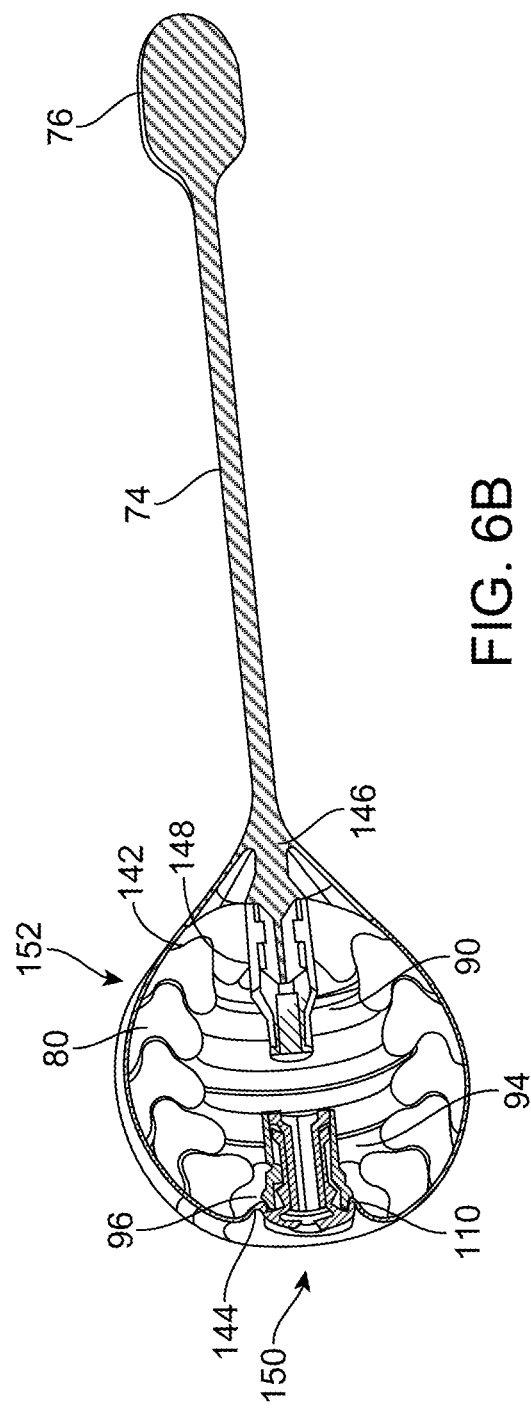

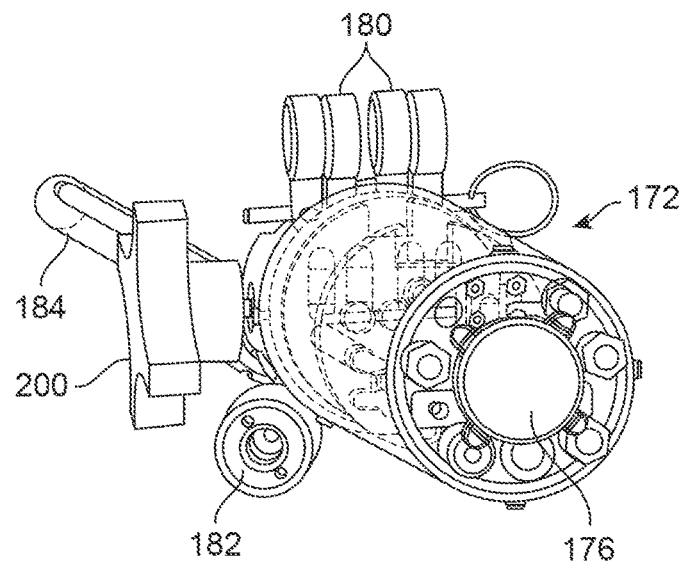
FIG. 20A
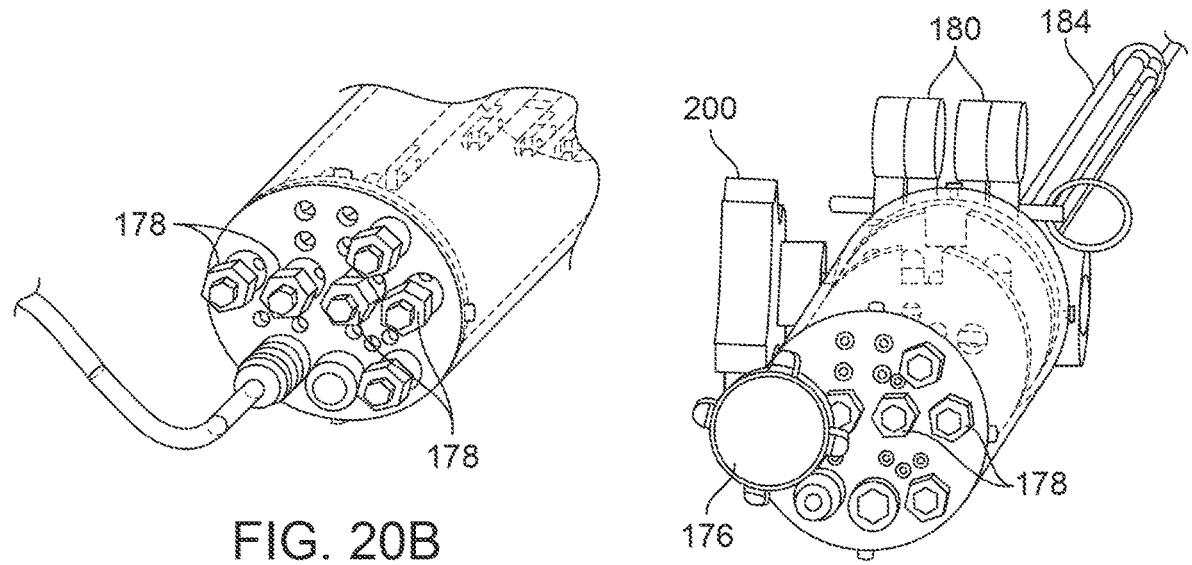
FIG. 20B
FIG. 20C

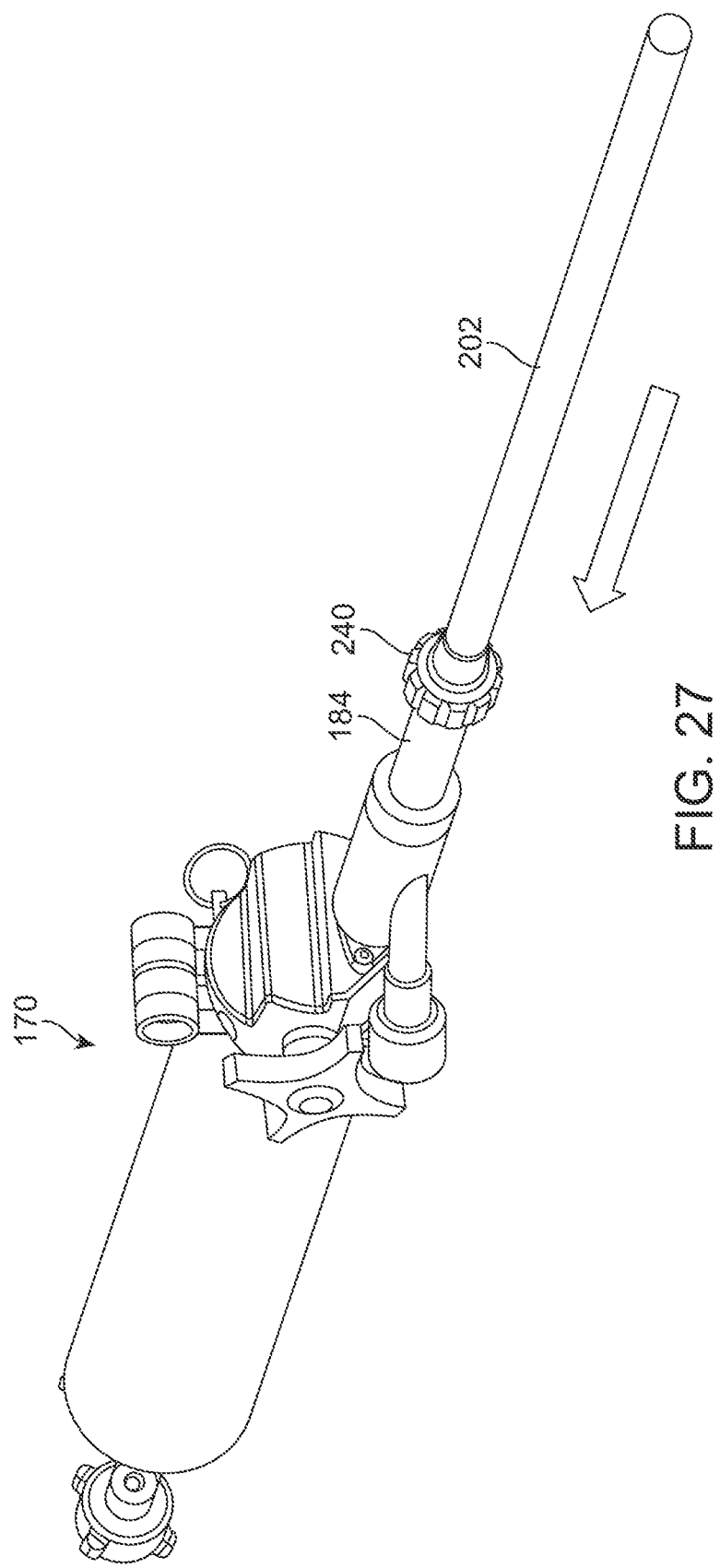

GASTRIC OBSTRUCTION DEVICE DEPLOYMENT ASSEMBLY AND METHODS OF DELIVERING AND DEPLOYING A GASTRIC OBSTRUCTION DEVICE

CROSS-REFERENCE TO RELATED APPLICATIONS

This application claims the benefit of priority to U.S. Provisional Application No. 62/449,511 filed Jan. 23, 2017, which is incorporated herein by reference in its entirety.

TECHNICAL FIELD

The present invention relates to a gastro-intestinal device deployment system for delivering, deploying, reconfiguring, and releasing a gastric obstruction device for treating obesity and other medical conditions. More particularly, the gastric obstruction device can be a device that is positioned trans-luminally in a patient's gastro-intestinal tract to intermittently obstruct or reduce the flow of gastric contents and deployment systems for delivering, reconfiguring, and releasing such intermittently obstructive devices.

BACKGROUND

Obesity is a condition of epidemic proportions in the United States. Recent government studies have indicated that up to 40% of Americans are obese and that, among those, almost 20% are morbidly obese. Patients who are obese are tend to suffer from cardiovascular disease, heart disease, stroke, diabetes, and obstructive sleep apnea. Recent studies have indicated that obesity can reduce a person's lifespan by an average of three years in adults and twenty years in children.

Many attempts have been made in the prior art to provide medications, devices, and surgical procedures for the treatment of obesity, all of which either have serious side effects or are basically ineffective. For example, various diets, supplements and pharmaceuticals have been developed and marketed, but none have shown any significant benefits to date in the treatment of obesity with the exception of some pharmaceuticals, which have unfortunately been found to cause a number of serious, life-threatening medical conditions. To date, there are no commercially available supplements or drugs that have been proven to be effective in promoting significant weight loss and at the same time that are free from serious collateral side effects.

Recognizing that no cure has been developed to date that is both effective and safe, the medical industry has introduced more extreme procedures, an example of which is the Roux-En-Y gastric bypass. This extensive and invasive surgery is highly effective but is also potentially lethal, with a 1-2% mortality rate, a six month recovery period, and a cost of tens of thousands of dollars, yet it is becoming increasingly popular because other available treatments do not produce the desired results. Gastric reduction, or simply removing a large segment of the stomach, is another procedure that is similar to gastric bypass and that, like gastric bypass, has also been associated with potentially lethal complications. Data from recent studies have indicated that even in the lowest risk groups, obesity surgery causes an average one-year mortality rate of nearly 5%.

In another attempt to treat obesity, devices have also been developed in the prior art that are aimed at providing a sense of fullness to a patient, so to cause the patient to reduce food intake. Such devices may be configured as stents that support the stomach or the pyloric valve or that may be configured as permanent occluders. Unfortunately, these devices are implanted in the patient on an essentially permanent basis and typically include complex mechanical or electrical features that may stop working properly over time or that may require maintenance from time to time. Examples of such devices in the prior art can be found in U.S. Pat. Nos. 5,509,888; 6,067,991; 6,527,701; 6,689,046; 7,011,621; 7,037,344; 7,120,498; 7,122,058 and 7,167,750, and in U.S. Patent Application Publications Nos. 2004/0172142; 2005/0273060; 2007/0016262; 2007/0027548; and 2007/0083224.

Evidence has been developed showing that benefits can be derived from reducing gastroduodenal flow. In unpublished, but recently presented data at the American Society for Bariatric Surgery conference of June 2003, stimulation of the gastric vagus nerve with subsequent reduction in gastric motility resulted in a loss of over 20% of excess weight over a nine-month period. Furthermore, there is data suggesting that gastric vagotomy is also effective in the treatment of obesity through a similar mechanism. Unfortunately, these therapies require highly invasive, sometimes irreversible, surgical procedures, making them undesirable for a large segment of the obese population.

SUMMARY

Disclosed is a gastro-intestinal device deployment system for delivering, deploying, reconfiguring, and releasing a gastric obstruction device for treating obesity and other medical conditions. It is also an object of the present invention to provide a device for the treatment of obesity and related conditions that is well tolerated by the stomach and in general, by the gastro-intestinal tract. It is a further object of the present invention to provide a device for the treatment of obesity and related conditions that can be implanted and removed with medical procedures that are safe and relatively simple to perform.

The delivery and deployment assembly for delivering and deploying an intermittently obstructive gastric obstruction device can comprise a delivery tube having a lumen there through and a distal opening; a control tube slidably positioned through the delivery tube; a control assembly attached at a proximal end of the delivery tube; one or more tension lines extending through the control assembly and through the delivery tube; a tensioning mechanism within the control assembly and in communication with each of the one or more tension lines for maintaining the tension lines under tension; and an advancement control positioned along the control assembly and operatively coupled to the control tube. The tensioning mechanism can be configured to release the one or more tension lines to release the tension. The assembly can further comprise a mechanism for cutting or releasing the one or more tension lines.

The gastric obstruction device can be positioned within the lumen of the delivery tube while in an elongated and collapsed configuration. A compliant pyloric contact section of the gastric obstruction device can be coupled to a distal end of the control tube. The one or more tension lines extending through the delivery tube can further extend through the gastric obstruction device when at least part of the gastric obstruction device is within the delivery tube. In addition, an anchor line can be positioned through the control assembly and can pass through the gastric obstruction device.

The delivery and deployment assembly can include a control interface along the control assembly. The control interface can have one or more actuation mechanisms coupled to a corresponding tension line for further applying a tensile force to the corresponding tension line. The control tube can be configured to slidably advance to a distal position where the control tube decouples from the advancement control. The control tube can extend at least partially within the control assembly.

The delivery and deployment assembly can further include a plunger slidably translatable within the delivery tube and extending from the control assembly and into the delivery tube to push the gastric obstruction device out of the delivery tube. The plunger can define one or more projections or depressions along a length of the plunger for engagement with the advancement control.

The delivery and deployment assembly can also comprise a first carriage slidably positioned through the control assembly, the first carriage being attached to a proximal end of the control tube and further comprising a plunger release mechanism which releases the plunger from the carriage when actuated. The assembly can also comprise a pressure indicator in fluid communication with the delivery tube. In addition, the assembly can also comprise a pressure regulator or mechanism in communication with the pressure indicator and a port in fluid communication with the delivery tube.

The assembly can also comprise one or more wire access handles positioned along the control assembly, wherein the one or more tension lines pass through a corresponding shaft of the wire access handle.

The assembly can further comprise a flange extending from a distal end of the delivery tube. The assembly can also comprise a device cover attached to the flange.

The assembly can further comprise an access sheath slidably positionable over the delivery tube. The assembly can also comprise an inflatable member positioned at or near a distal end of the access sheath.

A method of delivering and deploying an intermittently obstructive gastric obstruction device is also disclosed. The method involves advancing a delivery tube distal end per-orally into proximity of a stomach of a patient; advancing a control tube slidably positioned through the delivery tube, wherein a conforming portion of the gastric obstruction device positioned within the delivery tube is released from the delivery tube by the control tube; advancing the gastric obstruction device while maintaining a position of the control tube relative to the delivery tube distal end such that the gastric obstruction device is advanced distally of the delivery tube distal end and nests into a compacted configuration; tightening one or more lock lines passing through the gastric obstruction device in its compacted configuration until a corresponding tensioning wire pin is locked to maintain the compacted configuration; and releasing the gastric obstruction device from the delivery tube.

Another method of delivering and deploying an intermittently obstructive gastric obstruction device comprises advancing a delivery tube distal end per-orally into proximity of a stomach of a patient; advancing a control tube slidably positioned through the delivery tube such that a distal portion of the gastric obstruction device is released from the delivery tube; maintaining a position of the control tube relative to the delivery tube distal end such that the gastric obstruction device is advanced distally of the delivery tube distal end and nests into a compacted configuration whereby the gastric obstruction device is formed from its distal end and towards its proximal end into its deployed configuration; and tightening one or more lock lines passing through the gastric obstruction device in its compacted configuration until a corresponding tensioning wire pin is locked to maintain the compacted configuration.

In one variation, advancing a delivery tube further comprises advancing a delivery tube having a device cover attached to the distal end. The gastric obstruction device can be advanced distally of the delivery tube and into an interior of the device cover.

Advancing a control tube further comprises actuating an advancement control on a control assembly attached to the delivery tube. In addition, advancing the gastric obstruction device comprises advancing a plunger through the delivery tube to push the gastric obstruction device. Furthermore, advancing the plunger comprises releasing the plunger via a release mechanism from a first carriage slidably positioned within the control assembly.

Tightening the one or more lock lines further comprises actuating a tension control positioned along the control assembly to apply tension to one or more tension lines coupled to the lock lines. The method further involves cutting or releasing the one or more tension lines. In addition, releasing the gastric obstruction device comprises releasing an anchor line from the gastric obstruction device. Moreover, releasing the anchor line from the gastric obstruction device is done via the control assembly.

The method further comprises insufflating the stomach prior to advancing a control tube. The method also comprises monitoring a pressure within the stomach. The method further comprises visualizing the gastric obstruction device while advancing a control tube. The method further comprises inserting the delivery tube into an access sheath prior to advancing a delivery tube.

The method further comprises inflating an expandable member near or at a distal end of the access sheath within the stomach of the patient. The method further comprises retracting the expandable member against a lower esophageal sphincter of the stomach of the patient.

The method further comprises removing the delivery tube from the stomach of the patient to finish the delivery and deployment procedure.

Another method of delivering and deploying an intermittently obstructive gastric obstruction device is disclosed, the method comprising advancing an access sheath per-orally into proximity of a patient stomach, wherein an obturator is coupled to the access sheath during introduction into the patient stomach; removing the obturator from the access sheath when a distal end of the access sheath is in the patient stomach; inflating an expandable member on the distal end of the access sheath in the patient stomach; and advancing the gastric obstruction device through the proximal end of the access sheath into the patient stomach at the distal end of the access sheath. The access sheath can be coupled to the obturator. The method can further involve advancing an endoscope through the access sheath. The method can also involve deflating the expandable member.

The gastric obstruction device of the present invention operates as a transluminal device that obstructs the pylorus or another organ on an intermittent basis and that causes a reduced flow of gastric contents into the intestinal tract. The device of the present invention may just occupy space in the stomach and occlude the pyloric valve from time to time, or also may partially obstruct the duodenum or the small intestine, reducing overall gastrointestinal transit. The intermittent blockage of the gastrointestinal tract results in weight loss and also in an increased or sustained feeling of fullness by the patient.

The device of the present invention can be placed and removed with simple endoscopic procedures and is completely reversible. In particular, the device of the present invention can be inserted and removed orally, nasally or transcutaneously and, in certain embodiments, can be triggered externally or can be caused to expand or can self-expand once in the gastrointestinal space.

In some variations, a gastric obstruction device includes a proximal occluding member oriented in the direction of the stomach after implantation and a distal occluding member oriented in the direction of the duodenum after implantation that are connected by a tether.

The proximal occluding member is composed of a coiled member surrounded by an apron cover. The coiled member is formable from an elongated, narrower configuration to a contracted, wider configuration, while the apron cover has an essentially cylindrical portion that surrounds the coiled member and an essentially conical portion that connects the apron cover to the tether, providing the apron cover with a funnel-like shape. In one embodiment, the cylindrical portion is spaced from the coiled member by an interstice or gap, and the cylindrical and conical portions may have different wall thickness. The coiled member may be formable from a narrower elongated configuration to a wider configuration by compressing the coiled member.

In one embodiment, the elongated configuration exhibits a helical contour with a plurality of turns, and the wider configuration is formed from the helical configuration by nesting the turns one adjacent to the other to provide a bulbous body. The wider configuration is then locked in place by engaging a connecting member at the proximal end of the coiled member with a mating cavity at the distal end of the coiled member. This may be achieved by having a clinician pull on a string coupled to the connecting member in the direction of the mating cavity.

In one embodiment, such coupling string extends outside of the device along its entire length and then enters a lumen running from the coiled member to the distal occluding member through the tether. When entering the coiled member, the string is looped through the connecting member and is removable from the device after the connecting member has engaged the matching cavity. The proximal end of the coiled member may be reinforced to increase its resistance to tearing during the compression of the coiled member by including a reinforcing material in at least part of the structure of the proximal end.

The transformation process from the elongated configuration to the wider configuration is reversible, so that the device can be implanted in the stomach in the elongated configuration, reside in the stomach and/or gastro-intestinal tract in the wider configuration, and be removed from the stomach through the esophagus in the elongated configuration. In one embodiment, the wider configuration reverses to the elongated configuration by severing the connecting member from the proximal end, for example, by having a clinician cut a string coupling the connecting member to the proximal end or to a release member in the proximal end.

A device according to the present material is manufactured from a material that is biocompatible, that is able to withstand the gastrointestinal environment, and that prevents or anyways minimizes abrasion of the walls of the stomach and duodenum, particularly of the pyloric valve. In one embodiment, the device is manufactured from a resilient plastic material, for example, from a silicone material, and the apron cover may be constructed to be flexible enough to reverse from a position surrounding a portion of the tether to a position surrounding the coiled member, in order to facilitate insertion in the stomach according to one method of use.

The distal occluding member also may have a bulbous shape (e.g., a pod or ellipsoid shape) and include an insert having a heavier weight than the remainder of the distal occluding member, so to facilitate disposition and retention in the duodenum.

The device of the present invention is suited not only for the treatment of obesity, but also for treating other ailments, such as improper glucose tolerance in a diabetic or prediabetic subject and the progression of diabetes itself by inhibiting fasting insulin secretion or glucose-stimulated insulin secretion. The resent device is also suited for treating other ailments deriving from obesity, including hyperphagia, dyslipidemia, Prader Willi syndrome, Froelich's syndrome, Cohen syndrome, Summit syndrome, Alstrom syndrome, Borjesen syndrome, Bardet-Biedl syndrome, or hyperlipoproteinemia, types I, II, III, and IV.

The device of the present invention may also include sensors or transmitters to provide feedback and other data to an intra-corporeal or extra-corporeal processor, or may carry one or more compounds stored in a reservoir within the device or coated on the device.

In one embodiment, insulin is released into the gastrointestinal tract by disposing an insulin reservoir in the distal occluding member of the device. Such a release of insulin may be controlled by the size of the orifice between the reservoir and the outer environment, or by a time-controlled actuator, or by an actuator controlled by one or more sensors, for example in response to detection of sugar in the gastrointestinal tract.

Additionally, alternative devices and their methods of use which may be used with the features described herein in various combinations are further described in detail in U.S. patent applicatin Ser. No. 12/205,403 filed Sep. 5, 2008 (US Pub. 2009/0198210); U.S. patent application 12/352,497 filed Jan. 12, 2009 (US Pub. 2009/0182357); and U.S. patent application Ser. No. 12/352,508 filed Jan. 12, 2009 (US Pub. 2009/0182358), each of which is incorporated herein by reference in its entirety for any purpose.

Furthermore, assemblies and systems for delivering and deploying these obstructive devices may also be used to deliver the devices in a collapsed, uncoiled, and elongated configuration. Once in position within the patient's body (e.g., advancing a delivery tube distal end per-orally into proximity of a patient's stomach), an advancement control on a control assembly may be used to advance the collapsed and uncoiled proximal occluding member via a control tube into the stomach. A plunger may be optionally used to further advance (e.g., by pushing) the proximal occluding member such that it is pushed out of a delivery tube into its coiled and nested configuration external to the delivery tube while a distal portion of the proximal occluding member is maintained at a distance from the delivery tube.

Variations of the obstructing device and its methods of use are further described in detail in U.S. App. 61/791,433, filed Mar. 15, 2013, which is incorporated herein by reference in its entirety for any purpose.

With the proximal occluding member reconfigured in its coiled and compacted configuration, one or more lock lines may be tightened through the proximal occluding member via a corresponding tension control interface including tension lines coupled to the lock lines until the proximal occluding member is locked in its deployment configuration. While the lock lines are passed through the proximal occluding member and are used to reconfigure and lock the obstructing device into its deployed configuration, the tension lines may be separate from the lock lines and may also correspond to each of the lock lines and may extend from the gastric obstruction device and through the control assembly. Moreover, the tension lines may lead either to the proximal end of the coiled member (in which case the entire coiled member may be delivered into the stomach before reconfiguration) or the tension lines may lead through the middle of the coiled member and then outward in a retrograde fashion through the walls of the coiled member which enables reconfiguration of the coiled member as it emerges from the delivery tube in a much more controlled process.

In another variation, the tension lines can be coupled to lock lines which are used to lock the gastric obstruction device in its compressed, wound, and nested configuration. The tension lines can be used to pull the gastric obstruction device through the delivery tube and out of the delivery tube into a device cover or skin. The tension lines can extend from the delivery assembly, through the turns of the coiled member of the gastric obstruction device, and back into the delivery assembly through a lumen of a control tube. The tension lines can be detached or otherwise separated from the lock lines. The tension lines can then be cut and removed from the gastric obstruction device (e.g., through the control tube) when the gastric obstruction device is locked by the locked lines in the nested or wound configuration.

The tension lines coupling the gastric obstruction device to the delivery assembly may have any tension released prior to being cut. Additionally, an anchor line coupling the obstructing device to the control assembly may also be released and removed from the control assembly and the gastric obstruction device to finally deploy the gastric obstruction device into the patient's stomach.

BRIEF DESCRIPTION OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

FIGS. 6A and 6B show perspective and cross-sectional perspective views of a covered obstructing assembly comprising a device cover or skin.

FIGS. 20A to 20C show various perspective view of the control assembly actuated for locking the obstructing device.

FIG. 27 shows a perspective view of the disengagement of the delivery tube from the overtube for removal from the patient body.

DETAILED DESCRIPTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Figure 1A:
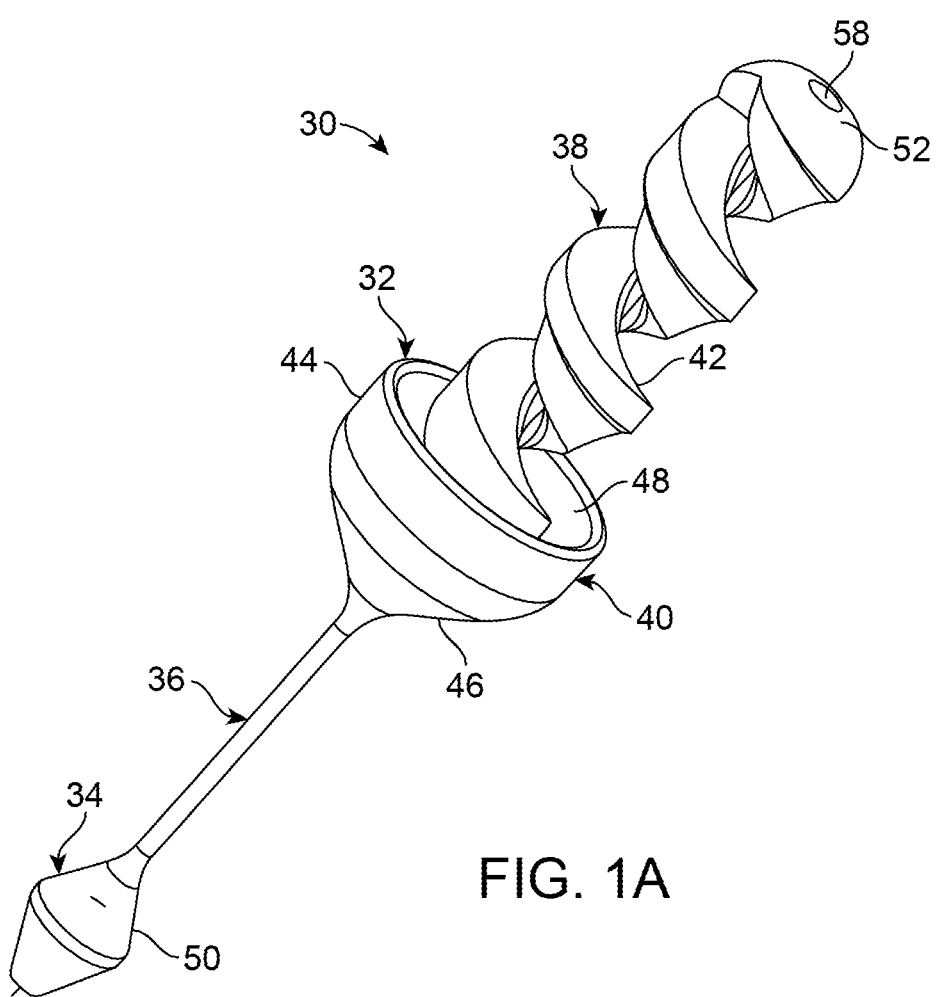
FIG. 1A illustrates a perspective view of a first embodiment of the invention in the elongated, narrower configuration.

FIG. 1A depicts one variation of a gastric obstruction device 30, which is configured for insertion into a patient's organ, typically the stomach. The gastric obstruction device 30 includes a proximal occluding member 32 and a distal occluding member 34, which are connected one to the other by a tether 36. The relative sizes of proximal occluding member 32 and of distal occluding member 34 are such that, after insertion into the stomach of a patient, the natural contractions of the stomach and, in general, the movements of the patient induce distal occluding member 34 to enter the pyloric part of the gastro-intestinal tract and the duodenum, while proximal occluding member 32 is retained in the stomach and cannot move beyond the pyloric valve because its diameter is larger than the pyloric valve opening.

Figure 1B:
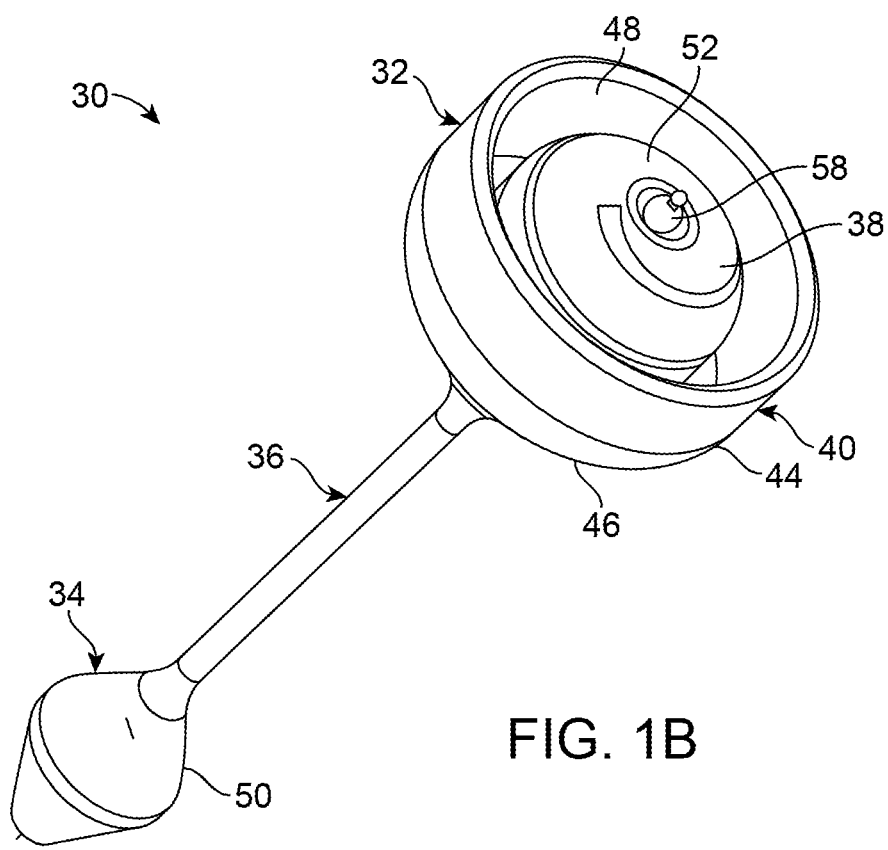
FIG. 1B illustrates a perspective view of the embodiment of FIG. 1A in the contracted, wider configuration.

More particularly, proximal occluding member 32 includes a coiled member 38, disposed in a central position within an apron cover 40. Coiled member 38 may be formed from an elongated, narrower configuration as shown in FIG. 1A to a contracted, wider configuration as shown in FIG. 1B. In the embodiment illustrated in FIG. 1A, coiled member 38 has a helical design with a plurality of turns 42, which are configured to nest one adjacent to the other to assume the compact, bulbous shape illustrated in FIG. 1B.

Apron cover 40 wraps around coiled member 38, providing proximal occluding member 32 with an enlarged diameter and preventing the passage of proximal occluding member 32 through the pyloric valve. In one variant of the present embodiment, apron cover 40 includes an essentially cylindrical proximal portion 44 connected to an essentially conical distal portion 46 that extends from tether 36 to proximal portion 44. This configuration of apron cover 40 is designed to provide an intermittent plugging effect on the pyloric valve and to avoid or anyways minimize abrasive contact with the wall of the pyloric valve during such plugging effect, so to prevent or minimize patient discomfort and irritations or even lacerations to the mucosa of the stomach and, in general, to the gastro-intestinal tract.

Distal portion 46 may have a smaller wall thickness than proximal portion 44, both providing a gentler or softer contact with the pyloric valve, and also facilitating the reversal of apron cover 44 during insertion into a patient's stomach from a position substantially aligned with tether 36 to the position that wraps around coiled member 38, as explained in greater detail below.

In different variants of the present embodiment, apron cover 40 may extend proximally for various lengths, surrounding coiled member 38 partially or completely. Further, in different variants of the present embodiment, apron cover 40 may be spaced from coiled member 38 at various distances to create an interstice 48 of different amplitudes between coiled member 38 and apron cover 40.

Distal occluding member 34 may exhibit a variety of contours and in general, is shaped to facilitate its transition out of the stomach and into the duodenum, and to avoid or minimize abrasive contact with the walls of the stomach and of the pylorus. In one variation, the distal occluding member 34 has a bulbous or ellipsoid shape, essentially formed by two rounded, frusto-conical portions 50 connected at their wider bases.

The gastric obstruction device 30 may be manufactured from a variety of materials, for example, from a resilient plastic such as a silicone or urethane plastic, which may be reinforced in selected portions. In general, the selected material should be biocompatible, resistant to the stomach environment, for example to stomach acids, and soft to the contact with the stomach and duodenal walls. The desired material should also provide the gastric obstruction device 30 with the desired shape while retaining sufficient flexibility for the insertion process in the stomach, for later reverting to the desired position within the gastro-intestinal tract, and for adapting to the various movements of the stomach and, in general, of the body of the patient.

Inserts may be integrally included within the body of the gastric obstruction device 30 to increase certain mechanical properties in certain areas. For example, an insert (such as a metallic cylinder) may be embedded within distal occluding member 34 to increase weight and to facilitate retention by gravity within the pylorus. Another insert (such as a fabric piece) may also be embedded in proximal end 52 of coiled member 38, increasing resistance to tear when proximal end 52 is pulled outwards to extend coiled member 38 to the configuration of FIG. 1, or inwards to stabilize coiled member 38 in its contracted, wider configuration, as explained in greater detail below.

Figure 1C:
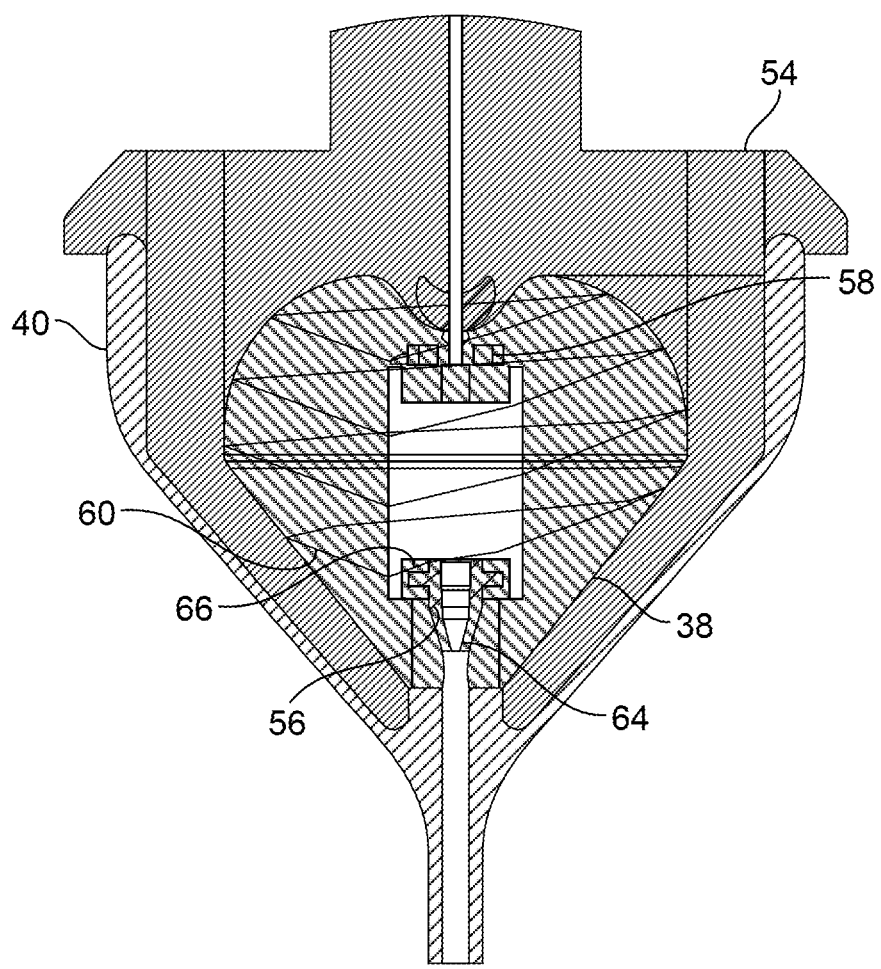
FIGS. 1C-1E illustrate respectively a cross-sectional view of the proximal occluding member of the embodiment of FIG. 1B, to which a protective cap has been added (FIG. 1C); a side view of the embodiment of FIG. 1B with the protective cap (FIG. 1D); and a cross-sectional view of the embodiment of FIG. 1D (FIG. 1E).
Figure 1D:
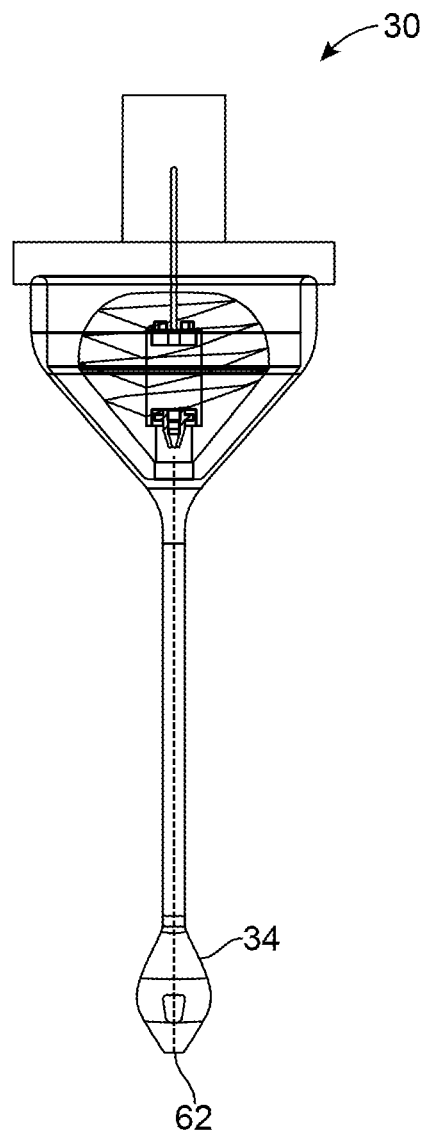
Figure 1E:
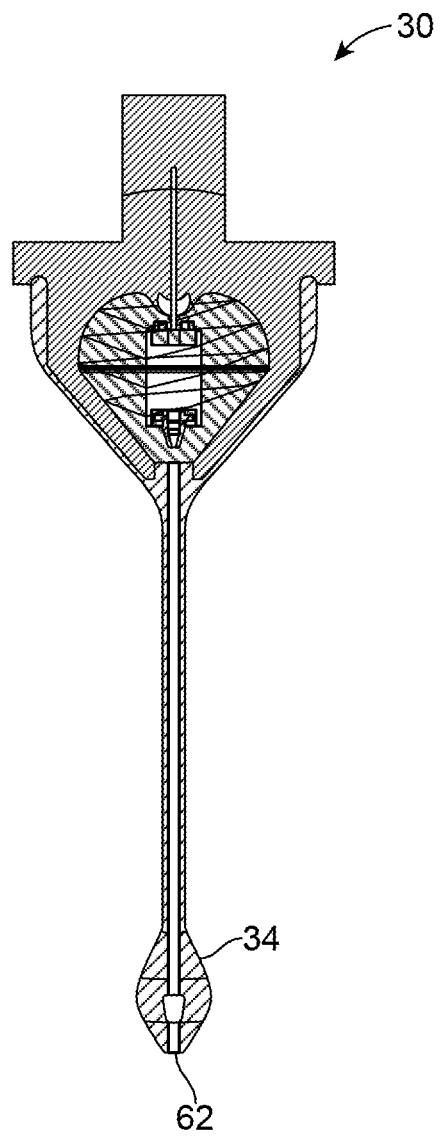
Figure 1F:
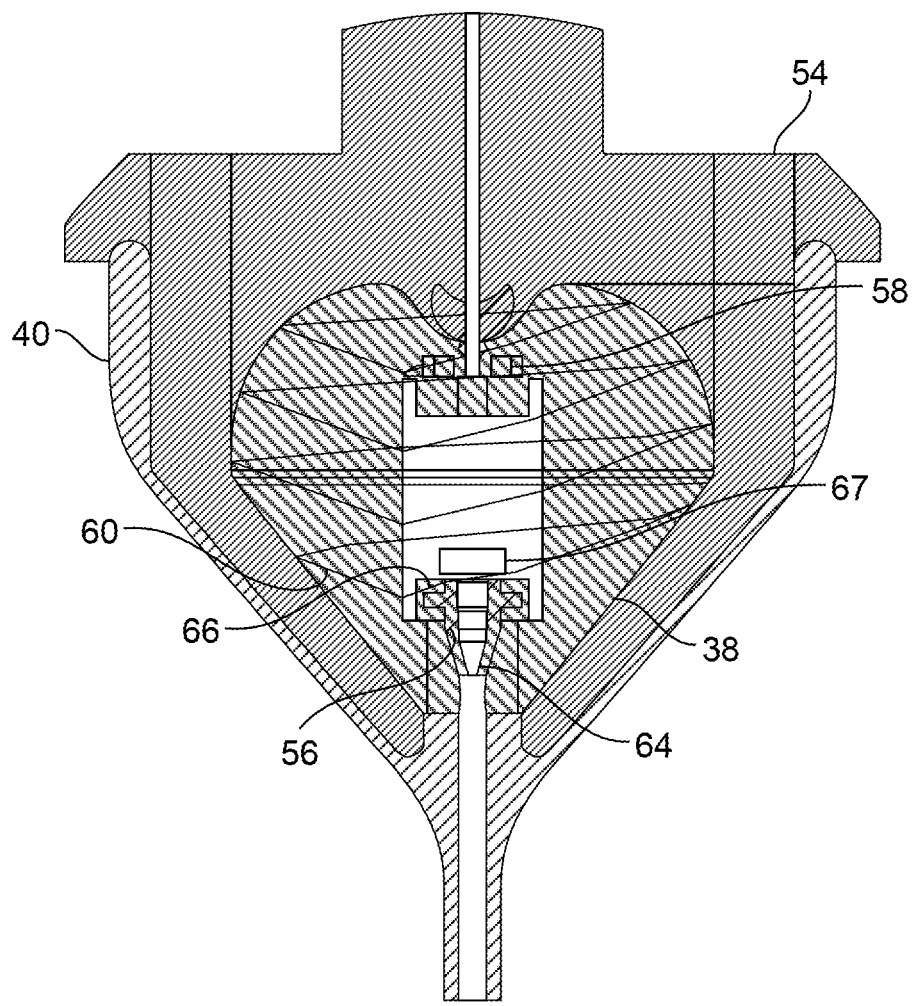
FIG. 1F illustrates a cross-sectional side view of one example of a device having a sensor incorporated within for confirming or detecting whether the proximal occluding member has been locked into its deployment configuration.

The insertion of the gastric obstruction device 30 in a patient's stomach will now be described with reference to FIG. 1C. It should be noted that FIG. 1C illustrates, among other things, one variant of the embodiment of FIGS. 1A and 1B, in which a stabilizing cap 54 is added to maintain coiled member 38 in the contracted, wider configuration, and also to increase bulk and to prevent the introduction of food or other gastric products within interstice 48.

In one method of use, the gastric obstruction device 30 is introduced in a patient's stomach in the elongated, narrower configuration of FIG. 1A, with apron cover 40 oriented in the opposite direction to that shown in FIG. 1A, that is, to cover tether 36 while the free end of distal portion 46 is oriented proximally, in the direction of distal occluding member 34. When in this configuration, the gastric obstruction device 30 is disposed within a tube (not shown) and is caused to exit the tube with proximal end 52 first, followed by the rest of the gastric obstruction device 30. When the gastric obstruction device 30 has partially exited the tube (or alternatively, the tube has been retracted from the gastric obstruction device 30) so to leave apron cover 40 outside of the tube, the gastric obstruction device 30 is pulled inside the tube, but because apron cover 40 surrounds and wraps around the end of the tube, such a pulling of the gastric obstruction device 30 inwards into the tube, causing apron cover 40 to flip over and change orientation, so to wrap around coiled member 38. After such a flipping around of apron cover 40 has been achieved, the gastric obstruction device 30 is completely ejected from the tube and becomes disposed in the stomach. Alternatively, the gastric obstruction device 30 may be introduced into a patient's stomach with apron cover 40 already oriented proximally, making unnecessary the previously described flipping operation.

While the configuration of coiled member 38 makes it recoil and assume the contracted configuration, similar to that shown in FIG. 1B, the fully contracted, wider configuration of coiled member 38 is achieved and maintained as follows. A connecting member 56 is coupled (for example, by a first string) to a release member 58. A second string 60 is looped around the gastric obstruction device 30, running outside and along the gastric obstruction device 30 starting from a first free end, and then extending within connecting member 56 through lumen 66, and then (within a lumen or a tube) within turns 42, successively entering a lumen 62 in tether 36 and distal occluding member 34 (see also FIGS. 1D and 1E), and eventually exiting the gastric obstruction device 30 with a second free end.

After the gastric obstruction device 30 has been introduced in the stomach, a clinician can hold both ends of second string 60 and, by pulling on second string 60 while the gastric obstruction device 30 is constrained within the stomach, the clinician causes connecting member 56 to travel in the direction of mating cavity 64, shaped so to constrain connecting member 56 (for example, by interference fit) and to prevent connecting member 56 from being released. Therefore, coiled member 38 is locked into its contracted, wider condition on a permanent basis.

After the gastric obstruction device 30 has been shaped as described, second string 60 is removed by pulling on one free end and by having second string 60 slide through one or more lumens within the gastric obstruction device 30, eventually exiting the gastric obstruction device 30 entirely. The gastric obstruction device 30 is now free to move freely within the stomach, and the natural contractions of the stomach, in addition to any other movements of the patient's body, cause distal occluding member 34 to move into the pylorus, while the size of proximal occluding member 32 prevents it from moving into the pylorus and forces it to reside in the stomach. Therefore, distal occluding member 34 will eventually be disposed in the pylorus, and any inserts of a heavier weight will facilitate retention of distal occluding member 34 in the pylorus, while proximal occluding member 32 will act as an intermittent plug against the pyloric valve, because stomach contractions and other body movements will cause proximal occluding member 32 to move towards and away from the pyloric valve, acting as an intermittent plug and allowing the passage of some food from time to time.

Figures 2A, 2B, 2C:
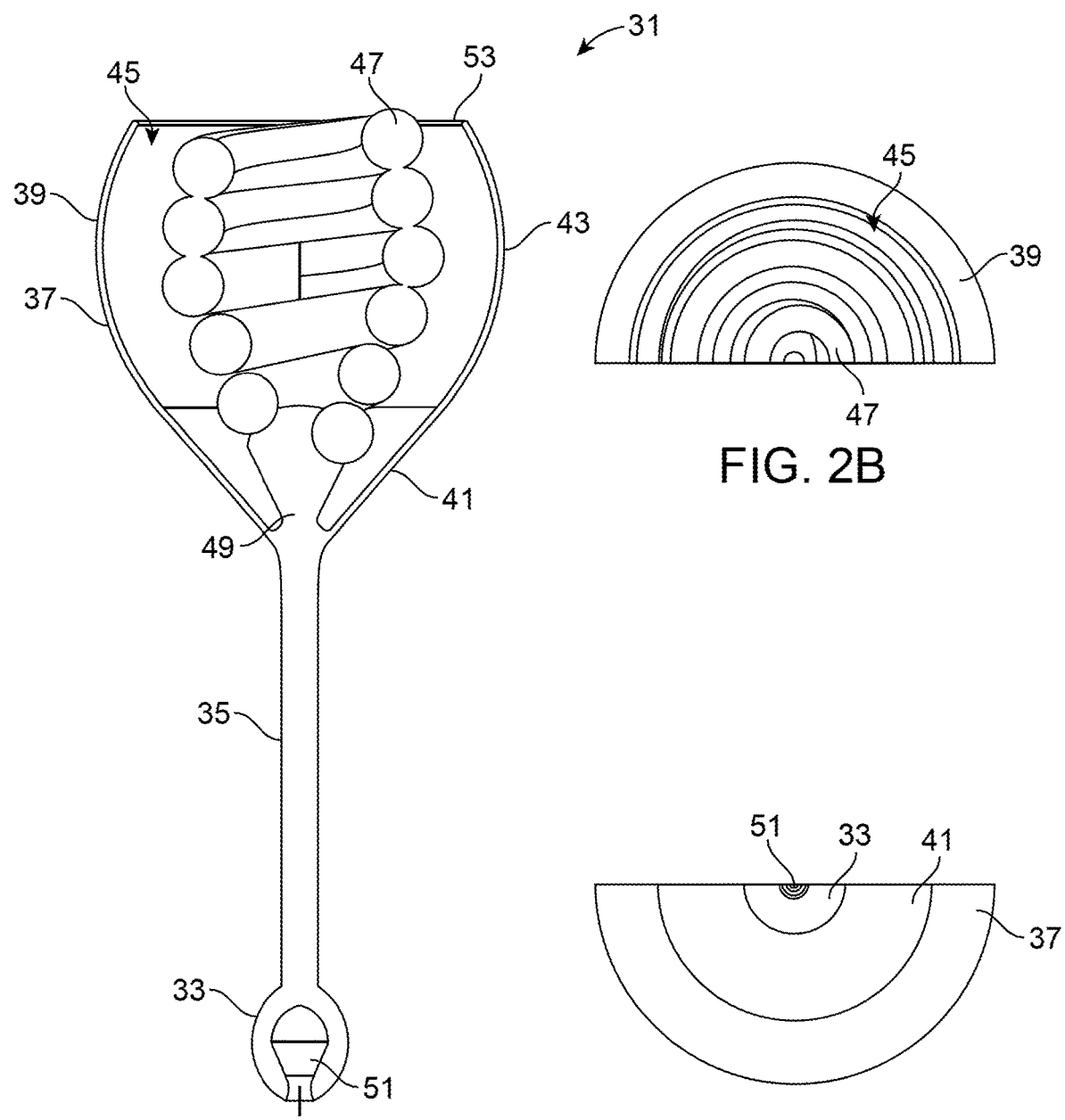
FIGS. 2A-2C illustrate respectively a cross-sectional side view and top and bottom end views of another embodiment.
Figure 2D:
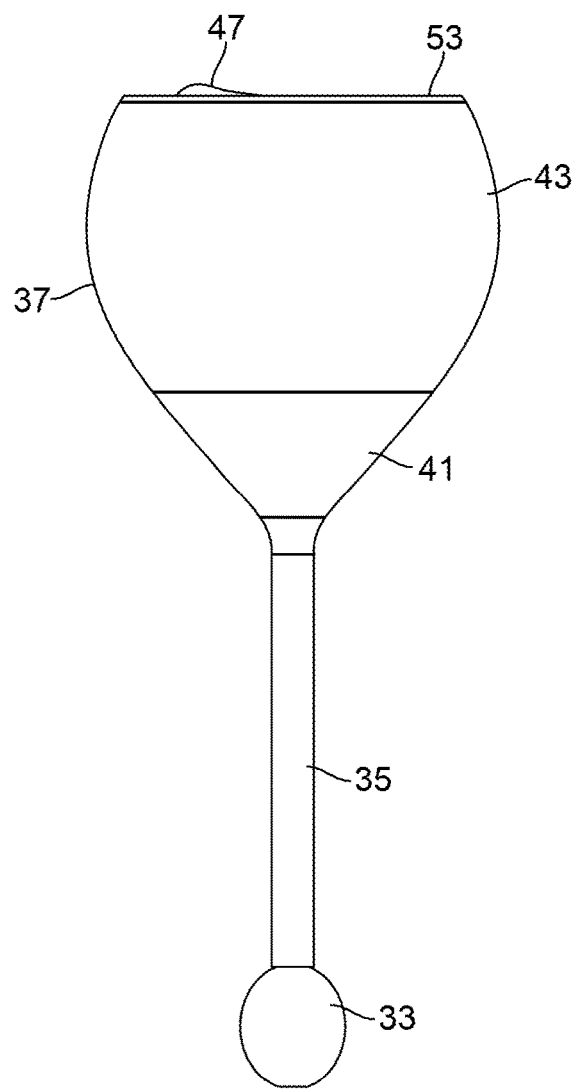
FIGS. 2D-2E illustrate respective side and cross-sectional perspective views of the embodiment of FIGS. 2A-2C.
Figure 2E:
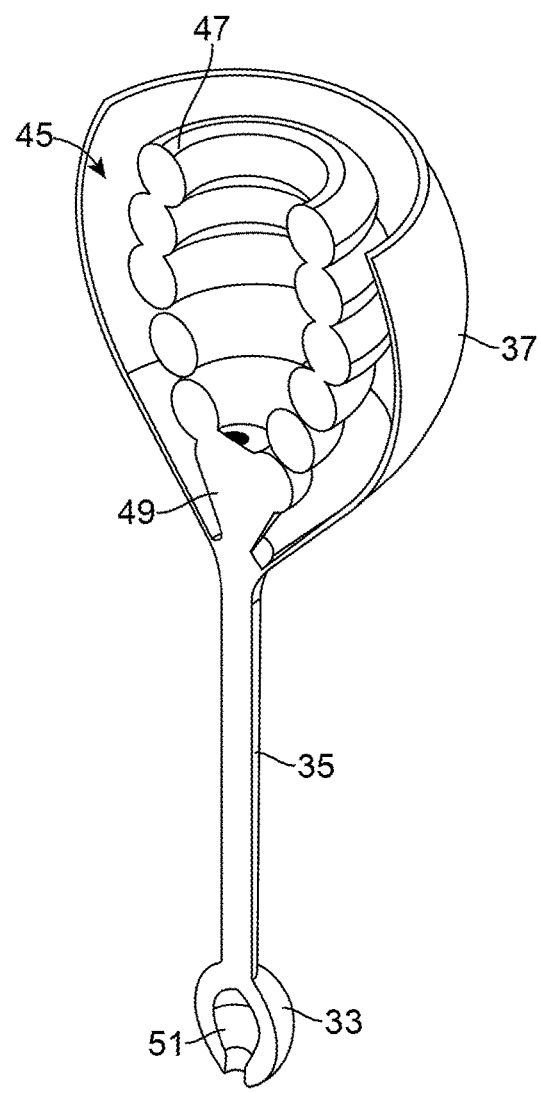

Another variation of a gastric obstruction device 31 is illustrated in the cross-sectional side view of FIG. 2A and the top and bottom end views, respectively, of FIGS. 2B and 2C. In this variation, the gastric obstruction device 31 may also include a distal occluding member 33 connected or attached via tether 35 to a proximal occluding member 37. As described above, proximal occluding member 37 may comprise an apron cover 39 which defines a curved or otherwise arcuate surface which tapers radially from tether 35 at a distal portion 41 (which typically contacts the stomach interior surface when in use) to a curved proximal portion 43 which has a relatively larger diameter and which may define a circumferential lip or edge 53 which is atraumatic to surrounding tissue. Apron cover 39 may define a channel or interstice 45 within which coiled member 47 may reside when coiled member 47 is in its contracted deployment configuration, as illustrated. With coiled member 47 contracted, apron cover 39 may be configured to entirely or at least partially encircle or enclose coiled member 47, as illustrated in FIGS. 2D and 2E which respectively show side and cross-sectional perspective views. Moreover, interstice 47 may be left open when in use in the patient body or an additional cap member or cover may be optionally attached to fully enclose apron cover 39 and coiled member 47 within, if so desired.

Coiled member 47 may be formed into a nested or wound structure having a plurality of turns and a distal end which is detachably coupled to the rest of the gastric obstruction device 31 at connecting portion 49. Because of its coiled or wound helical structure, the coiled member 47 may be extended in a low-profile configuration, as above, for delivery into the patient body and then allowed to compress or contract into its coiled structure which forms a diameter or cross-sectional area which is relatively larger than a diameter of distal occluding member 33 to inhibit or prevent the passage of proximal occluding member 37 through the pylorus when in use. As in the aforementioned embodiment, the coiled member 47 may be biased or configured to self-contract. Alternatively, a string member or other locking mechanism, as described herein, may be actuated to compress and/or lock the structure such that the expanded configuration is maintained and prevented from releasing and reconfiguring back into its low-profile configuration. Distal occluding member 33 may further define a lumen or channel 51 to facilitate the placement and/or positioning of the gastric obstruction device 31 within the patient body.

In yet another embodiment, the coiled member 47 may be fabricated as a separate component and attached or coupled within the apron cover 39 at a later time rather than forming the coiled member 47 as a continuous integral component. This particular embodiment allows for the size and shape of the proximal occluding member 37 to be varied and altered according to any patient-specific parameters and attached within a common apron cover.

Figure 3A:
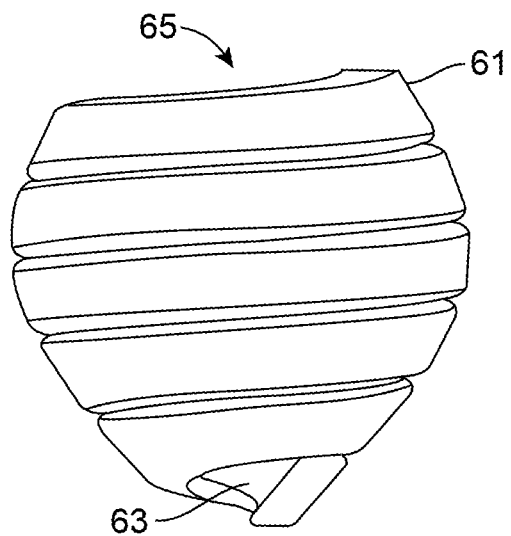
FIGS. 3A-3B illustrate side and cross-sectional side views, respectively, of yet another embodiment where the proximal occluding member is separately fabricated and removably attachable within an apron cover.
Figure 3B:
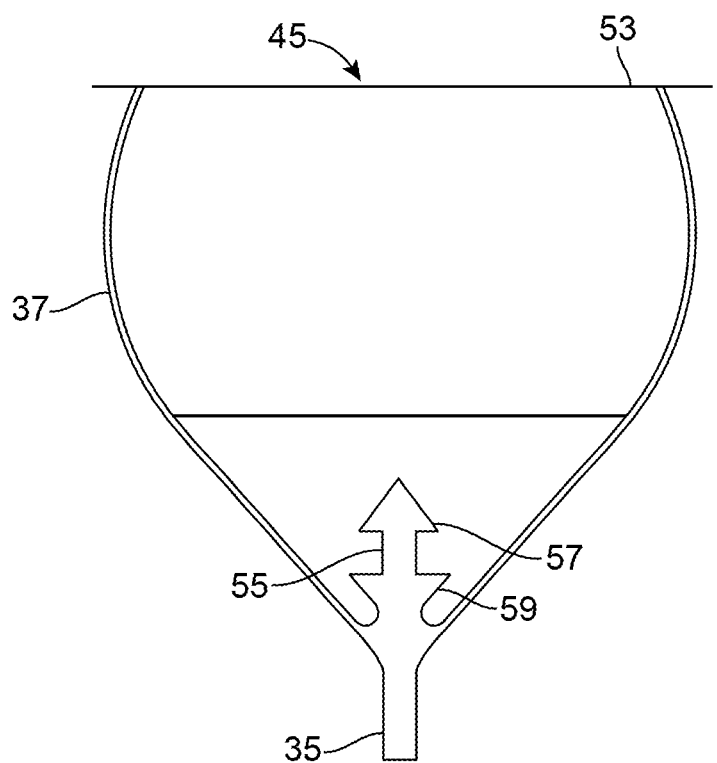

FIG. 3A illustrates a variation of a coiled member 61 (for example, any of coiled member 38 or 47) compressed into a wound or nested structure. The coiled member 61 can be formed in the wound or nested structure when deployed within a patient's stomach. FIG. 3B illustrates that the wound coiled member 61 can define a channel 65 and a receiving portion 63 when in its wound or nested configuration. As previously described, coiled member 61 may be advanced into the patient body in an extended low-profile elongated configuration and then collapsed into its expanded and optionally locked wound or nested configuration, either via actuation or by allowing for self-reconfiguration.

Because the coiled member 61 may form a receiving portion 63 in its collapsed configuration, portion 63 may be coupled to a complementary securement mechanism positioned within apron cover 39. In this example, the securement mechanism may be comprised of a connecting portion 55 which extends distally within apron cover 39. Connecting portion 55 may have a securement member 57, such as a tapered portion, and a stop member 59 which each limit the movement of portion 63 relative to connecting portion 55.

Figure 3C:
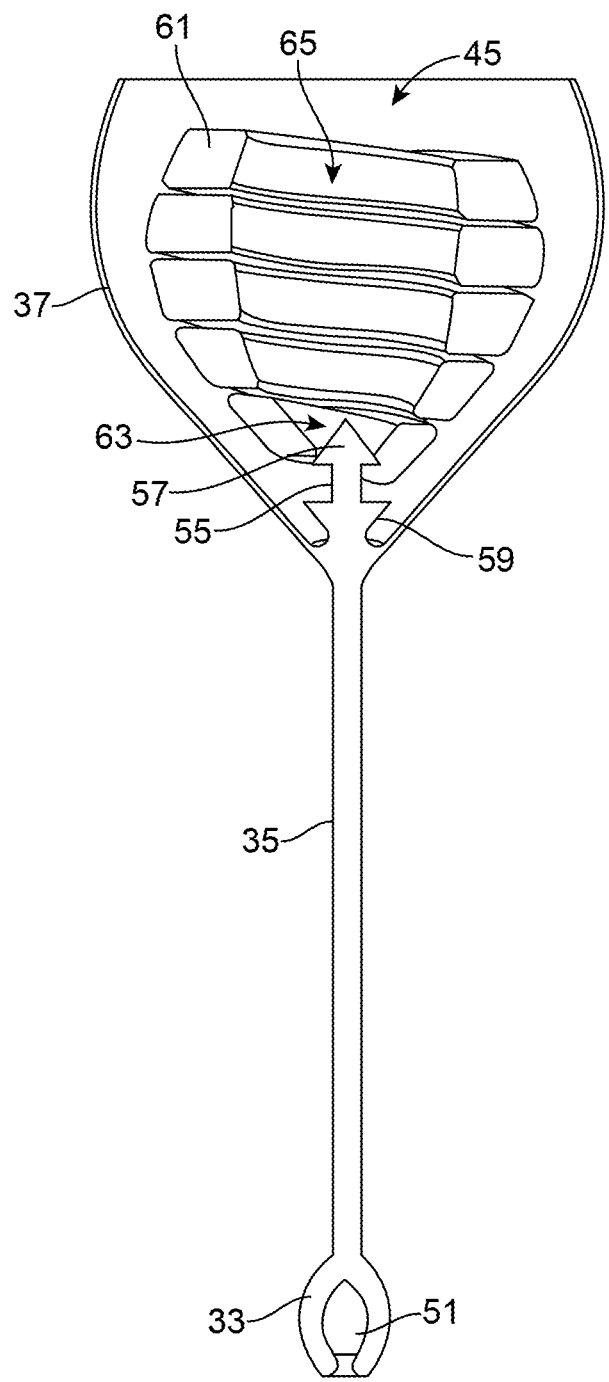
FIG. 3C illustrates a cross-sectional side view of an assembled device from FIGS. 3A and 3B.

As illustrated in the cross-sectional side view of FIG. 3C, coiled member 61 is shown in its nested and locked configuration while secured within interstice 45 and encircled by apron cover 39. As shown, securement member 57 may be advanced at least partially within channel 65 formed by the wound or partially wound or nested coiled member 61 to prevent the relative movement or release of coiled member 61 from connecting portion 55. The connecting portion 55 is illustrated as an example and is not intended to be limiting. Other known securement mechanisms may be utilized as practicable.

In these and other embodiments described herein, because the gastric obstruction device 31 may be introduced into the patient body in a minimally invasive manner, e.g., per-orally and through the esophagus into the patient's stomach, the gastric obstruction device 31 may be delivered in its low-profile configuration, e.g., where the coiled member 61 is in its uncoiled or unwound elongate configuration. Alternatively, the gastric obstruction device 31 may be delivered in a partially locked configuration. Once within the stomach, for instance, the gastric obstruction device 31 may be coiled or wound into its deployment configuration and the coiled member 61 may be affirmatively locked into position relative to the gastric obstruction device 31 such that its enlarged profile inhibits or prevents the passage of the gastric obstruction device 31 through the pylorus. In ensuring that the coiled member 61 is locked into its expanded configuration, various mechanisms may be utilized to confirm its securement.

One example includes having the string for locking the coiled member 61 be color-coded such that one portion of the string is of a different color (e.g., red) than the remainder of the string. As the string is tensioned to lock the coiled member 61, once the color-coded portion is exposed from the gastric obstruction device 31 the user may visually confirm that the coiled member 61 is locked into its deployment configuration. Alternatively, the amount of tension required to lock the gastric obstruction device 31 may be calibrated to increase to a preset level once the gastric obstruction device 31 is locked such that the user may confirm by tactile feedback that the gastric obstruction device 31 is indeed locked.

Other alternative mechanisms for locking confirmation or detection of the gastric obstruction device 31 may additionally include sensors incorporated within the gastric obstruction device 31. An example is illustrated in the cross-sectional side view of FIG. 1F, which shows sensor 67 positioned within the gastric obstruction device 31. Sensor 67 may incorporate any number of detection modalities, e.g., acoustic, ultrasonic, electrical, electromagnetic, optical (for instance, detecting changes in color, wavelength, frequency, etc.), chemical, etc. which may sense changes in the coiled member 61 from its nested or compacted deployment configuration or changes in the string tension, connecting member 56, or release member 58.

Figure 4A:
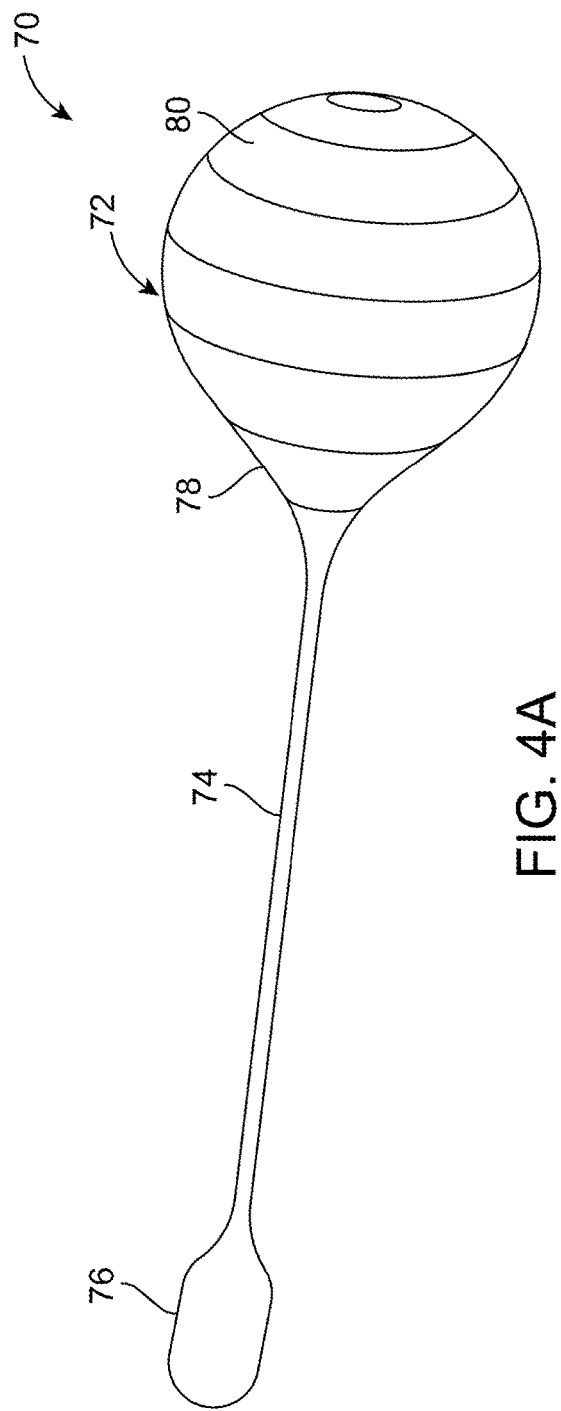
FIGS. 4A and 4B show perspective views of a gastric obstruction device having a proximal occluding member with a coiled member configured to compress from a narrow elongated configuration into an enlarged coiled and nested configuration and stretch from the enlarged coiled and nested configuration into the narrow elongated configuration.
Figure 4B:
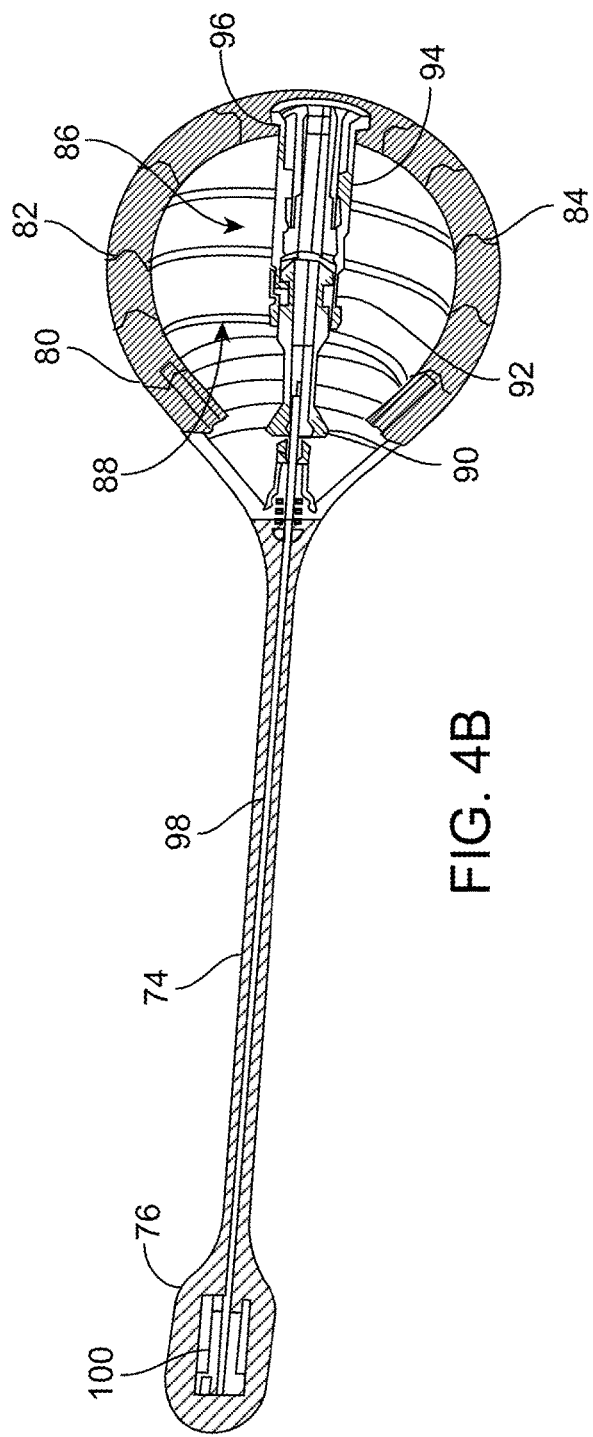

FIGS. 4A and 4B are perspective views of another variation of a gastric obstruction device 70 having a proximal occluding member 72 with a helical assembly reconfigurable from an elongated configuration into an enlarged, coiled, and nested configuration. The tether 74 may be seen extending from a compliant pyloric contact section 78 near a distal end of the proximal occluding member 72 and a distal occluding member 76 attached at a distal end of the tether 74. The compliant pyloric contact section 78 may be provided with a variable stiffness to be more benign to the contacted tissue (e.g., the pyloric valve and tissue surrounding the pyloric valve) and to further prevent trauma to the surrounding tissue. The compliant pyloric contact section 78 can be substantially conical-shaped, frusto-conical shaped, or tapered to converge or narrow in the direction of the distal occluding member 76. In this and any of the variations herein, various coatings may be applied to the gastric obstruction device 70, for example, for coefficient of friction, lubricity, enhanced biochemical durability, anti-microbial performance, etc.

FIG. 4B shows a cross-sectional side view of the coiled and locked gastric obstruction device 70 which in this variation illustrates the elongate coiled member 80 having a contoured profile 84. The profile 84 may define a projecting portion which may form a contact interface 82 when coiled into its nesting configuration with the adjacent coil although reversed contours may also be used to prevent the inward displacement of the nested loops. The contoured profile 84 may also enhance alignment of the structure during deployment as well. Furthermore, the edges of the coiled member 80 may also be radiused to reduce exposure of any edges to the gastric tissue. Once nested, the coiled member 80 may form a compacted shape which may form an enclosed space 88 within and which may be configured into a spherically-shaped structure, as shown. To maintain its compacted configuration, a central column 86 may extend through the center of the proximal occluding member 72 to lock the shape of the member 72. The central column 86 may be formed in part by a distal hub 90 which may be anchored or attached at a distal end of the proximal occluding member 72 and also optionally attached to the hub where the tether 74 is attached to the proximal occluding member 72. A proximal plug 94 may be seated 96 at a proximal end of the coiled member 80 and extend into a coupled attachment to the distal hub 90 which may be connected via, e.g., a collar 92 such as a directional C-clip, etc.

Optionally, a reinforcing member 98 such as a wire or suture length may be coupled to the distal hub 90 and extend through the tether 74 into attachment with the distal occluding member 76. Additionally, a distal weight 100 may also be optionally integrated in the distal occluding member 76 as well. The inclusion of a reinforcing member 98 may prevent the over-extension of the tether 74 during deployment and use. The member 98 may also function to prevent the detachment of the tether 74 or distal occluding member 76 in the unlikely event that the tether 74 fails.

Figure 5A:
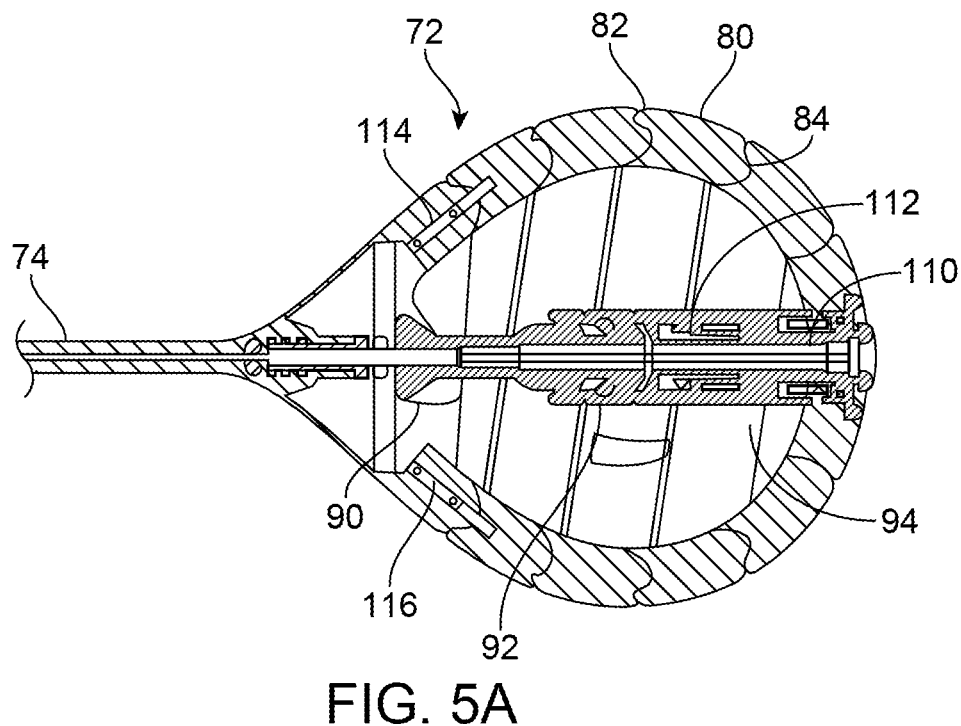
FIGS. 5A and 5B show cross-sectional side and perspective views of the proximal occluding member to illustrate detail features for locking the proximal occluding member into its enlarged and compacted configuration.
Figure 5B:
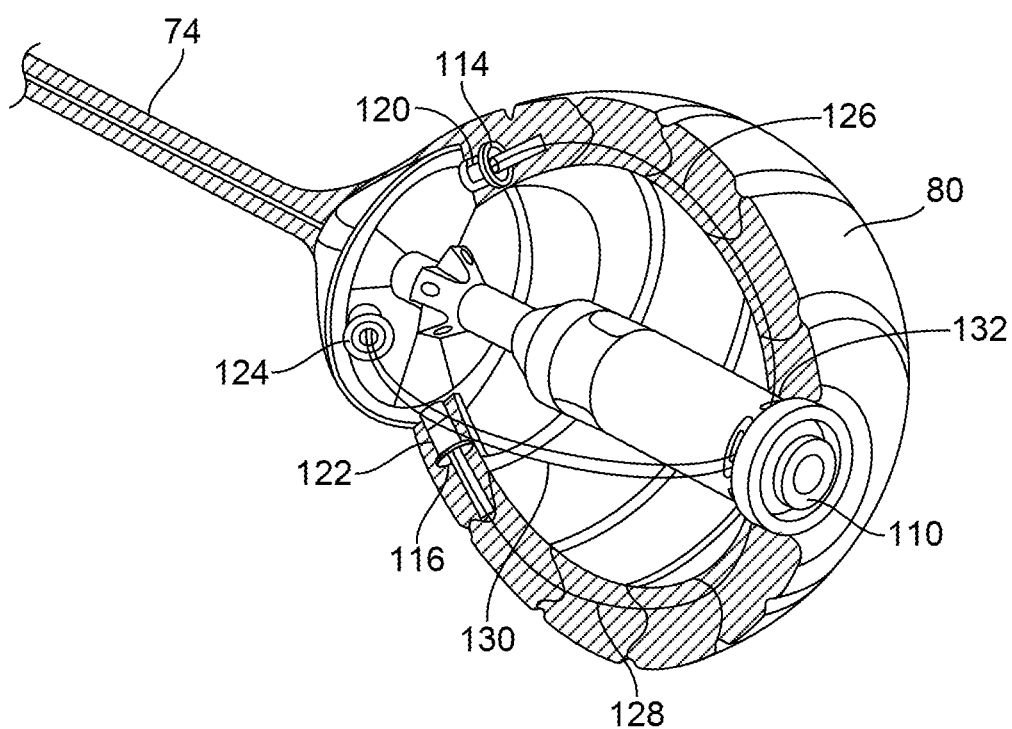

FIGS. 5A and 5B show cross-sectional side and perspective views of the proximal occluding member 72 to illustrate detail features for locking the proximal occluding member 72 into its enlarged and compacted configuration. As shown, the proximal plug 94 may include a release mechanism 110 which extends through a proximal end of the plug 94 and is secured via one or more release securement members 112 within the plug 94. The release mechanism 110 may be toggled proximally and distally relative to the plug 94 to selectively lock or unlock one or more tensioning wires which extend transversely through the coiled member 80. Moreover, the release mechanism 110 may be formed to have a rigid lip to facilitate its grasping by endoscopic tools when locking or unlocking the mechanism 110. Optionally, the release mechanism 110 may also integrated a valve, such as a duck-billed valve, to prevent solid matter from entering the internal space of the proximal occluding member 72. The collar 92 may also be seen coupling the distal hub 90 and the proximal plug 94 to one another. As the coiled member 80 configures into the enlarged configuration, the plug 94 may come into a mating engagement with the distal hub 90 which may then be joined by the collar 92 housed around the proximal plug 94.

To facilitate compression or translation of the coiled member 80 into its compacted configuration and to lock its enlarged configuration in a secure manner, one or more tension lines 226 (see FIG. 14), lock lines, or a combination thereof may extend through the coiled member 80 in a transverse direction. The tension lines 226 (see FIG. 14), lock lines, or a combination thereof may be formed of various wires, strings, or other high-strength force fibers. The terminal end of the coiled member 80 may integrate one or more tensioning wire pins 114, 116, as shown in FIG. 5A, to which one or more corresponding collets 120, 122, 124 are attached and which also have corresponding lock lines 126, 128, 130 extending from their respective pins. The lock lines 126, 128, 130 may be located uniformly about the circumference of the proximal occluding member 72 and extend transversely through respective lumens defined through the coiled member 80, as shown in FIG. 5B. Although three lock lines are shown, this is done for illustrative purposes and any number of lock lines may be utilized at uniform (e.g., four lock lines positioned at 90 degrees relative to one another about a circumference of the proximal occluding member 72) or arbitrary locations around the proximal occluding member 72. Moreover, multiple lock lines may further provide for locking redundancy such that if one lock line were to fail, the proximal occluding member 72 may still retain its enlarged structure.

With the lock lines extending through the coiled member, they may pass and loop through corresponding openings 132 located near or at the proximal end of the proximal plug 94. While the lock lines are passed through the proximal occluding member 72 and are used to reconfigure and lock the gastric obstruction device 70 into its deployed configuration, the tension lines 226 (see FIG. 14) may be coupled to the lock lines and may extend from the gastric obstruction device 70 and through the control assembly. Moreover, the tension lines 226 may lead either to the proximal end of the coiled member 80 (in which case the entire coiled member may be delivered into the stomach before reconfiguration) or the tension lines 226 may lead through the middle of the coiled member 80 and then outward in a retrograde fashion through the walls of the coiled member which enables reconfiguration of the coiled member as it emerges from the delivery tube in a much more controlled process. The remaining terminal ends of each of the tension lines 226 may be passed externally of the gastric obstruction device 70 as well as externally of the patient body when in use to facilitate the tensioning and securement of the tension lines 226 when collapsing the proximal occluding member 72. With the looped lock lines passing through opening 132, the release mechanism 110 may be selectively collapsed into the proximal plug 94 to lock the tensioning in the lock lines which may maintain the compacted configuration of the proximal occluding member 72. Pulling of the release mechanism 110 may accordingly release the lock lines and allow for the unraveling of the proximal occluding member 72, e.g., during removal of the gastric obstruction device 70 from the patient's stomach.

To facilitate the tensioning of the lock lines, they may be engaged through the respective collets to allow for unidirectional passage of the lock lines. Thus, as the lock lines are tensioned through the collets, they may be pulled in only a tensioning direction to prevent or inhibit the unraveling of the proximal occluding member 72. Additionally, the collets or pins may be optionally radio-opaque to facilitate visualization of the gastric obstruction device 70 through, e.g., fluoroscopic visualization, to provide for confirmation of the locked status of the proximal occluding member 72.

In another variation, the tension lines 226 can be coupled to lock lines (e.g., lock lines 126, 128, 130, etc.) which are used to lock the coiled member 80 in its compressed, wound, and nested configuration. The tension lines can be used to pull the coiled member 80 through the delivery tube 184 and out of the delivery tube 184 into a device cover 142 or device skin. The tension lines 226 can extend from a delivery assembly 170 (see FIGS. 10, 12G, 13A, and 27) through the turns of the coiled member 80 of the gastric obstruction device 70, and back into the delivery assembly 170 through a lumen of a control tube 228 (see FIGS. 18A, 18B, 18C, 18D, 22, 29A, and 29B). The tension lines 226 can be detached or otherwise separated from the lock lines. The tension lines 226 can then be cut and removed from the gastric obstruction device 70 (e.g., through the control tube 228) when the gastric obstruction device 70 is locked by the locked lines in the nested or wound configuration.

FIGS. 6A and 6B show perspective and cross-sectional perspective views, respectively, of another variation of the gastric obstruction device 70 having a device skin or device cover 142. In this variation, the device cover 142 may enclose the coiled member 80 partially or completely such that the surface presented to the surrounding tissue remains completely smooth and uniform. The device cover 142 may approximate the enlarged shape of the proximal occluding member 72 such that the coiled member 80 may be formed entirely within the device cover 142 itself, as described herein. Once the coiled member 80 has been formed within, a tissue interface 144 may be positioned by the terminal end of the coiled member 80 so as to present a smooth surface against the surrounding tissue. FIG. 6A also illustrates that the device cover 142 of the gastric obstruction device 70 can have a substantially conical-shaped or tapered compliant pyloric contact section 78.

As shown in the cross-sectional perspective view of FIG. 6B, a strain relief hub section 146 may be incorporated between the device cover 142 and tether 74 so as to prevent the excessive strain at the connection point due to the softened structure. The strain relief hub section 146 may be internally expandable such that it is rotationally secure. It may also be provided as a single-molded part that can be expanded by compression. An attachment collar 148, in an alternative variation, may extend into the receiving space 152 defined within the device cover 142 and the proximal plug 94 may be detached from the distal hub 90 such that the central column is discontinuous. The attachment collar 148 may be configured to receive the pins at the terminal ends of the lock lines to lock the proximal occluding member 72 in its configuration and may also join the member 72 to the device cover 142. Having a decoupled column may provide for additional flexibility to the proximal occluding member 72 which may conform or flex to a greater extent. With the device cover 142 deployed first, the coiled member 80 may be introduced in its elongate configuration directly through cover opening 150 and into the receiving space 152 where it may coil into its nested and collapsed configuration, as described herein.

Based on the foregoing, the gastric obstruction device (including any of the gastric obstruction devices 30, 31, or 70, and variations thereof) assists in the treatment of obesity by limiting the passage of food from the stomach into the intestine, and at the same time by reducing the intake of food by the patient due to the sense of fullness generated by the retention of food in the stomach for a longer time and also by to the presence of the gastric obstruction device in the stomach.

Figure 7:
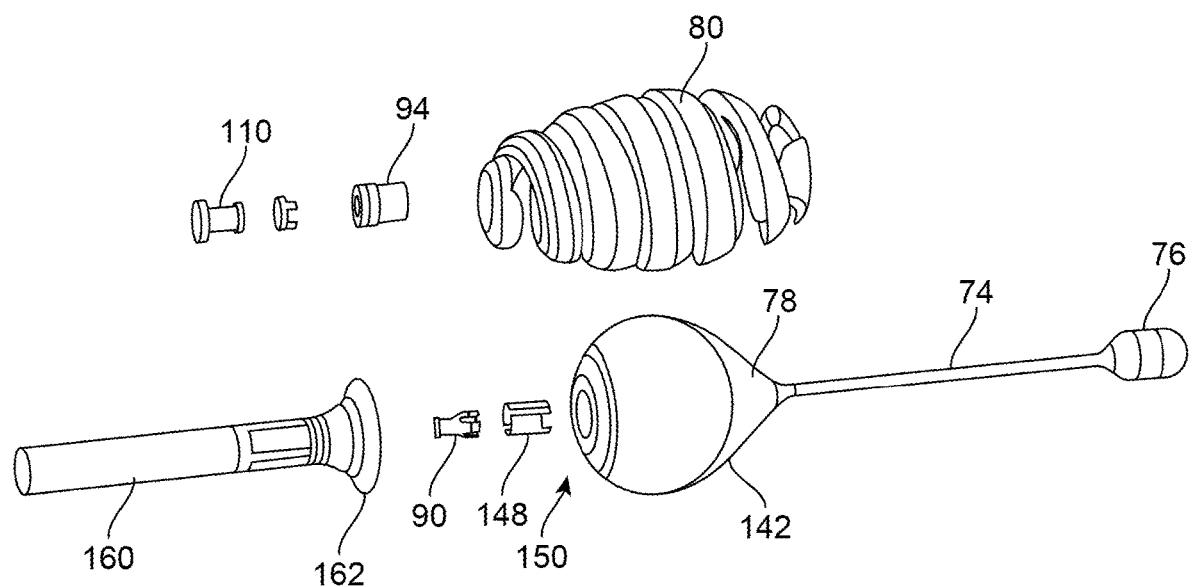
FIG. 7 shows a perspective assembly view of the various components which may form the covered obstructing assembly.
Figure 8:
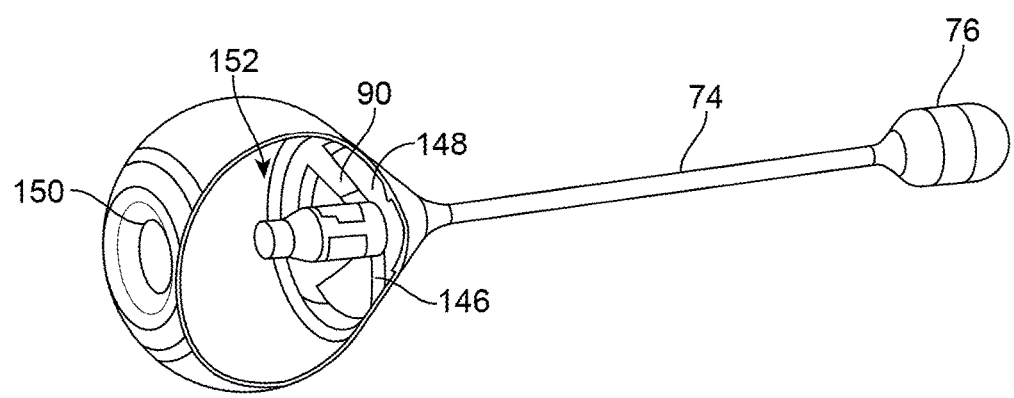
FIG. 8 shows a partial cross-sectional perspective view of the device cover or skin having a distal hub and attachment collar within the receiving space.

FIG. 7 shows a perspective assembly view of the various components which may form the covered embodiment. As shown, the device cover 142 may incorporate the distal hub 90 and attachment collar 148 within the receiving space 152, as shown in the partial cross-section perspective view of FIG. 8. The coiled member 80 may be introduced into the receiving space 152 through opening 150 as a component separate from the device cover 142. As previously described, the proximal plug 94 and release mechanism 110 may also be integrated with the coiled member 80. Additionally, a delivery tube 160 having a tapered device cover interface 162 may be provided for attachment to the opening 150. The delivery tube 160 may provide an access passage for the introduction of the coiled member 80 in its elongate form into the device cover 142. FIG. 7 also illustrates that the device cover 142 can have a substantially conical-shaped or tapered compliant pyloric contact section 78.

Figure 9A:
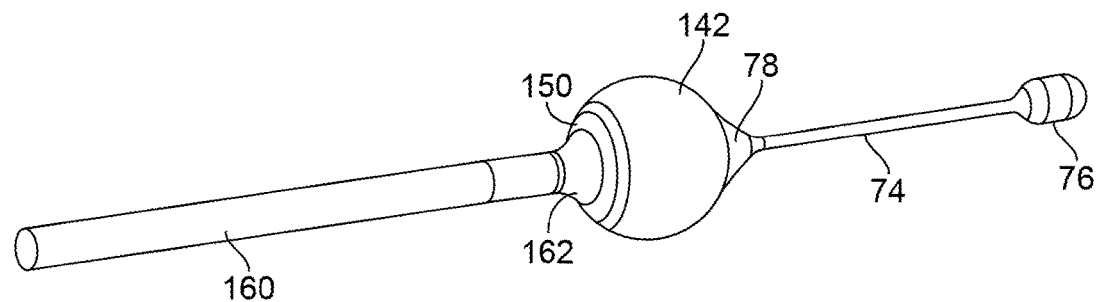
FIGS. 9A-9C illustrate partial cross-sectional perspective views of an example showing how the coiled member may be deployed within the cover or skin.
Figure 9B:
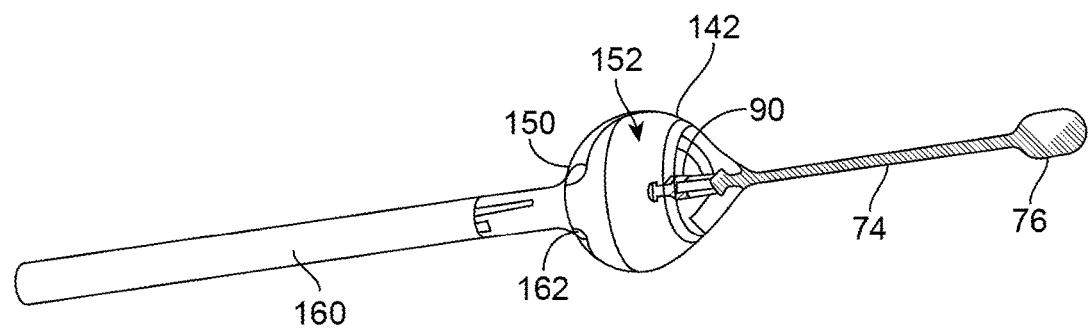
Figure 9C:
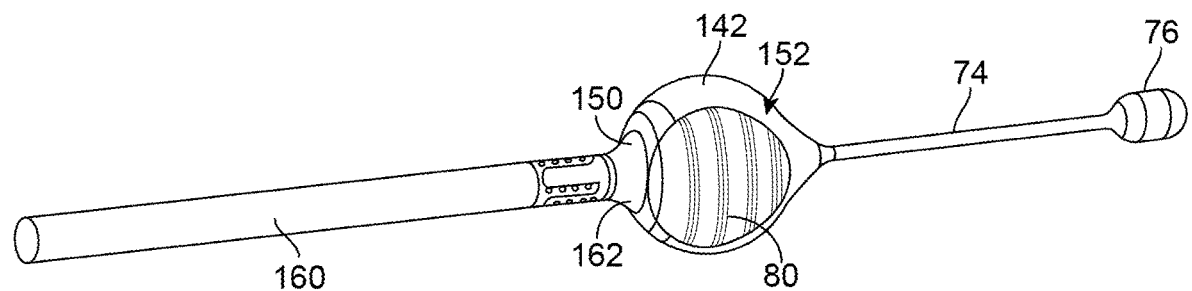

FIGS. 9A to 9C illustrate partial cross-sectional perspective views of an example showing how the coiled member 80 may be deployed. With the device cover 142 attached temporarily to the device cover interface 162 at opening 150, as shown in FIG. 9A, the device cover 142 may be positioned within the stomach. FIG. 9B illustrates how the device cover 142 may be devoid of the coiled member 80. As shown in FIG. 9C, the coiled member 80 may then be introduced through the delivery tube 160 and into the receiving space 152 where it may then coil into its nested and compacted configuration. Once complete, the device cover interface 162 may be pulled from the opening 150 to detach itself and the tissue interface 144 and release mechanism 110 may obstruct or plug the device cover opening 150. As shown in FIGS. 9A to 9C, the device cover 142 can have a substantially conical-shaped or tapered compliant pyloric contact section 78.

Figure 10:
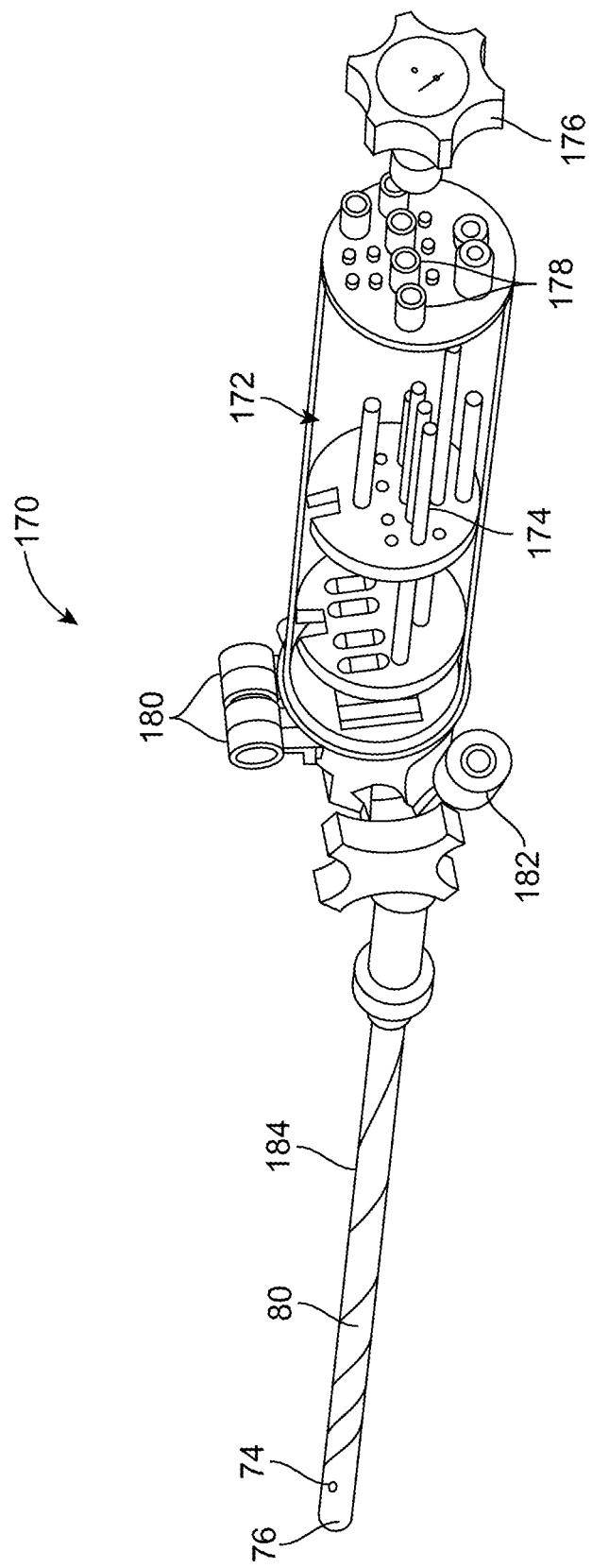
FIG. 10 shows one variation of a delivery assembly.

In delivering and deploying the gastric obstruction device (any of the gastric obstruction devices 30, 31, or 70) into the stomach, one variation of a delivery assembly 170 is shown in the perspective view of FIG. 10. In this example, the delivery assembly 170 comprises a tensioning control assembly 172 attached to a delivery tube 184 extending from the control assembly 172. The coiled member 80 may be loaded within the delivery tube 184 in its elongated configuration with the tether 74 and distal occluding member 76 positioned within the delivery tube 184 distal to the coiled member 80. The tension lines 226 (see FIG. 14) may pass through the coiled member 80 within the delivery tube 184 and extend proximally through the delivery tube 184 and into the control assembly 172. Each of the tension lines 226 may be routed to a corresponding tensioning spring 174 which may provide a continuous or intermittent tensioning force of variable magnitude upon the tension lines 226 which may help to prevent the tension lines 226 from tangling and which may also facilitate the tensioning of the tension lines 226 when forming the coiled member 80 into its compacted shape.

Each of the tension lines 226 (see FIG. 14) may also be attached to a corresponding tension control interface 178 which may tighten each of the tension lines 226 individually or simultaneously, e.g., via an actuatable loop tensioner 176. Each of the tension lines 226 may be further routed through the control assembly 172 and into communication with a corresponding tensioning wire access handle 180. Once the proximal occluding member 72 has been sufficiently nested and compacted, one or more of the wire access handles 180 may be pulled to expose the tension lines 226 which may then be cut and/or removed from the assembly and patient. An optional insufflation port 182 coupled to the delivery tube 184 may also be provided, e.g., for insufflating the stomach or body lumen prior to or during delivery of the obstructing member.

In another variation, the tension lines 226 can be coupled to lock lines (e.g., lock lines 126, 128, 130, etc.) which are used to lock the coiled member 80 in its compressed, wound, and nested configuration. The tension lines can be used to pull the coiled member 80 through the delivery tube 184 and out of the delivery tube 184 into a device cover 142 or device skin. The tension lines 226 can extend from a delivery assembly 170 (see FIGS. 10, 12G, 13A, and 27) through the turns of the coiled member 80 of the gastric obstruction device 70, and back into the delivery assembly 170 through a lumen of a control tube 228 (see FIGS. 18A, 18B, 18C, 18D, 22, 29A, and 29B). The tension lines 226 can be detached or otherwise separated from the lock lines. The tension lines 226 can then be cut and removed from the gastric obstruction device 70 (e.g., through the control tube 228) when the gastric obstruction device 70 is locked by the locked lines in the nested or wound configuration.

Figure 11A:
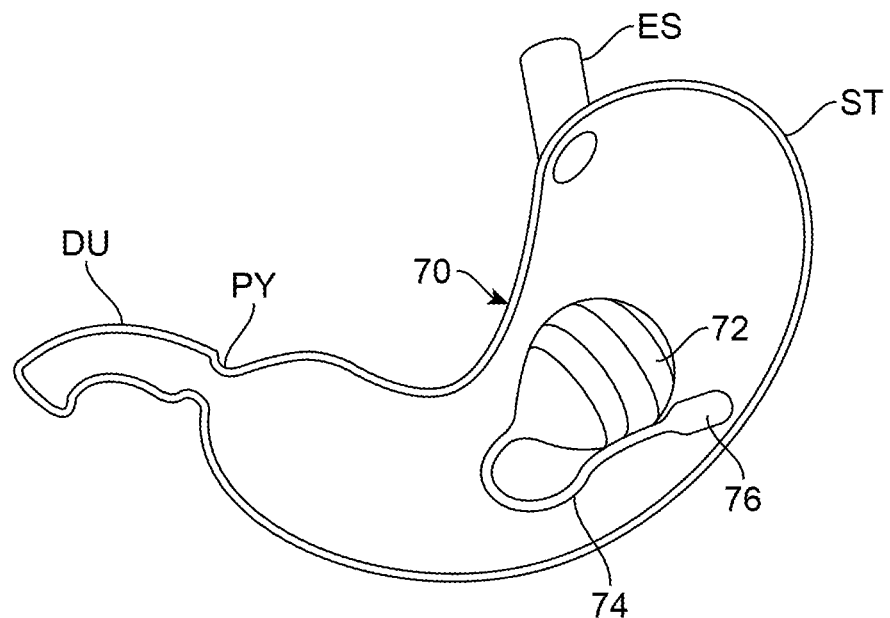
FIGS. 11A and 11B show partial cross-sectional views of the device placed within the stomach.
Figure 11B:
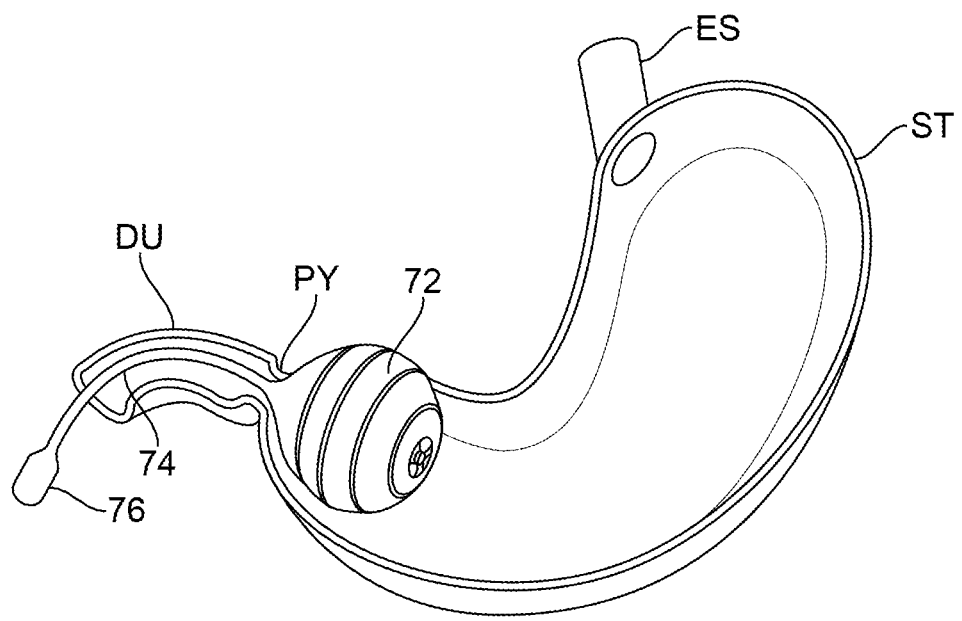

When deployed, the gastric obstruction device 70 may be placed within the stomach ST of a patient, as shown in the partial cross-sectional view of FIG. 11A. The esophagus ES, pylorus PY, and duodenum DU are also illustrated for reference. With the proximal occluding member 72 in its enlarged and nested configuration, the gastric obstruction device 70 may lie within the stomach ST. Once the patient has ingested some food or liquid, the stomach ST may begin to contract such that the distal occluding member 76 is moved through the stomach ST towards the pylorus PY. Because the distal occluding member 76 is sized for passage through the pylorus PY, the distal occluding member 76 may pass through to become positioned within the duodenum DU of the patient. However, because of the enlarged configuration, the proximal occluding member 72 may remain within the stomach ST and the compliant pyloric contact section 78 of the proximal occluding member 72 can intermittently cover the pylorus PY, as shown in FIG. 11B. As the stomach continues to contract, the proximal occluding member 72 may begin to intermittently obstruct and expose the pylorus PY allowing food and/or liquid to pass from the stomach at a slower rate thus forcing the patient to feel full for longer periods of time. Once the stomach has been completely emptied, the gastric obstruction device 70 may be allowed to then reposition itself within the stomach ST.

Figure 12A:
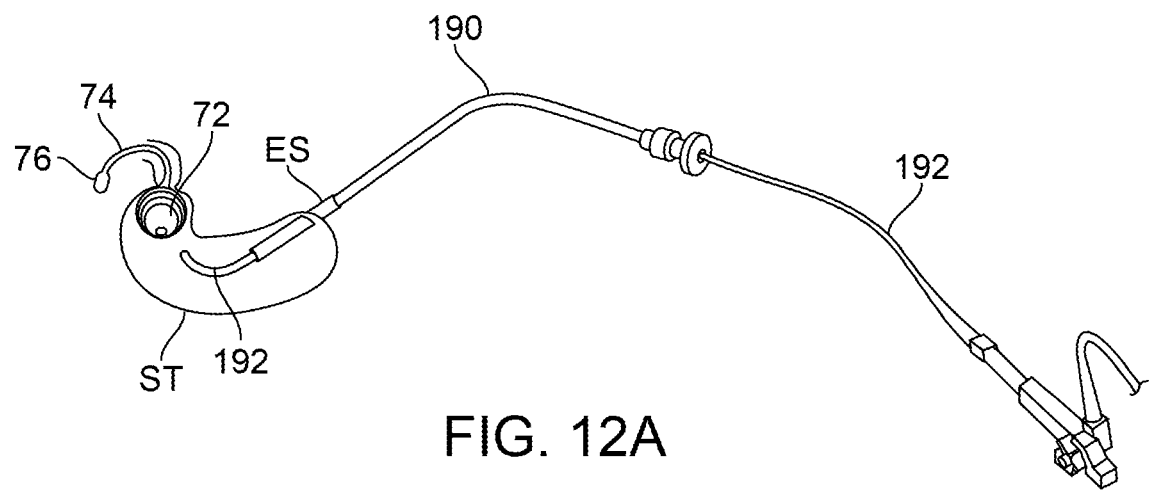
FIG. 12A shows a perspective view of an optional access tube positioned through the esophagus for removal of the device from a patient.
Figure 12B:
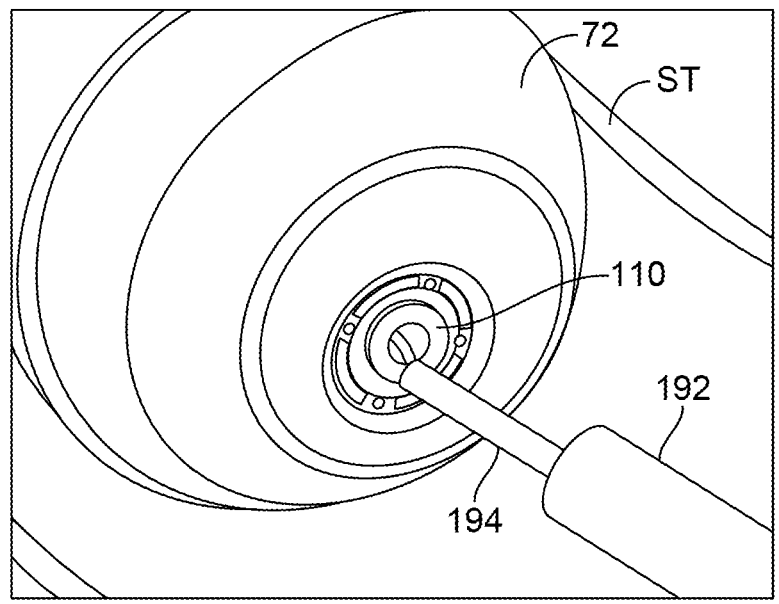
FIG. 12B shows a perspective view of a grasper brought into contact with a release mechanism.
Figure 12C:
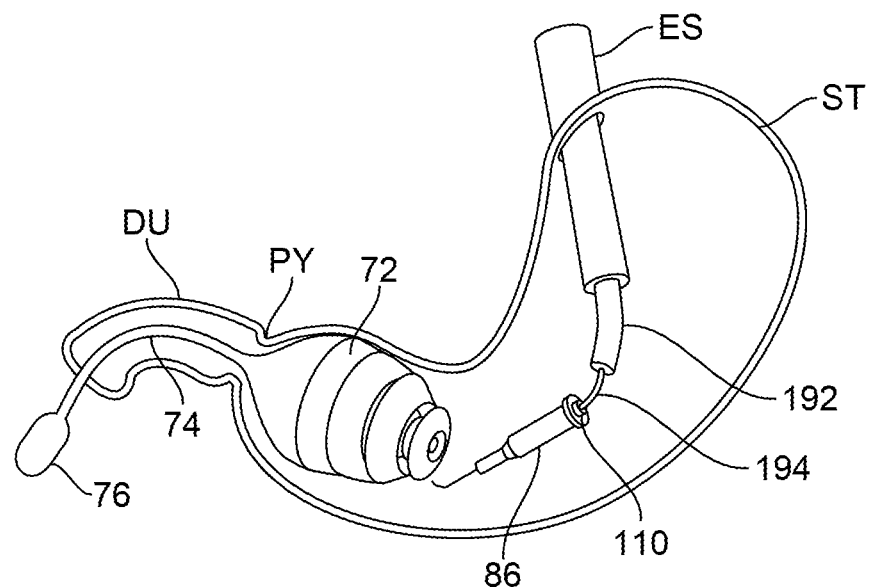
FIGS. 12C and 12D show an example of the proximal occluding member being unlocked and removed from a stomach in its elongate configuration.
Figure 12D:
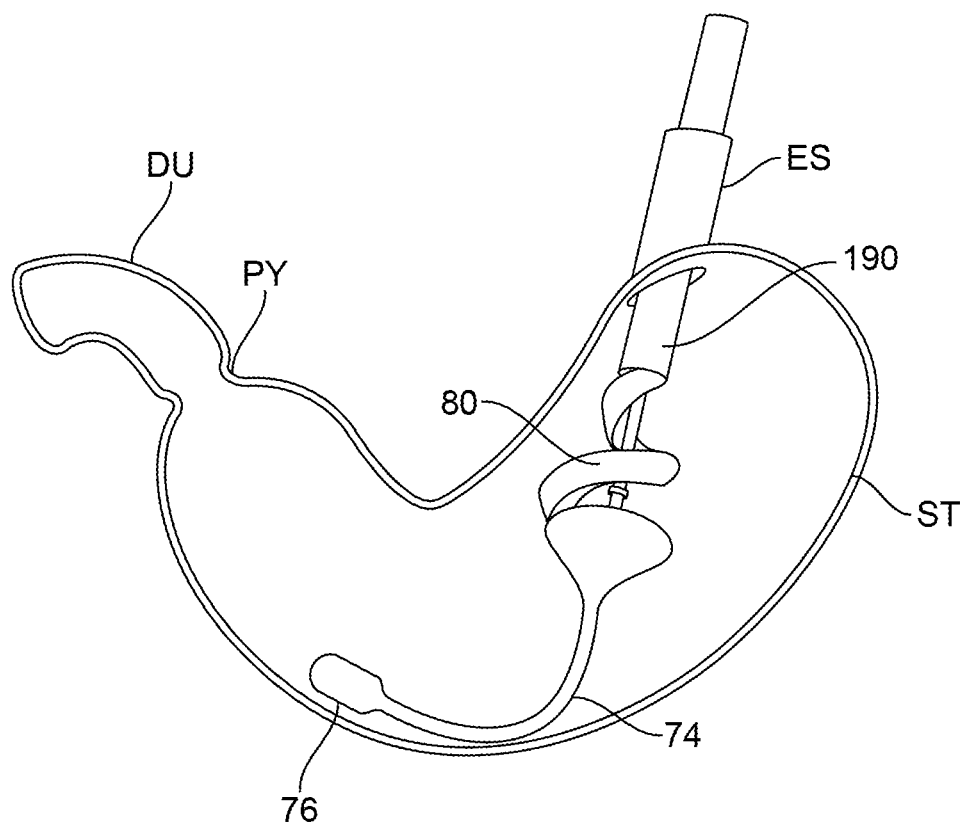

In the event that the gastric obstruction device 70 is to be removed from the patient, the gastric obstruction device 70 may be collapsed within the stomach ST and removed back through the esophagus ES in its elongate configuration. One example is shown in the perspective view of FIG. 12A which illustrates how an optional access sheath 190 may be positioned through the esophagus ES and an endoscope 192 or other instrument having, e.g., a grasper 194, may be passed through the access sheath 190 and into proximity to the proximal occluding member 72. The grasper 194 may be brought into contact with the release mechanism 110, as shown in the perspective view of FIG. 12B, which may then be pulled to unlock the proximal occluding member 72. The entire central column 86 may be removed from the proximal occluding member 72, as shown in FIG. 12C, and removed from the stomach ST. With the proximal occluding member 72 released, the coiled member 80 may be pulled through the access sheath 190 and through the esophagus ES in its collapsed and elongate profile, as shown in FIG. 12D.

Figure 12E:
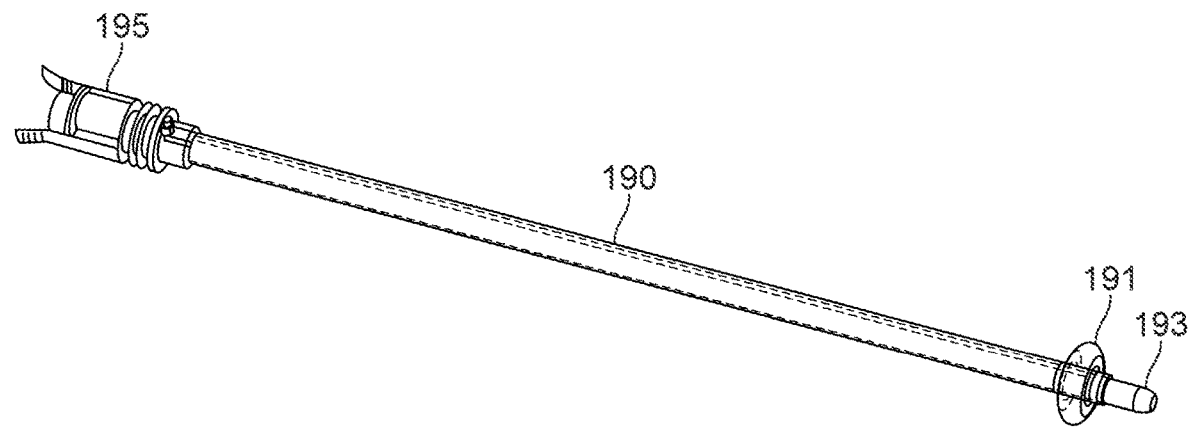
FIGS. 12E and 12F show an example of a transoral access sheath which is configured to be inserted into and retained within the stomach.
Figure 12F:
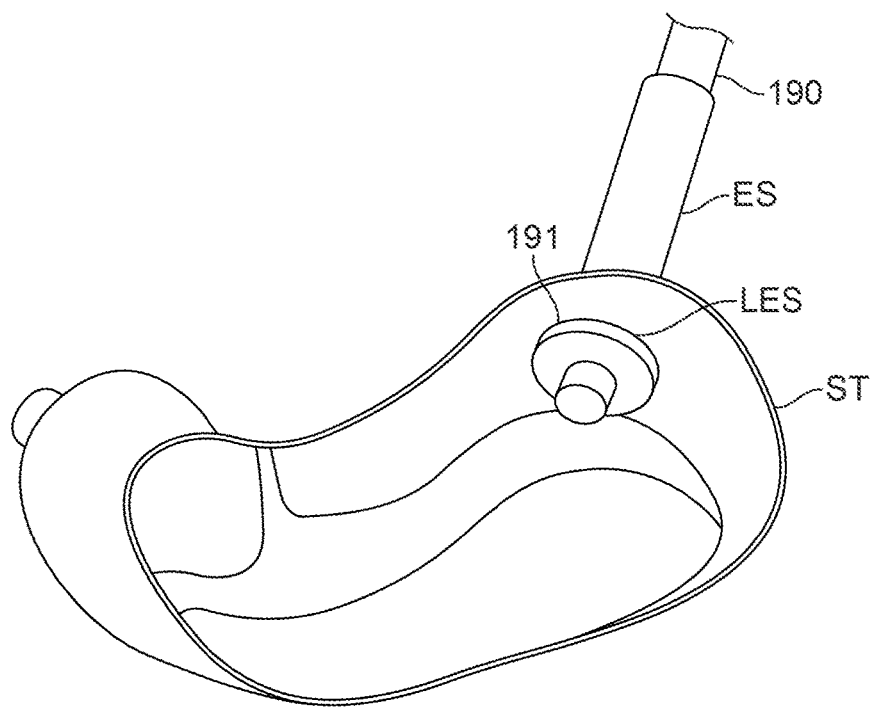

In yet another variation of devices for facilitating delivery and deployment, FIG. 12E shows a perspective view of another variation for an access sheath 190 and FIG. 12F shows an illustrative view of the transoral access channel positioned at least partially within and anchored against, e.g., the gastroesophageal sphincter (LES) of the stomach ST. An access sheath 190 having a sufficient diameter (e.g., approximately 19 mm in diameter) to pass the delivery assembly 170 may terminate at its proximal end in a connector 195 which may be configured to securely attach onto the delivery device, e.g., via a pair of engagement clips or other securement mechanism, to keep an obturator 193 registered with the access sheath 190 during introduction with an endoscope 192. The access sheath 190 may also function as a tissue retractor or anchoring device to provide clearance as well as a stable access point for entrance into the stomach ST through the esophagus ES.

An endoscope 192 such as a normal gastroscope may be used to advance the access sheath 190 into the stomach ST as with an overtube 202. Once in place, the endoscope 192 and obturator 193 may be optionally removed leaving the access sheath 190 in place for a delivery conduit. At the distal end of the access sheath 190 is an expanding feature which can be activated by the user once the distal end of the access sheath 190 is inside the stomach ST. The expanding feature can be an axial toroidal balloon 191 or any other expandable feature which provides an atraumatic surface for presentation against the stomach tissue such as against the LES. The balloon 191 is intended to be pulled in traction to bear on its proximal surface. The balloon 191 may also be inflated through a side lumen tube using, e.g., a syringe, pump, or any other inflation mechanism. Moreover, the balloon 191 may be filled with air or liquid or both. Once inflated, the access sheath 190 may be pulled until tactile resistance indicates it is seated at the LES. The cushioning nature of the balloon 191 provides an atraumatic interface with the tissue. The inflated balloon 191 may also help to maintain the distal opening of the access sheath 190 within the stomach ST. When the procedure is completed, the balloon 191 may be deflated and the access sheath 190 withdrawn.

The balloon 191 may also provide some additional benefits. First, when inflated and retracted, it defines a maximum volume space for construction of the gastric obstruction device 70 by anchoring the construction site close to the entry of the LES. Second, inflation of the balloon 191 structurally elevates the sheath tube up and away from the posterior wall of the stomach ST providing free space for construction of the gastric obstruction device 70. Additionally, retraction of the balloon 191 aids in sealing of the stomach ST for insufflation. The sleeve material of the access sheath 190 may be constructed of various biocompatible materials, e.g., a very thin wall PTFE tube, which may provide a relatively larger crossing section profile for delivery and may also minimize the tube kink strength when the sheath passes through any bends. This may also minimize the resistance to introduction and delivery passage of the gastric obstruction device 70. PTFE in particular may be used because it has a very low frictional coefficient providing low advancement resistance to the delivery assembly 170. The balloon 191 may be mounted to a rigid thin walled cuff which allows for mechanical connection of the PTFE sleeve and a structural non-collapsing platform for mounting the balloon 191.

Figure 12G:
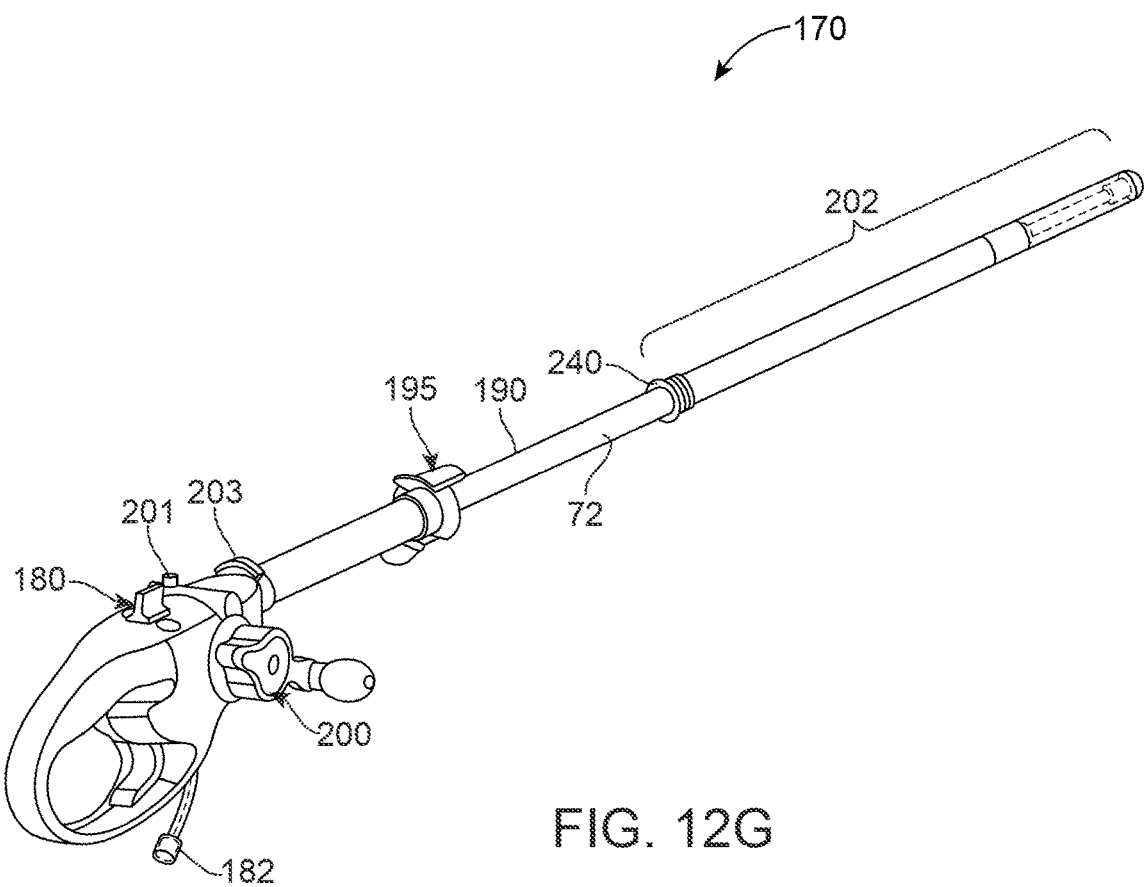
FIG. 12G shows one example of how the transoral access sheath interfaces with the delivery system.
Figure 12H:
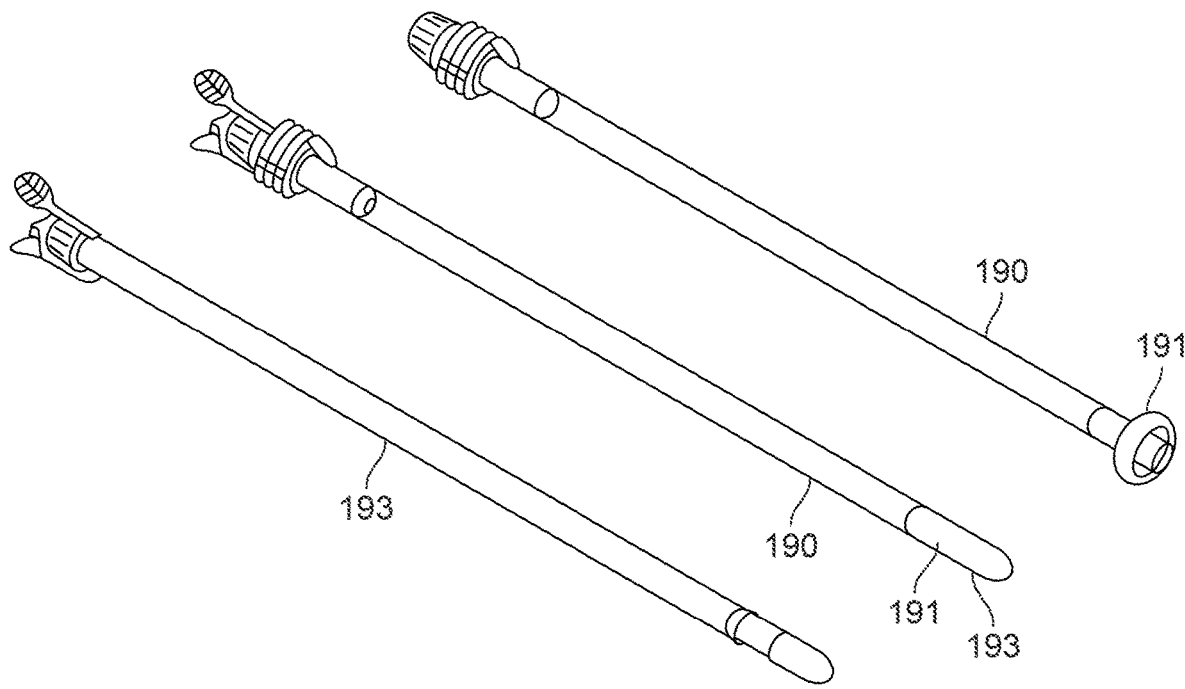
FIG. 12H shows examples of an obturator, an obturator combined with an access sheath having a deflated balloon, and an access sheath having an inflated balloon.

FIG. 12G illustrates a perspective view of the sheath 190 and connector 195 secured to the delivery assembly 170. The overtube or introducer sleeve 202 at the distal end of the delivery assembly 170 allows for easy insertion of the shaft into the access sheath 190 which may slide proximally over the delivery assembly 170. The hub 240 of the overtube 202 may seat inside the handle of the access sheath 190 when the delivery assembly 170 is mated to the proximal end of the access sheath 190 via the access sheath connector 195. The insufflation port 182 may also be seen extending from the handle. A deployment progress indicator 201 may also be integrated into the delivery assembly 170 as well. Additionally, a delivery tube disconnect 203 mechanism, e.g., U-clip, may be integrated to allow for the detachment of the delivery tube from the assembly. FIG. 12H illustrates perspective views of examples of an obturator 193, an obturator 193 inserted within or along an access sheath 190 having a deflated balloon 191, and an access sheath 190 having an inflated balloon 191.

Figure 13A:
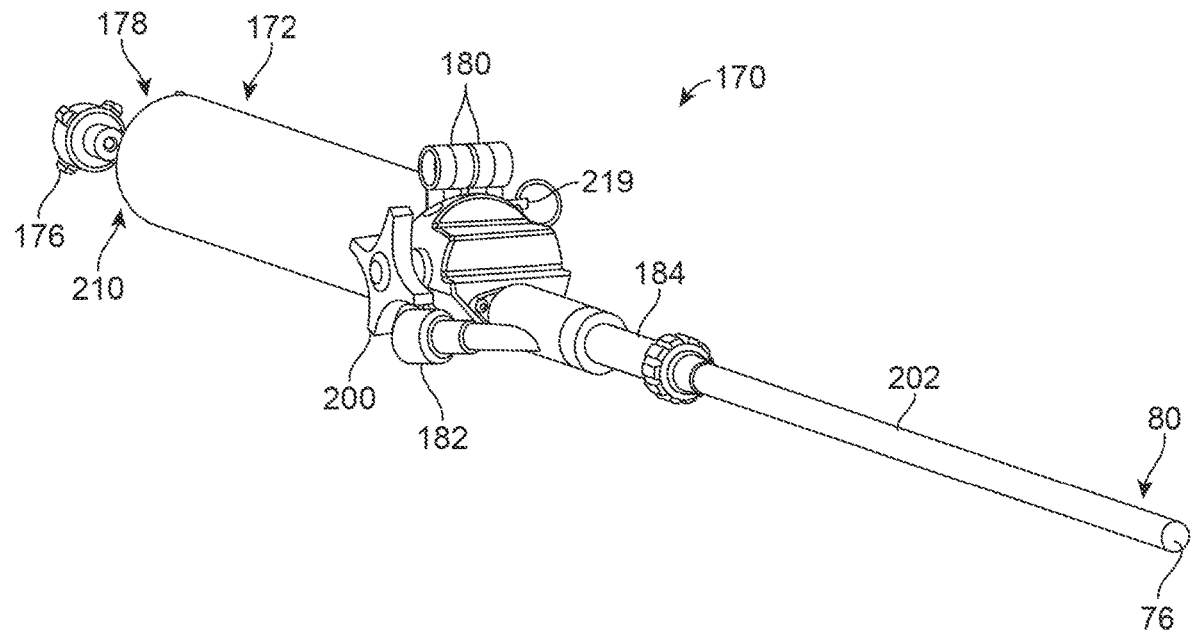
FIG. 13A shows a perspective view of a delivery assembly.

As previously described, the delivery assembly 170 described above is shown in another perspective view of FIG. 13A. Generally, to deploy the obstructing member from the delivery assembly 170, the proximal occluding member 72 may be introduced into the patient body by first advancing the member 72 in its uncoiled and elongated configuration. The lock lines may be tensioned through the coiled member 80 in its nested configuration while the distal portion of the coiled member 80 is maintained at a predetermined distance from the distal opening of the delivery tube to allow the coiled member 80 to nest into its compacted configuration upon the distal portion. The tension lines 226 can be coupled to the lock lines. The tension in the gastric obstruction device 70 can be released prior to locking the coiled member 80 and then the coiled member 80 can be locked into compacted configuration. The tension in the tension lines 226 may also be released prior to line cutting and removal of the tension lines With the tension lines 226 cut, the anchor line may also be removed from the control assembly and the gastric obstruction device 70. The gastric obstruction device 70 may then be released entirely from the delivery system. The delivery tube 184 may be optionally disengaged from an overtube 202 and the delivery assembly may be removed from the patient body by either proximally withdrawing the delivery tube 184 while leaving the overtube 202 in place within the patient or both the delivery tube 184 and overtube 202 may be removed simultaneously from the patient body.

The delivery assembly 170 may have the tensioning control assembly 172 attached to a delivery tube 184 extending from the control assembly 172. The coiled member advancement control 200 may be seen extending from a side of the control assembly and the delivery tube 184 may be secured at least partially within an overtube 202. The overtube 202 may be positioned, e.g., within the patient's esophagus extending from the mouth to a location distal to the gastroesophageal junction within the stomach, to provide for a smooth and atraumatic passageway for the delivery tube 184 directly into the patient's stomach.

Figure 13B:
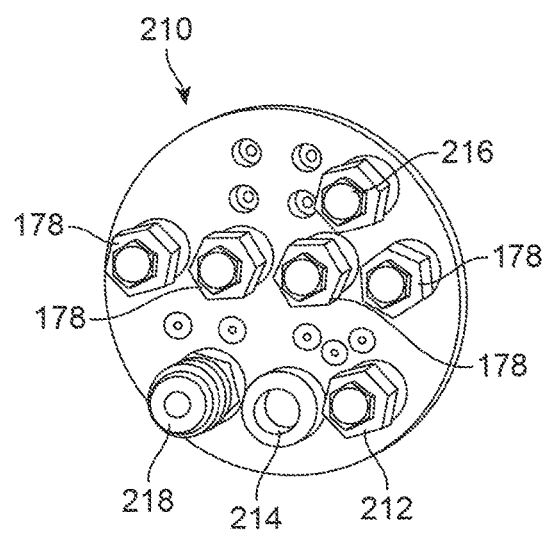
FIG. 13B shows a perspective view of a tensioning and release control interface located along the delivery assembly.

To control the advancement, coiling, and release of the gastric obstruction device 70 from the delivery assembly 170, a tensioning and release control interface 210 may be provided along a proximal end of the control assembly 172, as shown in the perspective view of FIG. 13B. The interface 210 may provide a number of various control mechanisms for actuating each of the advancement and release features for deploying the gastric obstruction device 70. For instance, the tension control interface 178 may be provided for tightening certain tension lines 226 and/or lock lines passing through the gastric obstruction device 70. Additional controls may also include, e.g., a coiled member release control 212 and tension release 216, for releasing the tension from the tension lines 226 and/or the lock lines and tensioning pins in the gastric obstruction device 70 prior to release from the delivery tube 184. Other controls may also include an anchor line removal knob 214 for removing the anchor line prior to device release as well as a pressure indicator, e.g., pressure gauge connector 218, for monitoring an insufflation pressure, e.g., within the stomach during device deployment. An optional pressure regulator or mechanism in communication with the pressure indicator may also be incorporated for automatically regulating the pressure. Moreover, a safety release pin 219 may also be removably provided for constraining each of the tensioning wire access handles 180 until the gastric obstruction device 70 is ready for deployment. Removal of the release pin 219 may allow for the access handles 180 to be pulled from the control assembly 172 to expose each corresponding tension line 226.

Figure 14:
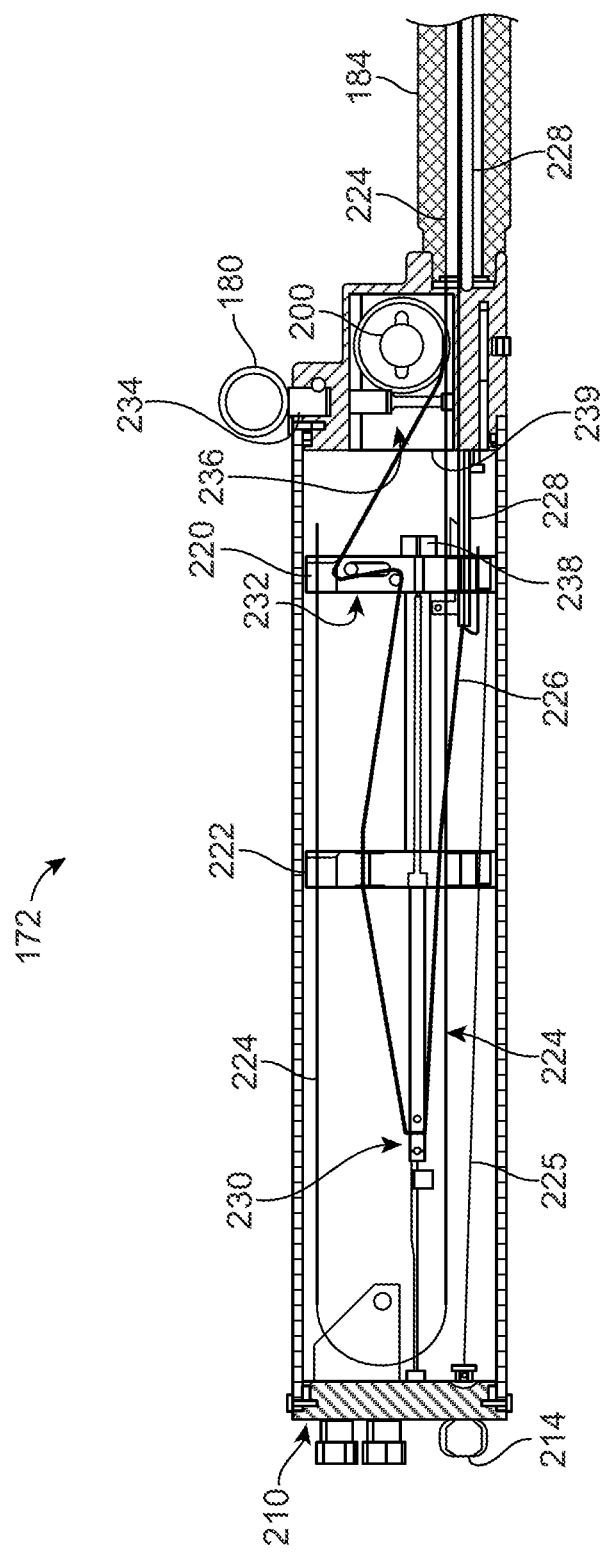
FIG. 14 shows a partial cross-sectional side view of the tensioning control assembly illustrating the tension lines and plunger routed through the control assembly.

FIG. 14 shows a partial cross-sectional side view of the control assembly 172 illustrating the various components. With the delivery tube 184 attached at a distal end of the control assembly 172, a control tube 228 may extend through the length of the delivery tube 184 and into attachment with the compliant pyloric contact section 78 of the gastric obstruction device 70. The multiple tension lines 226 may also pass through the delivery tube 184 and through the coiled member 80 for securing the gastric obstruction device 70 into its compacted and expanded configuration. The proximal ends of the tension lines 226 may pass into the control assembly 172 and about a tensioning member 230 which may be urged in a proximal direction to keep the tension lines 226 under constant tension. This tensile force may help to keep the tension lines 226 from tangling with one another or around other mechanisms. The tension lines 226 may wind around the tensioning member 230 and also through a tension line tensioning control 232 which may further provide a tensioning force within the tension lines 226. The tensioning control 232 may be comprised of two or more members which function as pulleys and these members may be optionally collapsed or drawn towards one another to release the tension within tension lines 226. The tension lines 226 may further pass through a corresponding access shaft opening 236 defined along each of the tensioning wire access shafts 234 which are attached to access handles 180.

A plunger 224 which comprise a flexible and structurally supportive member (e.g., a flexible, polymeric shaft) may also extend through the delivery tube 184 and into the control assembly 172. The length of the plunger 224 may optionally define one or more projections or depressions along its surface for engagement with the advancement control 200 such that as the control 200 is rotated, the control 200 may engage the projections or depressions to retract or advance the plunger 224 through the delivery tube 184 to correspondingly push and eject the coiled member 80 into its compacted configuration. Alternatively, the plunger 224 may be round or circular in cross-sectional diameter presenting a relatively smooth surface for engagement with the advancement control 200. In either case, the use of a plunger 224 may be optional since other advancement mechanisms may be used in other variations.

In another variation, the tension lines 226 can be coupled to lock lines (e.g., lock lines 126, 128, 130, etc.) which are used to lock the coiled member 80 in its compressed, wound, and nested configuration. The tension lines can be used to pull the coiled member 80 through the delivery tube 184 and out of the delivery tube 184 into a device cover 142 or device skin. The tension lines 226 can extend from a delivery assembly 170 (see FIGS. 10, 12G, 13A, and 27) through the turns of the coiled member 80 of the gastric obstruction device 70, and back into the delivery assembly 170 through a lumen of a control tube 228 (see FIGS. 18A, 18B, 18C, 18D, 22, 29A, and 29B). The tension lines 226 can be detached or otherwise separated from the lock lines. The tension lines 226 can then be cut and removed from the gastric obstruction device 70 (e.g., through the control tube 228) when the gastric obstruction device 70 is locked by the locked lines in the nested or wound configuration.

The anchor line 225 which may pass through the control assembly 172 may extend from the anchor line removal knob 214, through the control tube 228, and distally into and through central column 86 of the gastric obstruction device 70. The anchor line 225 may pass through the central column 86 where it may be looped through and around the distal hub 90 to maintain an attachment of the device to the control tube 228 until the anchor line 225 is removed to release the gastric obstruction device 70.

Within the control assembly 172, a distal carriage 220 and a proximal carriage 222 may slidably translate distally or proximally. The control tube 228 may be attached at least to the distal carriage 222 while the proximal and distal carriages 220, 222 may be initially attached to one another. In this manner, when the advancement control 200 is actuated to urge the control tube 228 distally, the carriages 220, 222 may also be advanced simultaneously to urge the compliant pyloric contact section 78 and distal hub 90 from the distal opening of delivery tube 184. With the carriages 220, 222 urged distally, the plunger 224 may also be urged distally as well through the delivery tube 184 until a plunger release mechanism 238 positioned on a distal surface of the distal carriage 220 comes into contact with the distal contact wall 239.

Once the plunger release mechanism 238 is actuated, the plunger 224 may be released from attachment with the distal carriage 220. Further actuation of the advancement control 200 may further urge advancement of the plunger 224 while maintaining the ejected distance of the control tube 228 constant to allow for the coiled member 80 to nest upon itself when deployed, as described in further detail below.

Figure 15A:
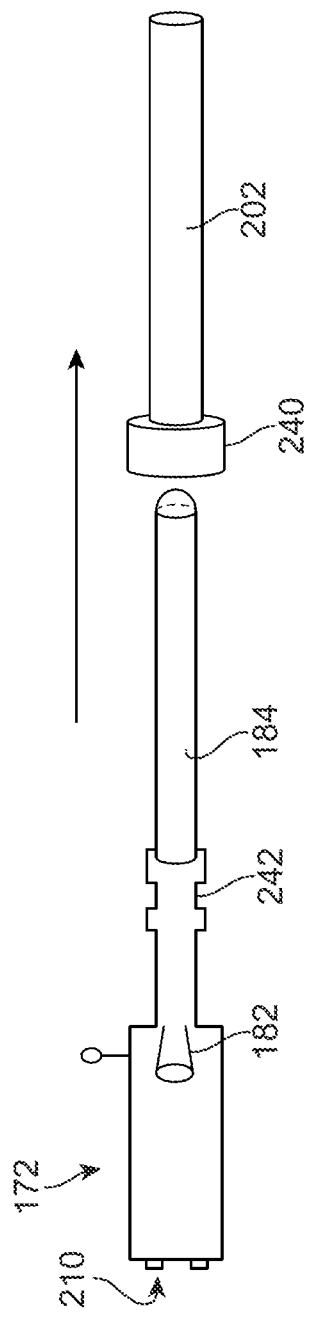
FIGS. 15A and 15B show illustrative side views of how the delivery tube may be secured within an overtube.
Figure 15B:
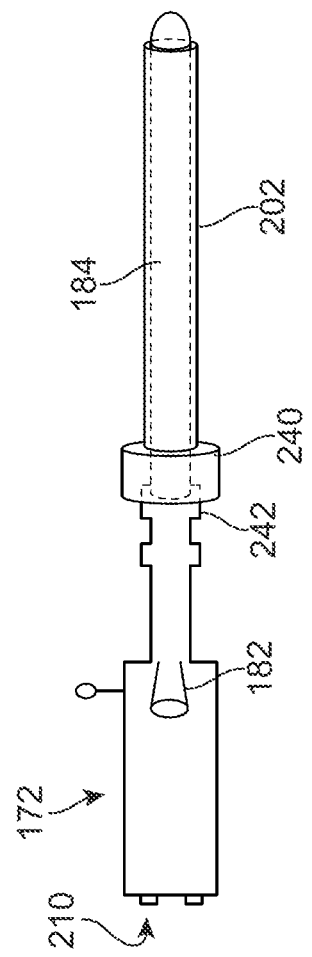

With the delivery assembly 170, the delivery tube 184 may be inserted within an overtube 202, as previously described and as shown in the side views of FIGS. 15A and 15B. The overtube 202 may comprise a hub connector 240 at its proximal end which may be optionally secured onto a corresponding hub interface 242 positioned along the delivery tube 184. One or both of the delivery tube 184 and overtube 202 may be lubricated and then advanced separately or simultaneously through the patient's mouth, esophagus, and at least partially into the patient's stomach, e.g., 2-3 cm, past the gastroesophageal junction. A visualization instrument such as an endoscope may be optionally inserted into the insufflation port 182 which is coupled to the delivery tube 184 to provide for direct visualization of the surrounding tissue during this initial insertion into the patient body to guide and facilitate positioning.

Figure 16A:
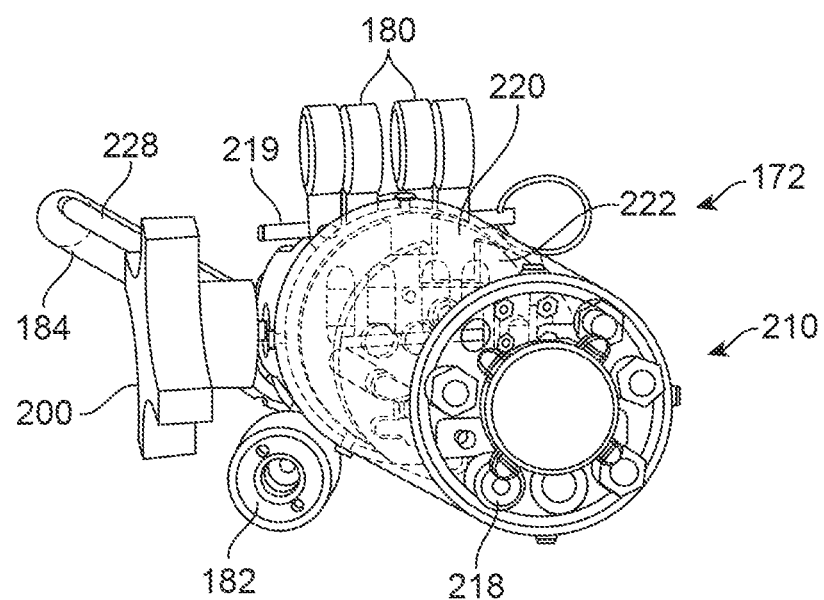
FIGS. 16A and 16B show various perspective views of the delivery assembly configured for insertion and insufflation of the patient.
Figure 16B:
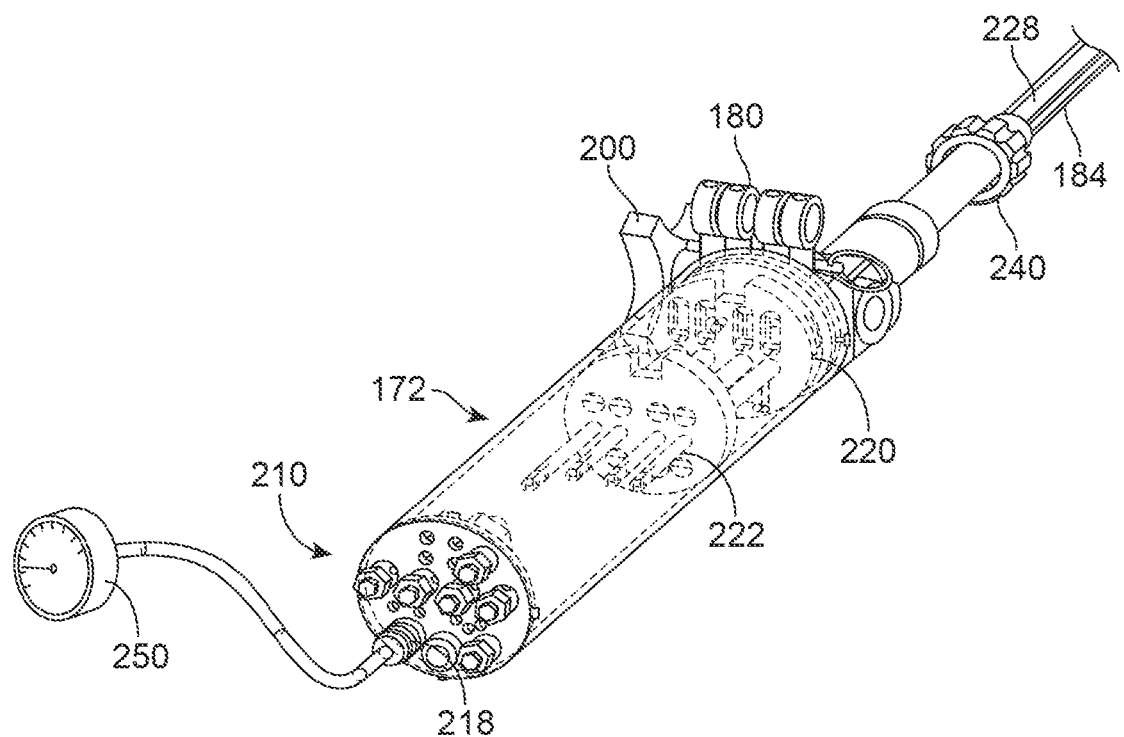

With the distal end of the delivery tube 184 so positioned, the stomach may be initially insufflated by introducing air or other gas, e.g., via an endoscope introduced through the insufflation port 182 shown in the perspective view of FIG. 16A. The insufflation procedure may also be optionally monitored visually by the endoscope as well. While insufflation of the stomach or body lumen may be optional, insufflating may facilitate the deployment and reconfiguration of the gastric obstruction device 70. The air or gas may be introduced via the endoscope which may be advanced into position through the port 182 once the distal occluding member 76 of the gastric obstruction device 70 has been deployed from the distal opening of the delivery tube 184. A pressure gauge 250 may be optionally attached to the pressure gauge connector 218 on the control interface 210 to monitor insufflation pressure within the stomach or body lumen, as shown in the perspective view of FIG. 16B.

Figure 17A:
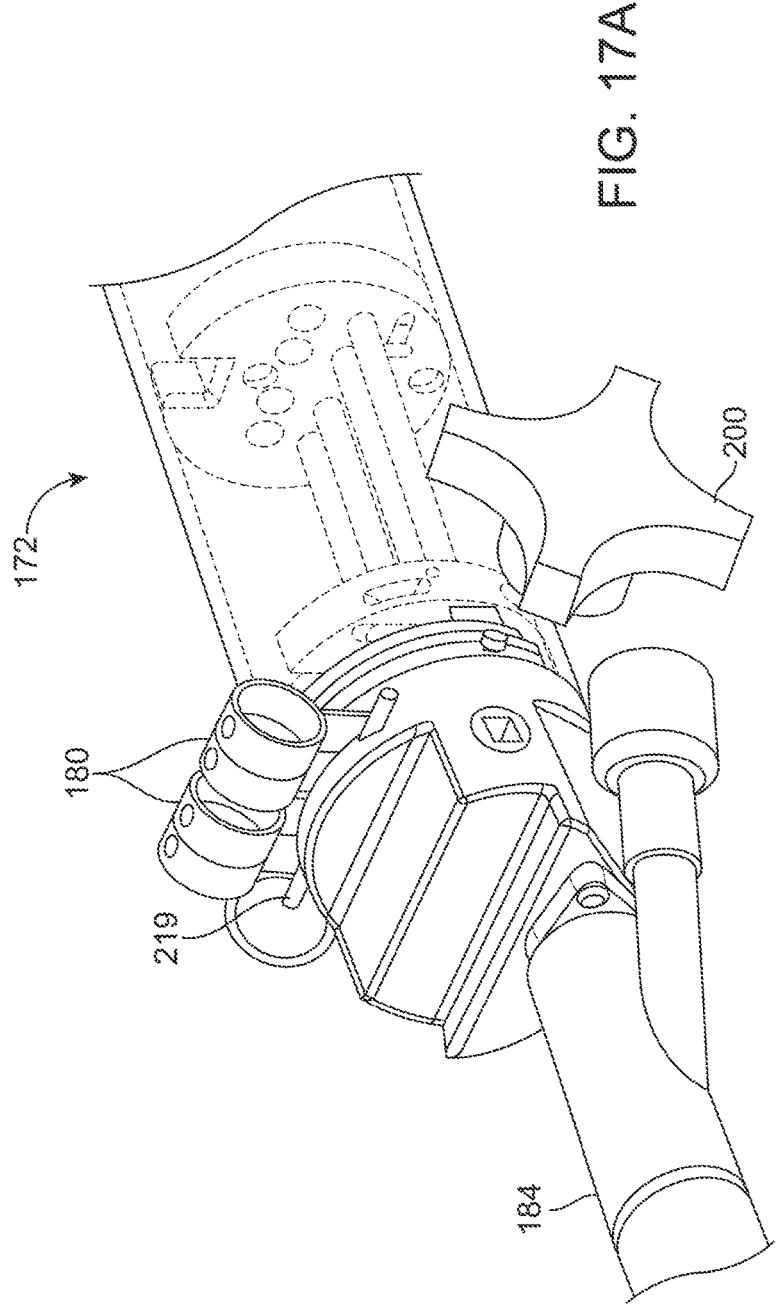
FIGS. 17A and 17B show detail perspective and side views of the control assembly actuated for initial deployment of the obstructing device.
Figure 17B:
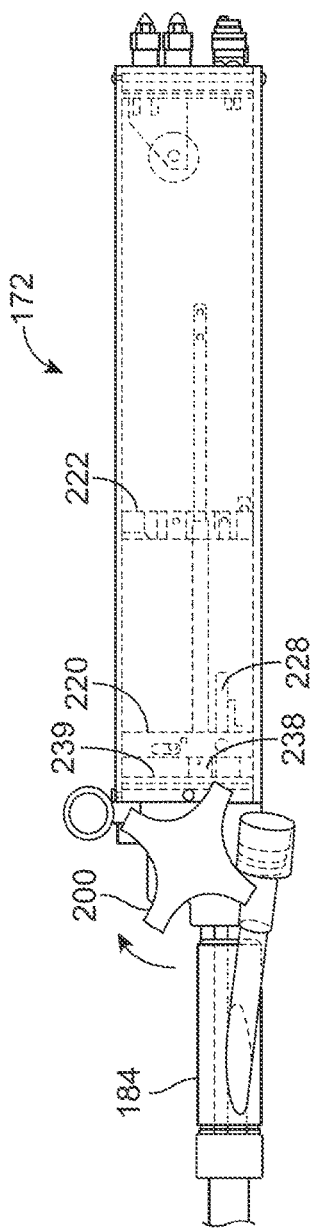

With the stomach or body lumen optionally insufflated, the gastric obstruction device 70 may be deployed from the delivery tube 184 and into the stomach by attaching the advancement control 200 to the control assembly 172, as shown in the perspective view of FIG. 17A, and then rotating the control 200 in a first direction, as shown in the side view of FIG. 17B. Advancement control 200 is illustrated as a control knob, however, any variation of the control may be utilized and the control itself may be removably attached or permanently coupled to the control assembly 172.

FIGS. 18A to 18D illustrate partial cross-sectional side views of the gastric obstruction device 70 being deployed from the delivery tube 184 as the advancement control 200 is actuated. Shown in FIG. 18A, the distal opening of the delivery tube is illustrated positioned in proximity to the stomach ST. As the control 200 is initially actuated, the distal occluding member 76, which may be initially positioned to cover the opening of the delivery tube 184 to function as an atraumatic tip, may be ejected into the stomach ST. With the distal occluding member 76 and the attached tether 74 ejected, compliant pyloric contact section 78 and attached distal hub 90 may also be advanced into the stomach by further actuating the control 200 to distally translate the control tube 228. The distal hub 90 and compliant pyloric contact section 78 may be translated at a deployment distance 260 relative to the delivery tube which is a distance distal to the opening of the delivery tube 184 sufficient to provide enough clearance for the proximal occluding member 72 to nest upon itself in its compacted configuration as the member 72 is ejected from the delivery tube 184, as shown in the side view of FIG. 18B.

The deployment distance 260 may be determined in part by the set distance between the distal carriage 220 and distal contact wall 239 within the control assembly 172, as previously described. As the advancement control 200 advances the control tube 228 and plunger 224, the plunger release mechanism 238 may be actuated upon contacting the distal contact wall 239 halting the further advancement of the control tube 228 and attached distal hub 90. However, the plunger 224 may continue its advancement relative to the control tube 228 and delivery tube 184 to further eject the coiled member 80 distally through the delivery tube 184. The ejected proximal occluding member 72 may thus continue to nest into its coiled structure as the advancement control 200 is further actuated.

The advancement control 200 may continue to urge the proximal occluding member 72 to reconfigure upon exiting the delivery tube 184 until the terminal end of the proximal occluding member 72 is advanced. The proximal plug 94 and release mechanism 110 may be urged distally along the control tube 228 by a plunger contact 262 positioned upon a distal end of the plunger 224, as shown in the side view of FIG. 18C. At least two of the lock lines 126, 128 (only two are shown for clarity) which pass at intervals through the lengths of the proximal occluding member 72 may align through the member 72 as the member 72 nests upon itself. The lock lines (for example, lock lines 126 and 128) can be coupled to tension lines 226. The lock lines and/or the tension lines 226 can function to provide a rail or guide rail to the member 72 as it is advanced out of the delivery tube 184 by facilitating the positioning of the member 72 in nesting upon itself since the lines may automatically guide the member 72 into place. Also shown are the corresponding tensioning wire pins 114, 116 along the respective lock lines 126, 128.

One particular aspect of the deployment and reconfiguration of the member 72 from the delivery tube 184 is that the distal end of the gastric obstruction device 70 may be reconfigured or built first while the remainder of the gastric obstruction device 70 is formed towards its proximal end. That is, the gastric obstruction device 70 is reconfigured or formed from its distal end and towards its proximal end. This may allow for the progressive reconfiguration or formation of the gastric obstruction device 70 as it exits the delivery tube 184. Such a reconfiguration may also obviate any need to expel the entire gastric obstruction device 70 into the stomach prior to tensioning to maintain its deployed configuration.

Figure 18A:
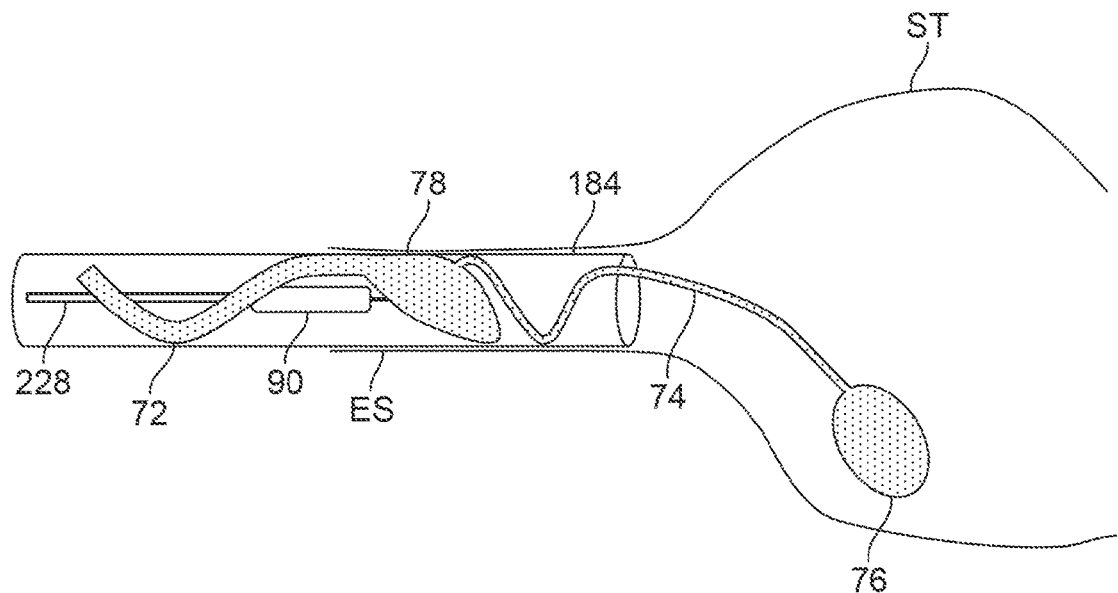
FIGS. 18A and 18B illustrate partial cross-sectional side views of the coiled member being deployed from the delivery tube and coiled about the distal hub and control tube.
Figure 18B:
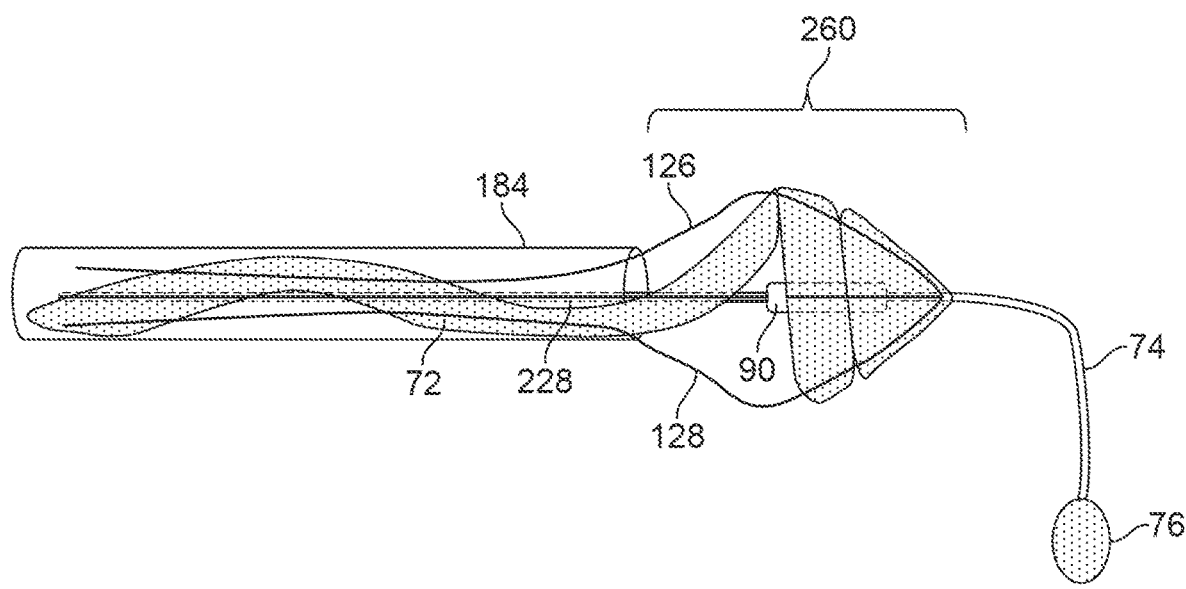
Figure 18C:
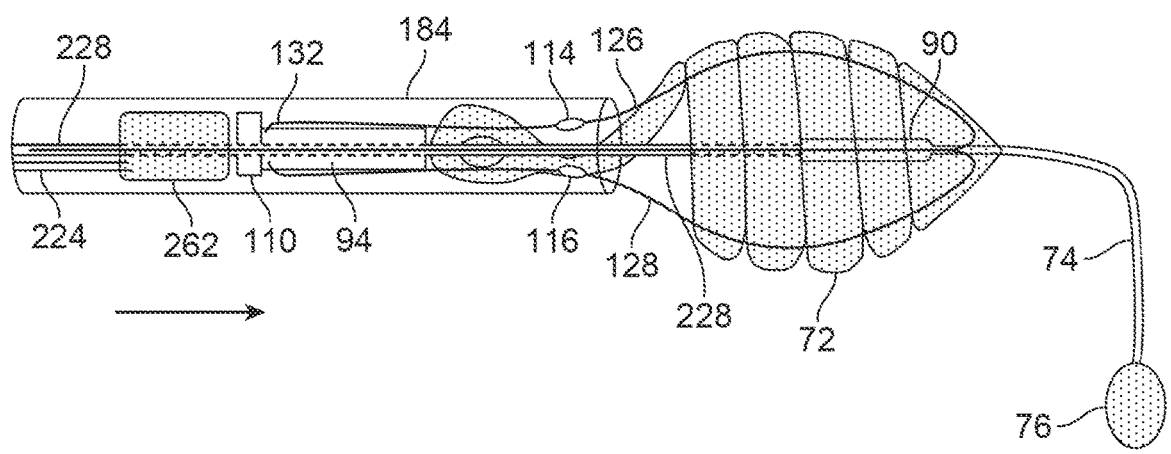
FIGS. 18C and 18D illustrate further nesting of the coiled member and the advancement of tensioning wire pins through the coiled member.
Figure 18D:
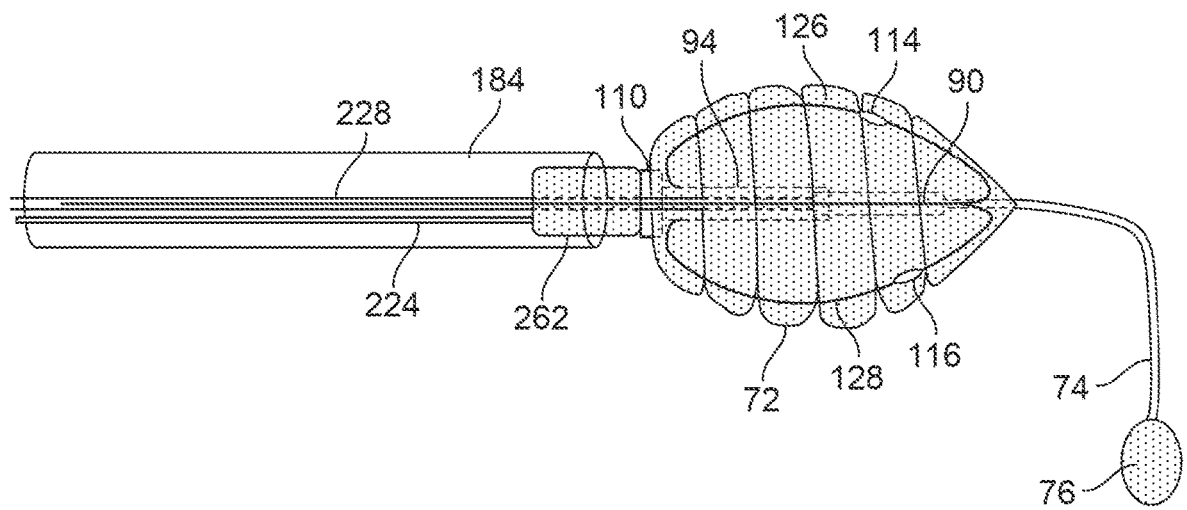

The advancement control 200 may be actuated until the proximal occluding member 72 is completely nested and reconfigured into its coiled and compacted configuration. The proximal plug 94 and release mechanism 110 may thus be advanced along the control tube 228 by the plunger contact 262 until the proximal plug 94 is seated and placed into engagement with the distal plug 90, as shown in FIG. 18D.

Figure 19A:
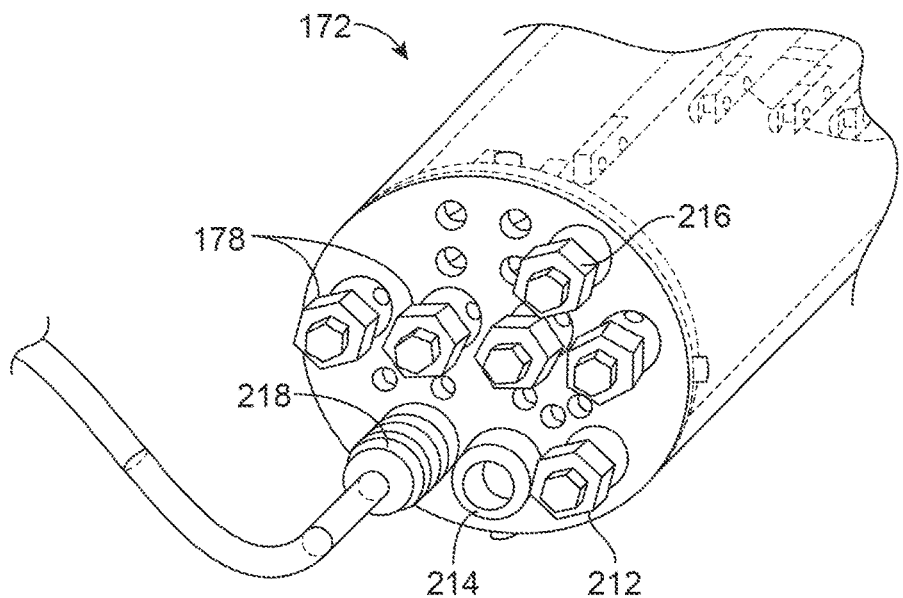
FIGS. 19A and 19B show detail perspective views of the control assembly being actuated to release tension in the tensioning wire pins prior to release.
Figure 19B:
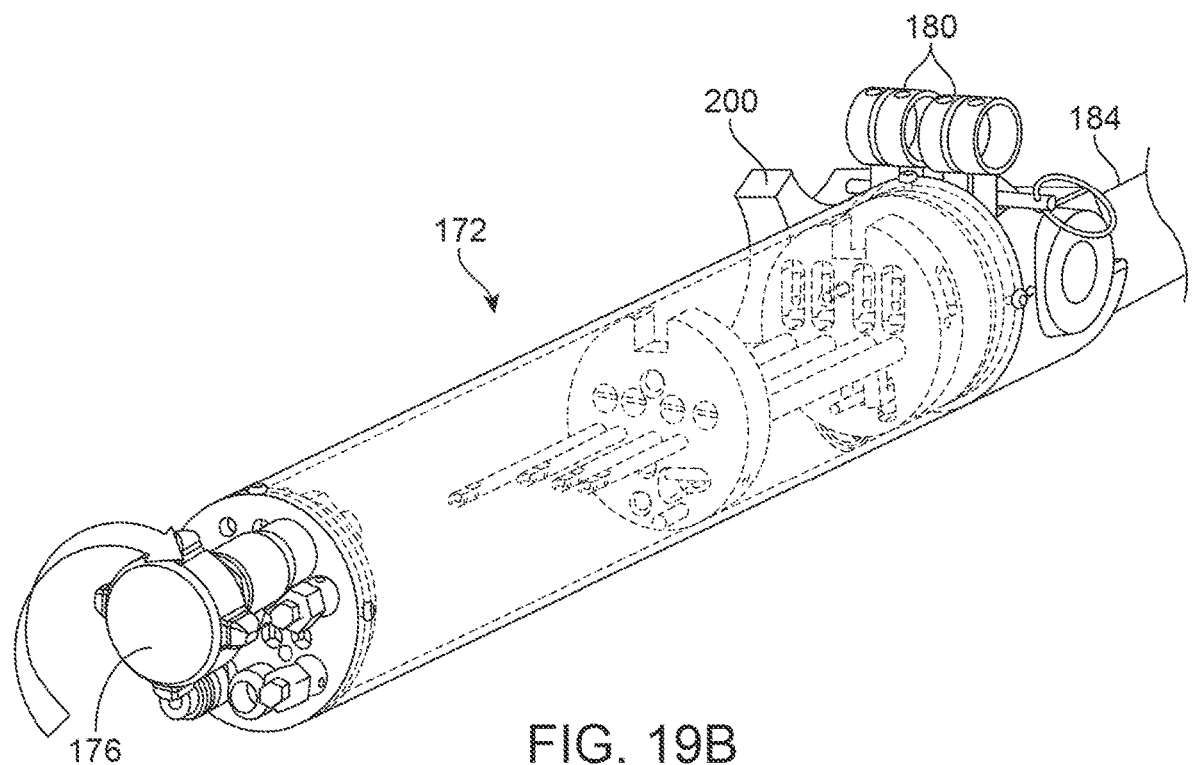

Because the lock lines and corresponding tensioning wire pins are placed under tension during the device deployment to prevent tangling of the lock lines, the tension in the lock lines and tensioning wire pins may be released prior to tightening of the lock lines. The tension release 216 control located along the control interface may thus be actuated, e.g., via the loop tensioner control 176, to release the tension in the lines, as shown in the perspective views of FIGS. 19A and 19B.

The lock lines may then be tightened and locked into position to maintain the compacted and coiled configuration of the gastric obstruction device 70. Optionally, the locking of the proximal occluding member 72 may be done while under direct visualization via, e.g., an endoscope positioned within the Y-port 182, as shown in the perspective view of FIG. 20A. In either case, the control 176 may be used to engage and tighten each of the tension control interface 178 for each corresponding lock line passing through the gastric obstruction device 70. The control 176 may be moved sequentially through each of the control interface 178, as shown in the perspective views of FIGS. 20B and 20C, such that each is actuated until an indicator is given to the operator, e.g., an audible click or alert and/or tactile indication, that the lock line has been tightened sufficiently.

Figure 21:
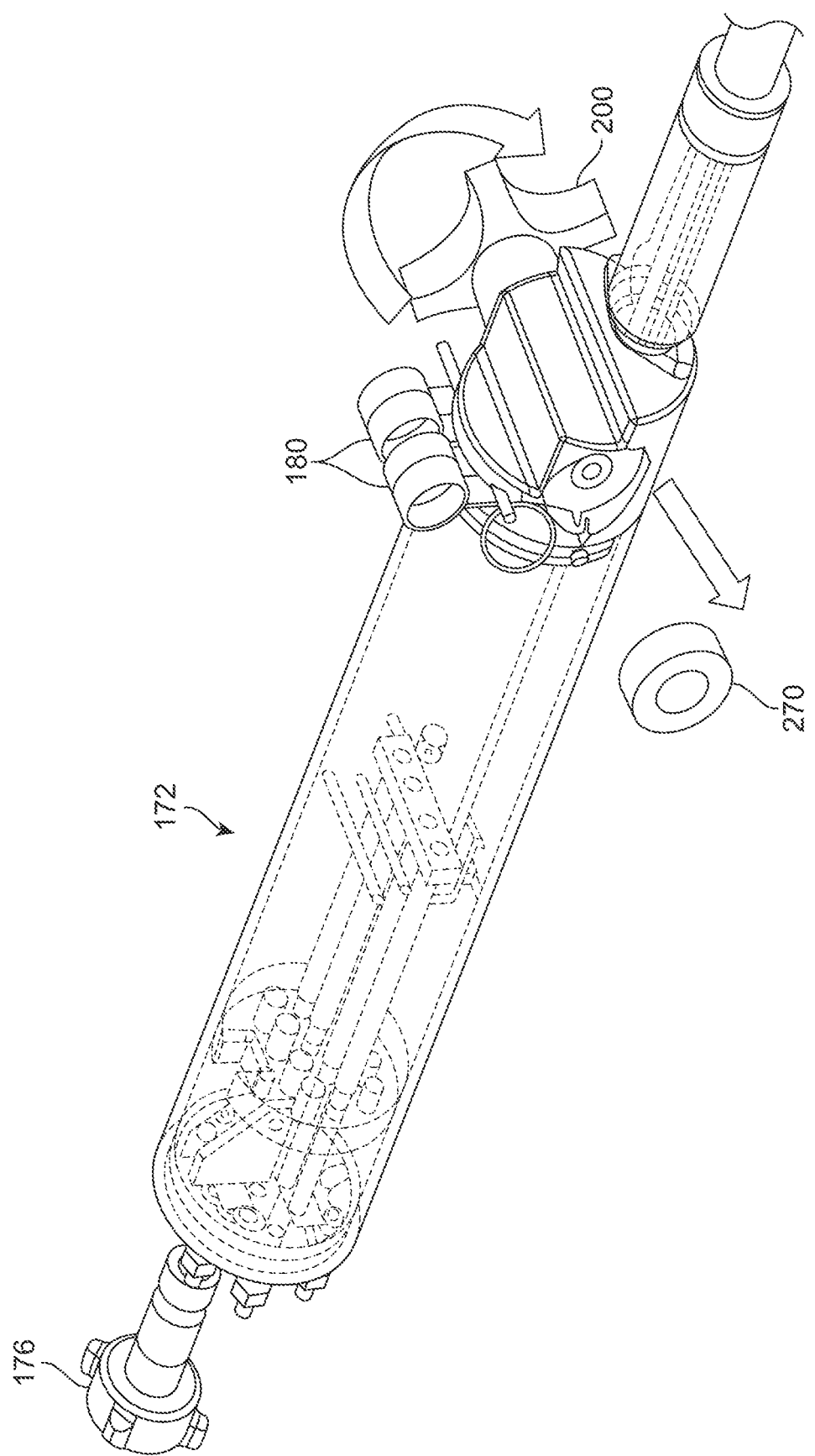
FIG. 21 shows a perspective view of the control assembly actuated to release tension from the tension lines.

With the lock lines tightened within the proximal occluding member 72, the advancement control 200 may then be used to release tension in the remainder of the lock lines prior to their removal for device release from the delivery tube 184. A ratchet control disc 270 may be disengaged from the advancement control 200, as shown in the perspective view of FIG. 21, such that the advancement control 200 may then be further actuated to release all tension on the lock lines.

Figure 22:
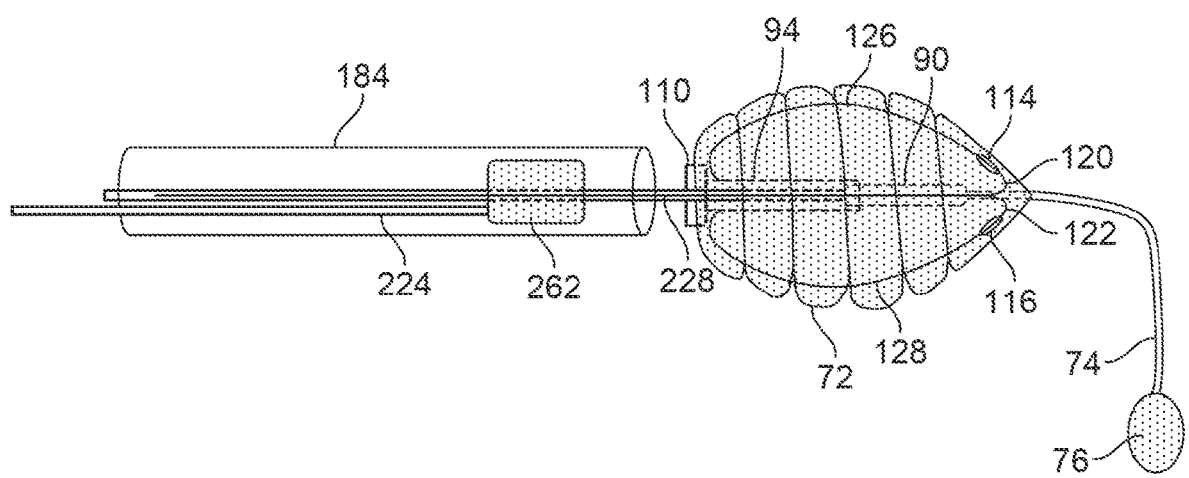
FIG. 22 shows a partial cross-sectional side view of the tensioning wire pins locked within the obstructing device to maintain the compacted configuration.

FIG. 22 shows a side view of the coiled proximal occluding member 72 where the lock lines 126, 128 have been tensioned through coiled member 80 such that the tensioning wire pins 114, 116 are urged distally through the member 72 and into a locking engagement with their corresponding collets 120, 122, as previously described herein. While only two lock lines and their respective wire pins are shown, any number of lock lines may be utilized as also previously described.

Figure 23A:
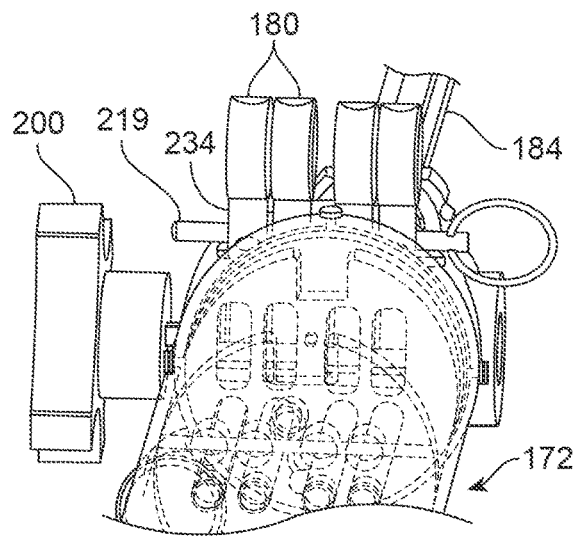
FIGS. 23A to 23C show detail perspective and end views of the control assembly.
Figure 23B:
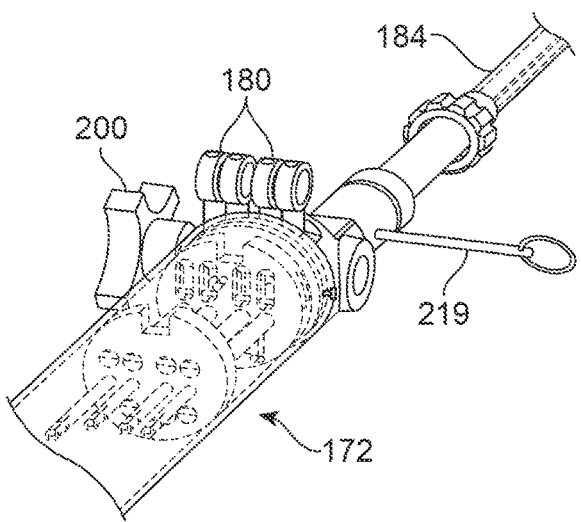
Figure 23C:
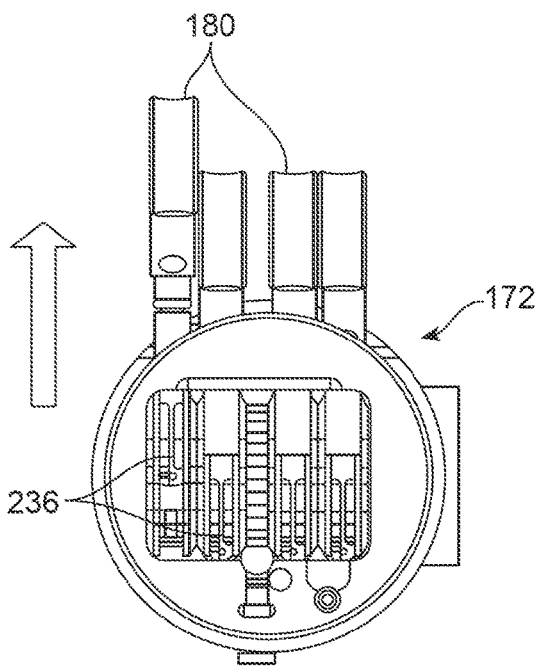

With the gastric obstruction device 70 locked into its coiled and compacted configuration, the tension lines attached to the gastric obstruction device 70 may be cut and the remainder removed from the gastric obstruction device 70. In order to access the tension lines which pass through a corresponding access shaft opening 236 defined along each of the tensioning wire access shafts 234, the safety release pin 219 may be removed from the access shafts 234, as shown in FIGS. 23A and 23B. With the release pin 219 removed, each access handle 180 may be pulled, e.g., sequentially, as shown in the end view of FIG. 23C, to expose the corresponding tension lines passing through the shaft opening. With the tension lines exposed, they may each be cut to sever the tension lines from the control assembly 172.

Figure 24A:
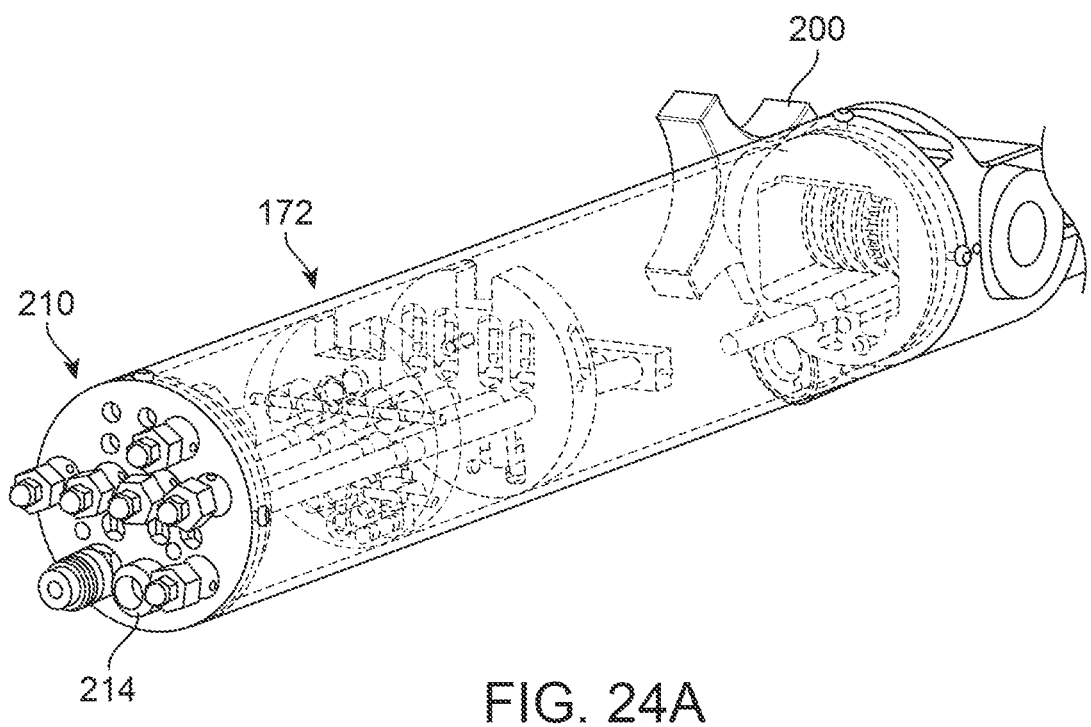
FIGS. 24A and 24B show perspective views of the anchor line removal knob released from the control assembly for removing the anchor line from the obstructing device.
Figure 24B:
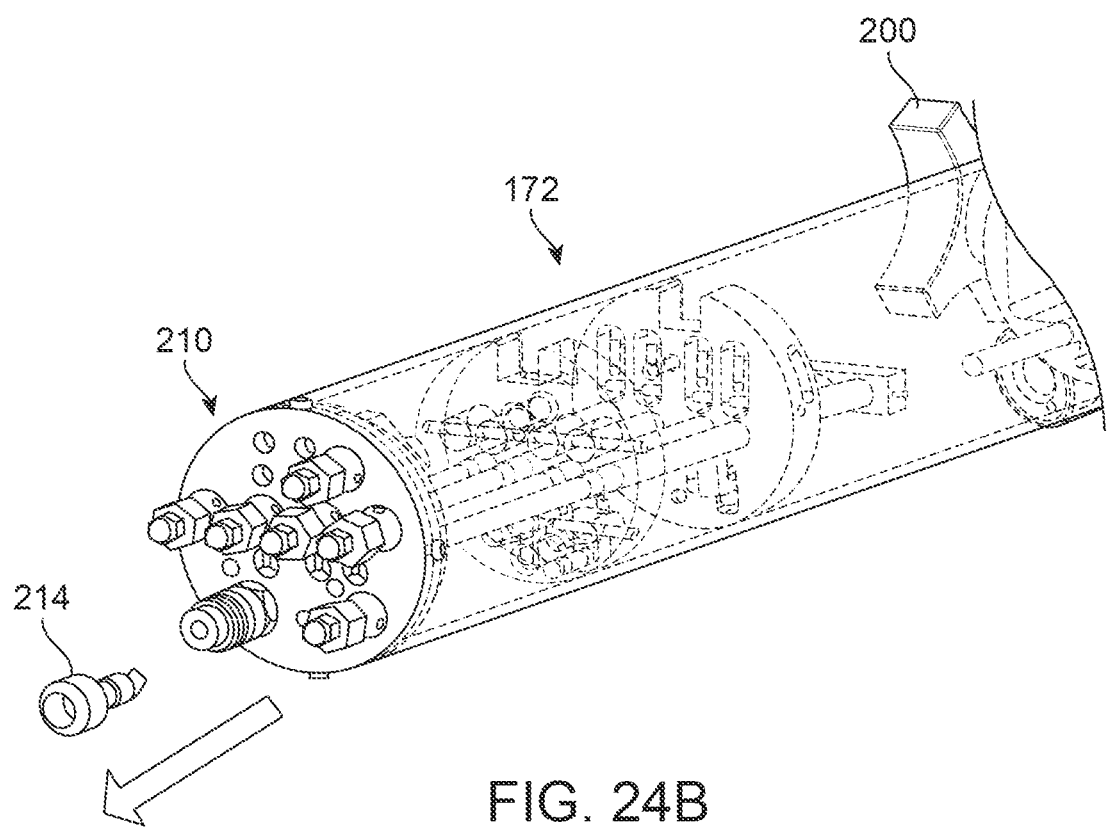
Figure 25:
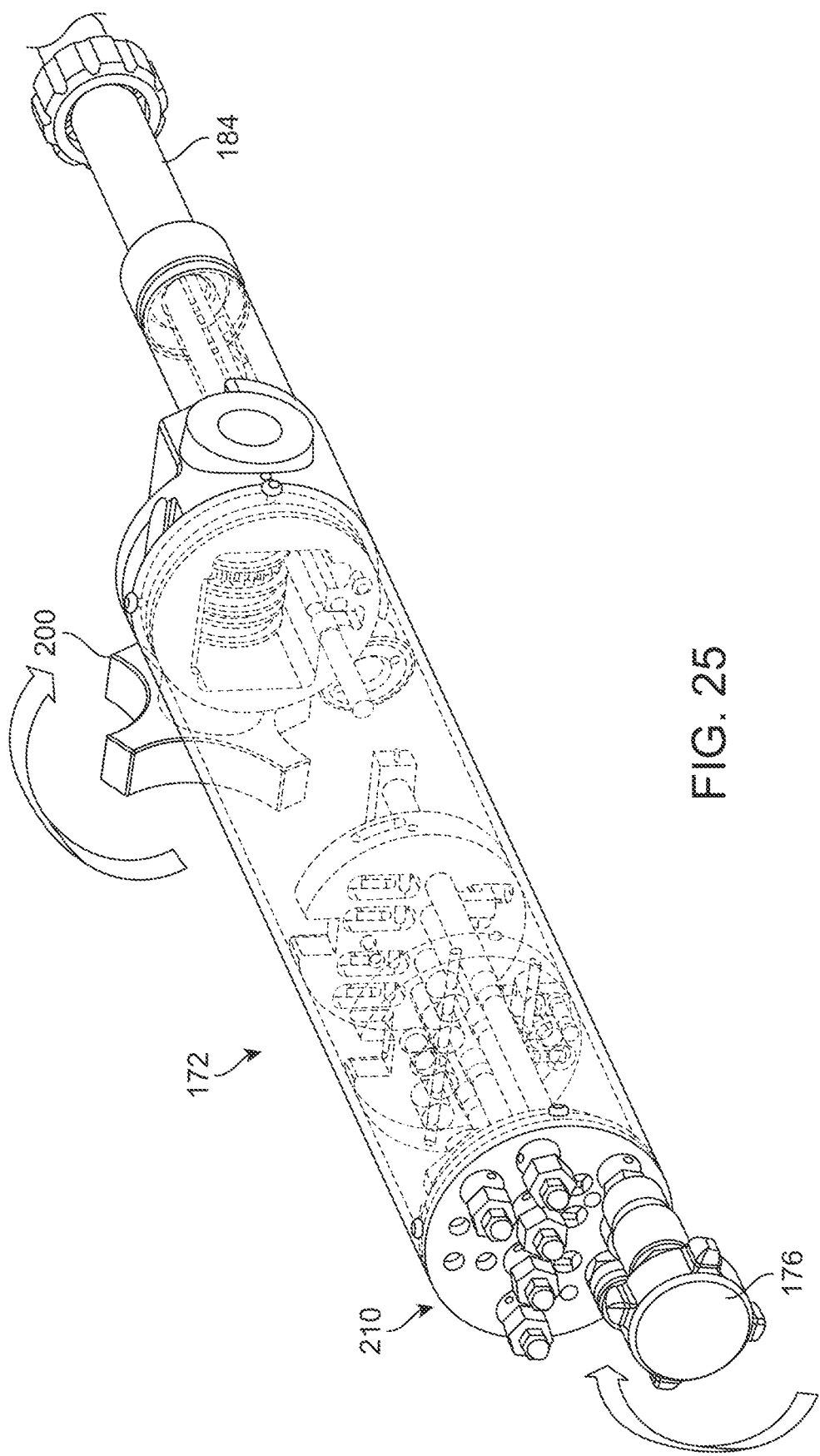
FIG. 25 shows a perspective view of the control assembly actuated to release the obstructing device from the delivery tube.

Even with the tension lines severed, the gastric obstruction device 70 may remain attached to the control tube 228. The anchor line removal knob 214 may be located along the control interface 210, as shown in the perspective view of FIG. 24A, and removed from the control assembly 172. The attached anchor line 225 which passes through the control assembly 172, control tube 228, through the distal hub 90, and openings 132 along the proximal plug 94 may be removed entirely from the system to completely detach the gastric obstruction device 70 from the delivery system. The tension control 176 may then be used to actuate the release control 212 along the interface 210 and the advancement control 200 may be actuated as well to fully retract the plunger 224 and plunger contact 262 into the delivery tube 184, as shown in the perspective view of FIG. 25.

Figure 26:
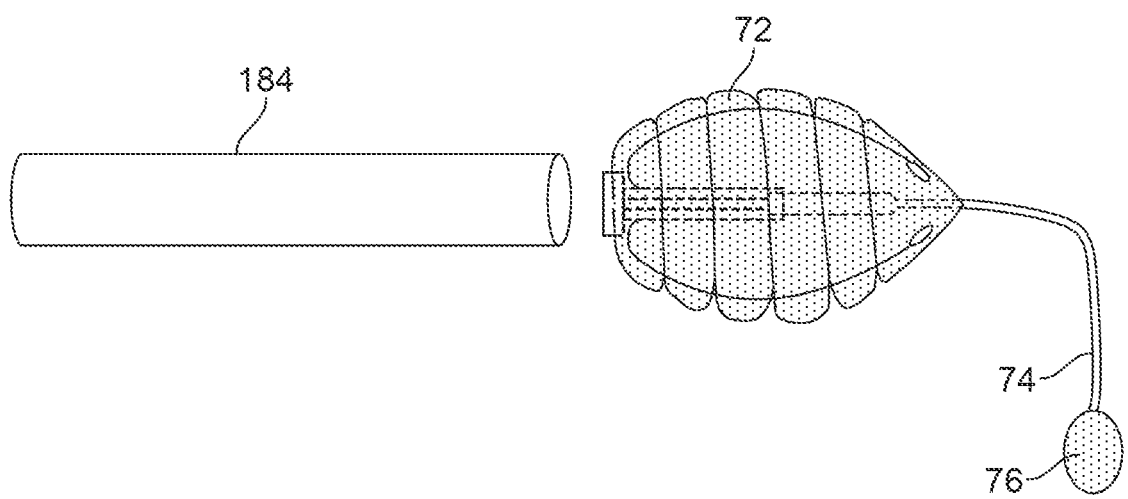
FIG. 26 shows a detailed side view of the obstructing device released.

FIG. 26 illustrates a side view of the locked proximal occluding member 72 which is fully enclosed and with all remaining tension lines 226 and anchor line removed from the obstructing member and plunger 224 fully retracted. The delivery system 170 and delivery tube 184 may then be removed from the patient body by withdrawing the gastric obstruction device 70 from the stomach or body lumen entirely, as shown in FIG. 27. The delivery assembly 170 along with the overtube 202 may be removed simultaneously from the esophagus and mouth of the patient. Alternatively, the hub connector 240 may be disengaged from the delivery tube 184 and the delivery assembly 170 and delivery tube 184 may be optionally withdrawn from the patient body while leaving the overtube 202 within the patient. An endoscope may be optionally introduced into and through the overtube 202, if left in the patient, to provide for visualization of the gastric obstruction device 70 remaining in the stomach. Once the procedure is completed, the overtube 202 may then be removed from the patient body as well.

Figure 28A:
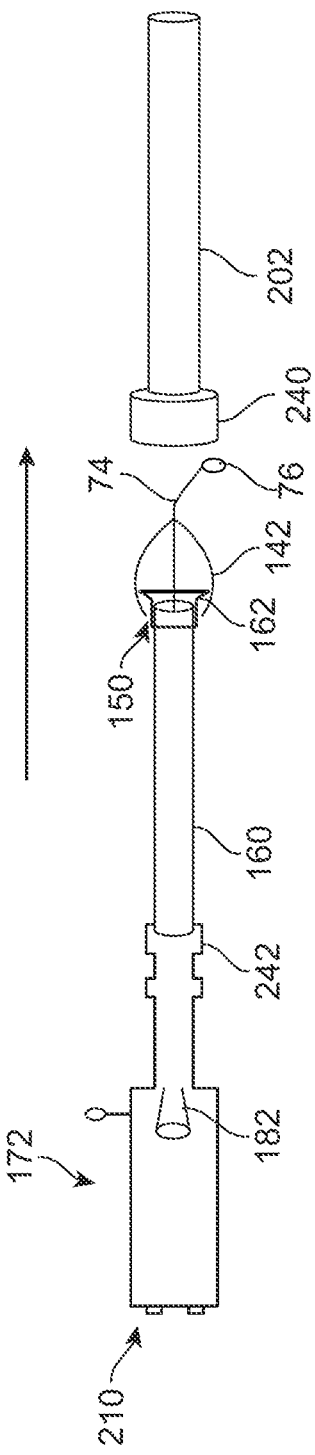
FIGS. 28A and 28B show illustrative side views of how a delivery tube may be secured within an overtube where the delivery tube may have a device cover or skin positioned at its distal end for deployment within the patient body.
Figure 28B:
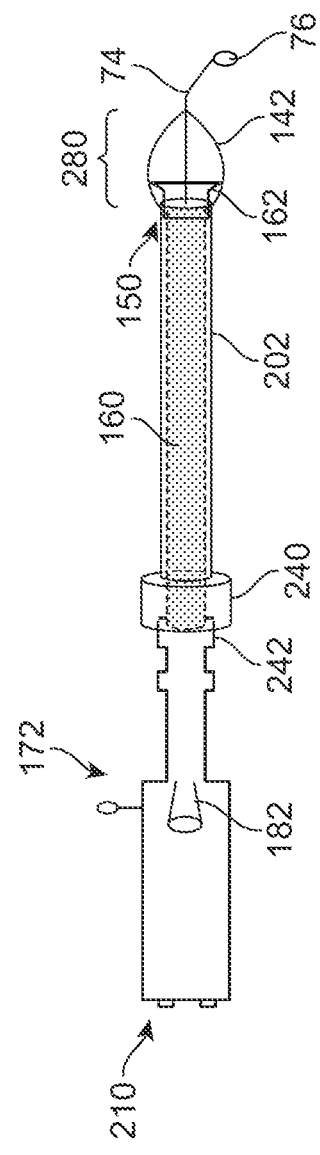
Figure 29A:
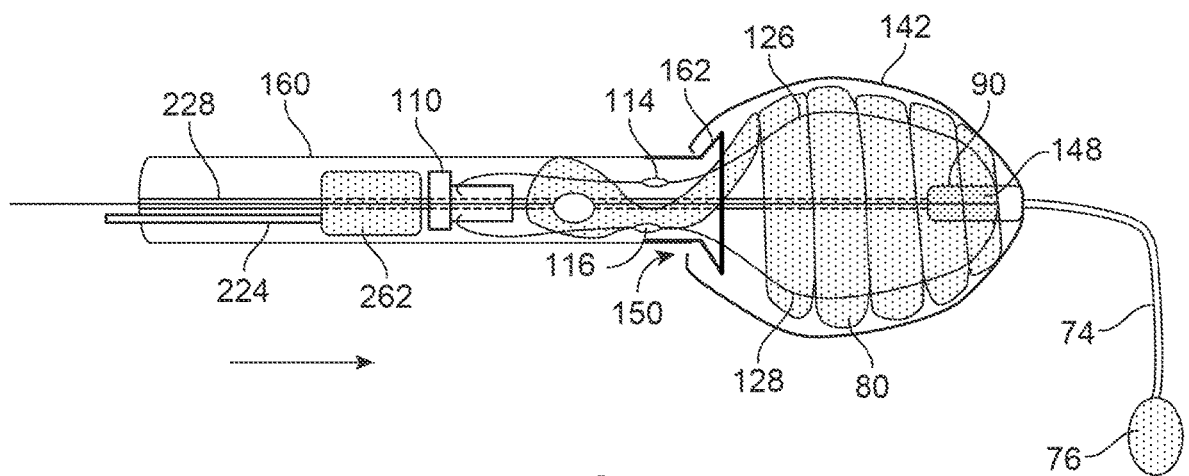
FIGS. 29A and 29B show partial cross-sectional side views of a coiled member being deployed within the device cover or skin when positioned within the patient body.
Figure 29B:
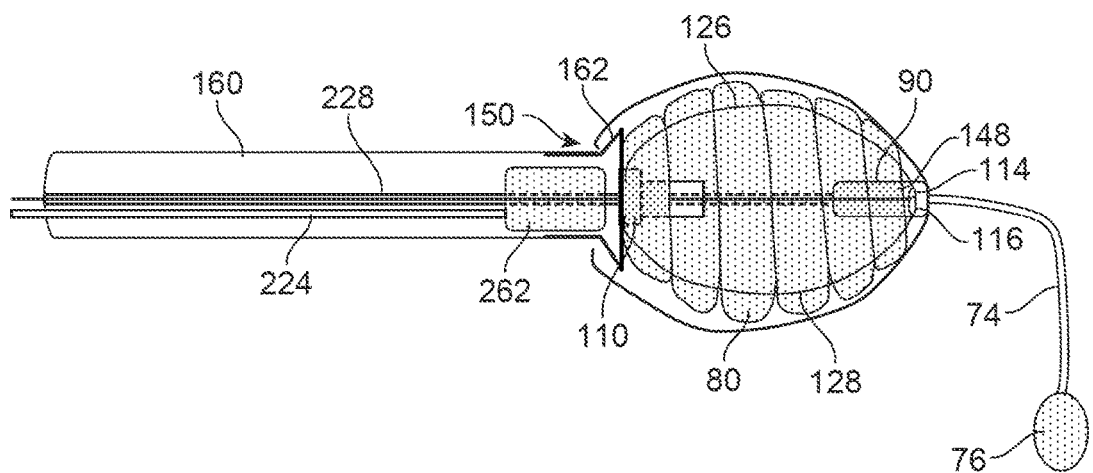

In deploying the embodiment of the gastric obstruction device 70 described above having a separate device cover 142, coiled member 80 may be deployed in a similar manner from the delivery tube 160 having the device covering interface 162 (see also FIGS. 9A to 9C). The device covering interface 162 can be a flange which widens or tapers outward in a distal direction (i.e., funnel-shaped). In this variation, the device cover 142 may already be attached at its opening 150 around the device cover interface 162 when the overtube 202 and hub connector 240 are slid over the delivery tube 160, as shown in the side view of FIG. 28A. As the hub connector 240 is secured, the device cover 142 extending from the opening of the delivery tube 160 may already set the deployment distance 280 of the control tube 228 due to the length of the device cover 142, as shown in the side view of FIG. 28B.

Similar to the deployment of the proximal occluding member 72 previously described, the proximal coiled member 80 may be advanced through the delivery tube 160 by actuating the plunger 224 distally. The member 80 may be introduced into and about the distal hub 90 and attachment collar 148 contained within the device cover 142 as the member 80 nests about itself into its compacted configuration, as shown in the side view of FIG. 29A. Upon further actuation of the plunger 224 and plunger portion 262, the proximal plug 94 and release mechanism 110 may be translated into a secured position, as shown in the side view of FIG. 29B.

Figure 30:
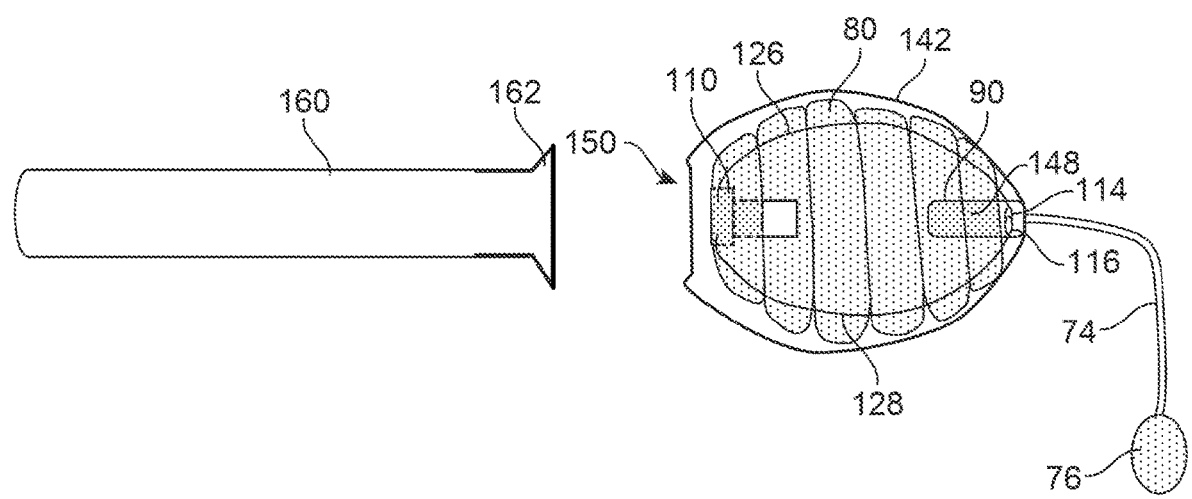
FIG. 30 shows a side view of the obstructing device and device cover or skin released from the overtube.

Each of the respective lock lines may then be tightened until the tensioning wire pins are locked in their respective collets. The anchor line may then be released from the control assembly 172 and pulled to remove the anchor line from the gastric obstruction device 70 to release it from the delivery tube 160, as shown in the side view of FIG. 30.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A deployment system comprising:
   an intermittently obstruction gastric obstruction device;
   a delivery tube having a lumen therethrough and a distal opening;
   a control tube slidably positioned through the delivery tube;
   a control assembly attached at a proximal end of the delivery tube, and wherein the control assembly further comprises:
      a plunger slidably extending from the control assembly and into the delivery tube to push the gastric obstruction device out of the delivery tube, and
      a carriage slidably positioned therethrough and attached to a proximal end of the control tube and further comprising an actuatable plunger release configured to release the plunger from the carriage when actuated;
   one or more tension lines extending through the control assembly and through the delivery tube, wherein the control assembly is configured to maintain the tension lines under tension; and
   an advancement control positioned along the control assembly and operatively coupled to the control tube.

2. The system of claim 1, wherein the lumen of the delivery tube is configured to house the gastric obstruction device while the gastric obstruction device is positioned in an elongated and collapsed configuration.

3. The system of claim 2 wherein a distal end of the control tube is configured to be coupled to a compliant pyloric contact section of the gastric obstruction device.

4. The system of claim 2 wherein the one or more tension lines extending through the delivery tube further extend through the gastric obstruction device when at least part of the gastric obstruction device is within the delivery tube.

5. The system of claim 2 further comprising an anchor line positioned through the control assembly and passing through the gastric obstruction device.

6. The system of claim 1, wherein the control assembly further comprises one or more control interfaces, wherein each of the control interfaces is coupled to one of the tension lines for further applying a tensile force to the tension line.

7. The system of claim 1 wherein the control tube is slidably advanceable to a distal position where the control tube decouples from the advancement control.

8. The system of claim 1 wherein the control tube extends at least partially within the control assembly.

9. The system of claim 1, wherein the plunger defines one or more projections or depressions along a length of the plunger for engagement with the advancement control.

10. The system of claim 1 wherein the tensioning mechanism is configured to release the one or more tension lines to release the tension.

11. The system of claim 1 further comprising a pressure indicator in fluid communication with the delivery tube.

12. The system of claim 11 further comprising a pressure regulator or mechanism in communication with the pressure indicator.

13. The system of claim 1 further comprising a port in fluid communication with the delivery tube.

14. The system of claim 1 further comprising one or more wire access handles positioned along the control assembly, wherein the one or more tension lines pass through a corresponding shaft of the wire access handle.

15. The system of claim 1, wherein the one or more tension lines are configured to be cut or released after the gastric obstruction device is deployed.

16. The system of claim 1 further comprising a flange extending from a distal end of the delivery tube.

17. The system of claim 16 further comprising a device cover attached to the flange.

18. The system of claim 1 further comprising an access sheath slidably positionable over the delivery tube.

19. The system of claim 18 further comprising an inflatable member positioned near or at a distal end of the access sheath.

* * * * *